United States Patent [19]
Jorgensen et al.

[11] Patent Number: 6,080,754
[45] Date of Patent: Jun. 27, 2000

[54] PYRROLO[2,1,5-CD]INDOLIZINE DERIVATIVES USEFUL IN THE PREVENTION OR TREATMENT OF ESTROGEN RELATED DISEASES OR SYNDROMES

[75] Inventors: Anker Steen Jorgensen, Copenhagen O; Poul Jacobsen, Slangerup; Lise Brown Christiansen, Lyngby; Paul Stanley Bury, Copenhagen NV; Anders Kanstrup, Espergœrde, all of Denmark

[73] Assignee: Novo Nordisk A/S, Bagsvaerd, Denmark

[21] Appl. No.: 09/088,404

[22] Filed: Jun. 1, 1998

Related U.S. Application Data
[60] Provisional application No. 60/049,061, Jun. 10, 1997.

[30] Foreign Application Priority Data

Jun. 4, 1997 [DK] Denmark .................. 0655/97

[51] Int. Cl.⁷ .................. A61K 31/44; C07D 471/12
[52] U.S. Cl. .................. 514/294; 546/94
[58] Field of Search .................. 546/94; 514/294

[56] References Cited

U.S. PATENT DOCUMENTS 2,986,563  5/1961  Boekelheide et al. .................. 546/94

OTHER PUBLICATIONS

Tsuchiya et al. "thermal intramolecular cyclization of 2–ethynylpyridine N–ylides to indolizines and cyclazines" Chem. Phar. bull. v.32(11) 4666–4669, 1985.

Pohjala "Indolizine Derivatives IX . . . " J. Het. Chem. vol. 15(6) 955–960, 1978.

Sashida et al. "Thermal reaarangement of cyclic amine ylides . . . " CA 110:231395, 1988.

*Primary Examiner*—Ceila Chang
*Attorney, Agent, or Firm*—Steve T. Zelson; Carol E. Rozek

[57] ABSTRACT

The present invention relates to therapeutically active compounds of formula I

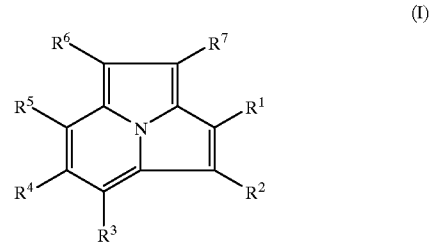

(I)

a method of preparing the same and to pharmaceutical compositions comprising the compounds. The novel compounds are useful in the prevention or treatment of estrogen related diseases or syndromes.

16 Claims, No Drawings

PYRROLO[2,1,5-CD]INDOLIZINE DERIVATIVES USEFUL IN THE PREVENTION OR TREATMENT OF ESTROGEN RELATED DISEASES OR SYNDROMES

CROSS-REFERENCE TO RELATED APPLICATIONS

This application claims priority under 35 U.S.C. 119 of Danish application 0655/97 filed Jun. 4, 1997 and of Provisional application serial No. 60/049,061 filed Jun. 10, 1997, the contents of which are fully incorporated herein by reference.

FIELD OF THE INVENTION

The present invention relates to new pyrrolo[2,1,5-cd] indolizine derivatives and the use of such compounds in the prevention or treatment of estrogen related diseases or syndromes, preferably diseases or syndromes caused by an estrogen-deficient state in a mammal, in particular bone loss, osteoporosis, cardiovascular diseases, cognitive disorders, senile dementia-Alzheimer's type, menopausal symptoms, including flushing and urogenital atrophy, dysmenorrhea, threatened or habitual abortion, dysfunctional uterine bleeding, acne, hirsutism, prostatic carcinoma, post-partum lactation, and the use of such compounds in a contraceptive method or as an aid in ovarian development.

BACKGROUND OF THE INVENTION

The osteopenia that accompanies the menopause continues to represent a major public health problem. Left unchecked, the cumulative loss of bone can potentially compromise the skeleton's structural integrity, resulting in painful and debilitating fractures of the wrist, spine and femur. Efforts to reduce the risk and incidence of fractures have focused on the development of therapies that conserve skeletal mass by inhibiting bone resorption. Among various treatment modalities, estrogen replacement therapy remains the preferred means to prevent the development of post menopausal osteoporosis (Lindsey R, Hart D M, MacClean A 1978, "The role of estrogen/progestogen in the management of the menopause", Cooke I D, ed, Proceedings of University of Sheffield symposium on the role of estrogen and progestogen in the management of the menopause, Lancaster, UK: MTP Press Ltd. pp. 9–25; Marshall D H, Horsmann A, Nordin BEC 1977, "The prevention and management of post-menopausal osteoporosis", Acta Obstet Gynecol Scand (Suppl) 65:49–56; Recker R R , Saville P D, Heaney R P 1977, "Effect of estrogen and calcium carbonate on bone loss in post-menopausal women", Ann Intern Med. 87:649–655, Nachtigall L E, Nachtigall R H, Nachtigall R D, Beckman E M 1979, "Estrogen replacement therapy", Obstet Gynecol. 53:277–281) and it is now accepted that estrogens significantly decrease fracture incidence and risk (Krieger N, Kelsey J L, Holford T R, O'Connor T 1982, "An epidemiological study of hip fracture in postmenopausal women", Am J Epidemiol. 116:141–148; Hutchinson T A, Polansky S M, Feinstein A R 1979, "Post-menopausal estrogens protect against fractures of hip and distal radius: A case-control study", Lancet 2:705–709; Paginini-Hill A, Ross R K, Gerkins V R, Henderson B E, Arthur M, Mack T M 1981, "Menopausal oestrogen therapy and hip fractures", Ann Intern Med. 95:28–31; Weiss N S, Ure C L, Ballard J H, Williams A R, Daling J R 1980, "Decreased risk of fractures on the hip and lower forearm with post-menopausal use of estrogen", N Eng J Med. 303:1195–1198).

While the beneficial actions of estrogen replacement therapy on the skeleton are clearly significant, there is also considerable evidence for a positive effect of estrogen on the cardiovascular system. Previous studies have attributed these actions to estrogen's effects on serum lipids, but recent data has now shown that in addition to the effects on the lipid profile, estrogen can also directly influence vessel wall compliance, reduce peripheral resistance and prevent atherosclerosis (Lobo R A 1990, "Cardiovascular implication of estrogen replacement therapy", Obstetrics and Gynaecology, 75:18S–24S; Mendelson M E, Karas R H 1994, "Estrogen and the blood vessel wall", Current Opinion in Cardiology, 1994(9):619–626). Based on available epidemiological data, the overall impact of these physiological and pharmacological actions of estrogen is an age independent reduction in cardiovascular mortality and morbidity in women (Kannel W H, Hjortland M, McNamara P M 1976 "Menopause and risk of cardiovascular disease: The Framingham Study", Ann Int Med, 85:447–552). Furthermore, a more recent analysis has concluded that post-menopausal estrogen replacement therapy reduces the risk of cardiovascular disease by approximately 50 percent (Stampfer M J, Colditz G A 1991, "Estrogen replacement therapy and coronary heart disease: a quantitative assessment of the epidemiological evidence", Preventive Medicine, 20:47–63.).

In addition to the positive effects of estrogen on bone and cardiovascular system, there are now data which indicate that the central nervous system can benefit from estrogen replacement therapy. Short term studies in human subjects have shown that increased levels of estrogen are associated with higher memory scores in post menopausal women (Kampen D L, Sherwin B B 1994, "Estrogen use and verbal memory in healthy postmenopausal women", Obstetrics and Gynecology, 83(6):979–983). Furthermore, the administration of exogenous estrogen to surgically post menopausal women specifically enhances short-term memory. Moreover, the effects of estrogen on cognition do not appear confined to short-term effects as epidemiological findings indicate that estrogen treatment significantly decreases the risk of senile dementia-Alzheimer's type in women (Paganini-Hill A, Henderson V W, 1994, "Estrogen deficiency and risk of Alzheimer's disease in women", Am J Epidemiol, 140:256–261; Ohkura T, Isse K, Akazawa K, Hamamoto M, Yoshimasa Y, Hagino N, 1995, "Long-term estrogen replacement therapy in female patients with dementia of the Alzheimer Type: 7 case reports", Dementia, 6:99–107). While the mechanism whereby estrogens enhance cognitive function is unknown, it is possible to speculate that the direct effects of estrogen on cerebral blood flow (Goldman H, Skelley Eb, Sandman C A, Kastin A J, Murphy S, 1976, "Hormones and regional brain blood flow", Pharmacol Biochem Rev. 5(suppl 1):165–169; Ohkura T, Teshima Y, Isse K, Matsuda H, Inoue T, Sakai Y, Iwasaki N, Yaoi Y, 1995, "Estrogen increases cerebral and cerebellar blood flows in postmenopausal women", Menopause: J North Am Menopause Soc. 2(1):13–18) and neuronal cell activities (Singh M, Meyer E M, Simpkins J W, 1995, "The effect of ovariectomy and estradiol replacement on brain-derived neurotrophic factor messenger ribonucleic acid expression in cortical and hippocampal brain regions of female Sprague-Dawley rats", Endocrinology, 136:2320–2324; McMillan P J, Singer C A, Dorsa D M, 1996, "The effects of ovariectomy and estrogen replacement on trkA and choline acetyltransferase mRNA expression in the basal forebrain of the adult female Sprague-Dawley rat", J Neurosci., 16(5):1860–1865) are potential effectors for these beneficial actions.

The therapeutic applications of naturally occurring estrogens and synthetic compositions demonstrating estrogenic activity alone or in combination are not limited to the chronic conditions described above. Indeed, the more traditional applications of estrogen therapies would include the following: relief of menopausal symptoms (i.e. flushing and urogenital atrophy); oral contraception; prevention of threatened or habitual abortion, relief of dysmenorrhea; relief of dysfunctional uterine bleeding; an aid in ovarian development; treatment of acne; diminution of excessive growth of body hair in women (hirsutism); treatment of prostatic carcinoma: and suppression of post-partum lactation [Goodman and Gilman, The Pharmacological Basis of Therapeutics (Seventh Edition) Macmillan Publishing Company, 1985, pages 1421–1423].

Even though the beneficial effects of estrogen replacement on a wide variety of organ systems and tissues appear indisputable, the dose and duration of estrogen therapy is also associated with an increased risk of endometrial hyperplasia and carcinoma. The use of concomitant cyclic progestins does reduce the risk of endometrial pathology, but this is achieved at the expense of the return of regular menstruation, a result that is objectionable to many patients. In addition to estrogen's stimulatory effect on the endometrium, there remains considerable controversy regarding reports of an association between long-term estrogen replacement and an increased risk of breast cancer (Bergkvist L, Adami H O, Persson I, Hoover R, Schairer C, 1989, "The risk of breast cancer after estrogen and estrogen-progestin replacement", N Eng J Med, 321:293–297; Colditz G A, Hankinson S E, Hunter D J, Willett W C, Manson J E, Stempfer M J, Hennekens C, Rosner B, Speizer F E, 1995, "The use of estrogens and progestins and the risk of breast cancer in postmenopausal women", N Eng J Med, 332(24):1589–1593). Furthermore, there are other side effects of estrogen replacement which, while they may not be life threatening, contraindicate estrogen's use and reduce patient compliance.

From the foregoing discussion it would appear that the availability of therapies which could mimic the beneficial actions of estrogen on the bone, cardiovascular system, and central nervous system without the undesirable side effects on uterus and breast, would essentially provide a "safe estrogen" which could dramatically influence the number of patients that would be able to benefit from estrogen replacement therapy. Therefore, in recognition of estrogen's beneficial effects on a number of body systems and disease conditions, there is a continuing need for the development of estrogen agonists which can selectively target different body tissues.

U.S. Pat. No. 2,986,563 discloses a class of cyclazines which has been disclaimed from the present application. However, there is no teaching or suggestion in this document that these compounds are active at the estrogen receptor.

DESCRIPTION OF THE INVENTION

The present invention provides compounds of formula I

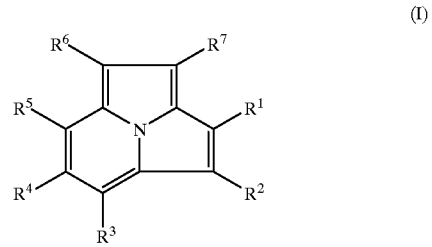

(I)

wherein
$R^1$ is phenyl optionally substituted with one or two substituents selected from halogen, OH, $NO_2$, CN, SH, $C_{1-4}$-alkyl optionally substituted with one to three halogen(s), $C_{1-4}$-alkoxy, $C_{1-4}$-alkylthio, benzyloxy, $OCOR^{36}$, $OCONHR^{36}$, $OCONR^{36}R^{37}$, $OSO_2NHR^{36}$ or $OSO_2NR^{36}R^{37}$ wherein $R^{36}$ and $R^{37}$ independently are $C_{1-6}$-alkyl; and
$R^2$ is H, $C_{1-4}$-alkyl, $C_{2-4}$-alkenyl or $C_{2-4}$-alkynyl; and
$R^3$ is H, OH, benzyloxy, $R^{10}$, $OR^{10}$, $COR^{10}$, $NHR^{10}$, $NR^{10}R^{11}$, NH—CO—$R^{10}$, $NR^{12}$—CO—$R^{10}$ or $R^{13}OR^{10}$ wherein $R^{12}$ is $C_{1-6}$-alkyl and $R^{13}$ is $C_{1-7}$-alkylene; and
$R^4$ is H, OH, benzyloxy, $R^{14}$, $OR^{14}$, $COR^{14}$, $NHR^{14}$, $NR^{14}R^{15}$, NH—CO—$R^{14}$, $NR^{16}$—CO—$R^{14}$ or $R^{17}OR^{14}$ wherein $R^{16}$ is $C_{1-6}$-alkyl and $R^{17}$ is $C_{1-7}$-alkylene; and
$R^5$ is H, OH, benzyloxy, $R^{18}$, $OR^{18}$, $COR^{18}$, $NHR^{18}$, $NR^{18}R^{19}$, NH—CO—$R^{18}$, $NR^{20}$—CO—$R^{18}$ or $R^{21}OR^{18}$ wherein $R^{20}$ is $C_{1-6}$-alkyl and $R^{21}$ is $C_{1-7}$-alkylene; and
$R^6$ is H, $R^{22}$, $OR^{22}$, $R^{23}OR^{22}$, $COR^{22}$, $COR^{24}$, $R^{25}OR^{26}$—$NR^{27}R^{28}$ or phenyl optionally substituted with $OR^{22}$, wherein $R^{23}$, $R^{25}$ and $R^{26}$ independently are $C_{1-7}$-alkylene, $R^{24}$ is phenyl optionally substituted with $OR^{22}$, and $R^{27}$ and $R^{28}$ together with the nitrogen atom form a saturated, partly saturated or unsaturated 4 to 6 membered heterocyclic ring containing one to four N, O or S atom(s) or a combination thereof; and
$R^7$ is H, $R^{29}$, $OR^{29}$, $R^{30}OR^{29}$, $COR^{29}$, $CONHR^{29}$, $COOR^{29}$, $CONR^{29}R^{29}$, $COR^{31}$, $R^{32}OR^{33}$—$NR^{34}R^{35}$ or phenyl optionally substituted with $OR^{29}$, wherein $R^{30}$, $R^{32}$ and $R^{33}$ independently are $C_{1-7}$-alkylene, $R^{31}$ is phenyl optionally substituted with $OR^{29}$, and $R^{34}$ and $R^{35}$ together with the nitrogen atom form a saturated, partly saturated or unsaturated 4 to 6 membered heterocyclic ring containing one to four N, O or S atom(s) or a combination thereof; and
wherein $R^{10}$, $R^{11}$, $R^{14}$, $R^{15}$, $R^{18}$, $R^{19}$, $R^{22}$ and $R^{29}$ independently are $C_{1-12}$-alkyl, $C_{2-12}$-alkenyl or $C_{2-12}$-alkynyl each of which is optionally substituted with OH, COOH, $COOR^{38}$, $CONHR^{39}$, $CONR^{40}$, $NHR^{41}$, $NR^{42}R^{43}$, $NHCOR^{44}$, $NHSO_2R^{45}$, $SOR^{46}$, $SO_2R^{47}$, $SONHR^{48}$, $SO_2NR^{49}R^{50}$ or a saturated, partly saturated or unsaturated 4 to 6 membered heterocyclic ring containing one to four N, O or S atom(s) or a combination thereof, wherein $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$ and $R^{50}$ independently are $C_{1-7}$-alkyl;
provided that $R^{22}$ is not $C_{1-7}$-alkyl optionally substituted with a piperidino ring and that $R^{29}$ is not $C_{1-7}$-alkyl optionally substituted with a piperidino ring when $R^3$ is H; and
provided that $R^5$ is not H, OH or benzyloxy when both $R^3$, $R^6$ and $R^7$ are H; and
provided that $R^3$ is not H or $C_{1-12}$-alkyl, or $R^4$ is not H or $C_{1-12}$-alkyl, or $R^5$ is not H, when $R^1$ is unsubstituted phenyl;
or geometric or optical isomers, pharmaceutically acceptable esters, ethers or salts thereof.

The general chemical terms used in the above formula have their usual meanings.

The term $C_{1-n}$-alkyl wherein n can be from 2 through 12, as used herein, includes straight-chained as well as branched alkyl groups having from one to the specified number of carbon atoms. Examples of such groups include, but are not limited to, methyl, ethyl, propyl, isopropyl, butyl, s-butyl, isobutyl, pentyl, neopentyl, hexyl, heptyl, tetradecyl, undecyl, neopentyl, 2,2-dimethylhexyl, 3-ethylnonyl, 3-butylheptyl and dodecyl and the like.

The term $C_{2-n}$-alkenyl wherein n can be from 3 through 12, as used herein, represents an olefinically unsaturated branched or straight group having from 2 to the specified number of carbon atoms and at least one double bond. Examples of such groups include, but are not limited to 1-propynyl, 2-propynyl, 1-butynyl, 2-butynyl, 1-pentenyl, 2-pentenyl and the like.

The term $C_{2-n}$-alkynyl wherein n can be from 3 through 12, as used herein, represents an unsaturated branched or straight group having from 2 to the specified number of carbon atoms and at least one triple bond. Examples of such groups include, but are not limited to, 1-propynyl, 2-propynyl, 1-butynyl, 2-butynyl, 1-pentenyl, 2-pentenyl and the like.

The term $C_{1-7}$-alkylene includes straight or branched alkylene groups. Examples of such include, but are not limited to, methylene, ethylene, trimethylene, tetramethylene, pentamethylene, hexamethylene, heptamethylene, propylene, ethylethylene and the like.

The term halogen means chloro, bromo, iodo and fluoro.

The term saturated, partly saturated or unsaturated 4 to 6 membered hetercyclic ring containing one to four N, O or S atom(s) or a combination thereof include preferred groups such as pyrrolidinly, pyrrolinyl, imidaxolyl, imidazolindinyl, pyrazolyl, pyraxolidinyl, pyraxolinyl, piperidyl, piperazinyl, pyrrol, 2H-pyrrol, triazolyl, pyridyl, pyrazinyl, pyrimidinyl, pyridazinyl, morpholino, thiomorpholino, isothiazolyl, isoxazolyl, oxazolyl, oxadiazolyl, thiadiazolyl, thiazolyl.

The compounds of this invention are new estrogen agonists and are useful for prevention and treatment of osteoporosis; the prevention and treatment of cardiovascular disease; treatment and prevention of physiological disorders associated with an excess of neuropeptide Y (e.g. obesity, depression, etc.); and for regulation of glucose metabolism in e.g. non-insulin dependent diabetes melitus; and the prevention and treatment of senile dementia-Alzheimer's type in women. In addition, these estrogen agonists are useful for oral contraception; relief of menopausal symptoms (e.g. hot flushes, urogenital atrophy, depression, mania, schizophrenia, etc.); incontinence; prevention of threatened or habitual abortion; relief of dysmenorrhea; relief of dysfunctional uterine bleeding; an aid in ovarian development; treatment of acne; diminution of excessive growth of body hair in women (hirsutism); treatment of prostatic carcinoma; and the suppression of post-partum lactation. These agents also lower serum cholesterol and have a beneficial effect on plasma lipid profiles.

While the compounds of this invention are estrogen agonists in bone and cardiovascular tissues, they are also capable of acting as antiestrogens in other estrogen target organs. For example, these compounds can act as antiestrogens in breast tissue and the colon and therefore would be useful for the prevention and treatment of estrogen-dependent cancers such as breast cancers and colon cancers.

The term "treatment" includes treatment, prevention and prophylaxis of the above mentioned diseases/indications/conditions or alleviation of the characteristic symptoms of such diseases/indications/conditions.

The preferred compounds of this invention are those in which:

$R^1$ is phenyl optionally substituted with OH;
$R^2$ is $C_{1-4}$-alkyl;
$R^3$ is H or $R^{13}OR^{10}$, preferably H or $CH_2OR^{10}$, wherein $R^{10}$ and $R^{13}$ are as defined above;
$R^4$ is H, OH or $OCH_3$;
$R^5$ is H, OH or $OCH_3$;
$R^6$ is H, $R^{22}$ or $R^{23}OR^{22}$, preferably H, $R^{22}$ or $CH_2OR^{22}$, wherein $R^{22}$ and $R^{23}$ are as defined above;
$R^7$ is H, $R^{29}$, $R^{30}OR^{29}$ is phenyl substituted with $OR^{29}$, preferably H, $R^{29}$, $CH_2OR^{29}$ or phenyl substituted with $OR^{29}$, wherein $R^{29}$ and $R^{30}$ are as defined above.

The most preferred compounds are the following:
2-(4-Benzyloxyphenyl)-1-ethyl-4-hydroxymethylpyrrolo[2,1,5-cd]indolizine,
2-(4-Benzyloxyphenyl)-1-ethyl-4-((2-piperidinoethoxy)methyl)pyrrolo[2,1,5-cd]indolizine,
2-(4-Benzyloxyphenyl)-1-ethyl-4-methoxymethylpyrrolo[2,1,5-cd]indolizine,
2-(4-Benzyloxyphenyl)-1-ethyl-4-propoxymethylpyrrolo[2,1,5-cd]indolizine,
2-(4-Benzyloxyphenyl)-4-((3-dimethylaminopropoxy)methyl)-1-ethylpyrrolo[2,1,5-cd]indolizine,
2-(4-Benzyloxyphenyl)-4-((2-diethylaminoethoxy)methyl)-1-ethylpyrrolo[2,1,5-cd]indolizine,
2-(4-Benzyloxyphenyl)-1-ethyl-4-((2-pyrrolidinoethoxy)methyl)pyrrolo[2,1,5-cd]indolizine,
2-(4-Benzyloxyphenyl)-1-ethyl-4-((2-(morpholine-4-yl)ethoxy)methyl)pyrrolo[2,1,5-cd]indolizine,
2-(4-Benzyloxyphenyl)-4-((2-dimethylaminoethoxy)methyl)-1-ethylpyrrolo[2,1,5-cd]indolizine,
2-(4-Benzyloxyphenyl)-1-ethyl-4-((3-piperidinopropoxy)methyl)pyrrolo[2,1,5-cd]indolizine,
6-[2-(4-Benzyloxyphenyl)-1-ethylpyrrolo[2,1,5-cd]indolizine-4-ylmethoxy]hexanoic acid dimethylamide,
1-Ethyl-2-(4-hydroxyphenyl)-4-((2-piperidinoethoxy)methyl)pyrrolo[2,1,5-cd]indolizine,
1-Ethyl-2-(4-hydroxyphenyl)-4-methoxymethylpyrrolo[2,1,5-cd]indolizine,
1-Ethyl-2-(4-hydroxyphenyl)-4-propoxymethylpyrrolo[2,1,5-cd]indolizine,
4-((3-Dimethylaminopropoxy)methyl)-1-ethyl-2-(4-hydroxyphenyl)pyrrolo[2,1,5-cd]indolizine,
4-((2-Diethylaminoethoxy)methyl)-1-ethyl-2-(4-hydroxyphenyl)pyrrolo[2,1,5-cd]indolizine
1-Ethyl-2-(4-hydroxyphenyl)-4-((2-pyrrolidinoethoxy)methyl)pyrrolo[2,1,5-cd]indolizine,
1-Ethyl-2-(4-hydroxyphenyl)-4-((2-(morpholine-4-yl)ethoxy))methyl)pyrrolo[2,1,5-cd]indolizine,
4-((2-Dimethylaminoethoxy)methyl)-1-ethyl-2-(4-hydroxyphenyl)pyrrolo[2,1,5-cd]indolizine,
1-Ethyl-2-(4-hydroxyphenyl)-4-((3-piperidinopropoxy)methyl)pyrrolo[2,1,5-cd]indolizine,
6-[1-ethyl-2-(4-hydroxyphenyl)pyrrolo[2,1,5-cd]indolizin-4-ylmethoxy]hexanoic acid dimethylamide,
3-(4-Benzyloxyphenyl)-4-ethyl-pyrrolo[2,1,5-cd]indolizine-1-carboxylic acid dimethylamide,
5-Benzyloxy-2-(4-benzyloxyphenyl)-1-ethyl-3-hydroxymethylpyrrolo[2,1,5-cd]indolizine,
1-Ethyl-3-hydroxymethyl-2-(4-methoxyphenyl)pyrrolo[2,1,5-cd]indolizine,
2-(4-Benzyloxyphenyl)-3-hydroxymethylpyrrolo[2,1,5-cd]indolizine,
5-Benzyloxy-1-ethyl-3-hydroxymethyl-2-phenylpyrrolo[2,1,5-cd]indolizine, 2-(4-Benzyloxyphenyl)-1-ethyl-3-hydroxymethylpyrrolo[2,1,5-cd]indolizine,
5-Benzyloxy-2-(4-benzyloxyphenyl)-1-ethyl-3-((2-piperidinoethoxy)methyl)pyrrolo[2,1,5-cd]indolizine,
5-Benzyloxy-2-(4-benzyloxyphenyl)-1-ethyl-3-((3-piperidinopropoxy)methyl)pyrrolo[2,1,5-cd]indolizine,
5-Benzyloxy-2-(4-benzyloxyphenyl)-1-ethyl-3-((6-piperidinohexyloxy)methyl)pyrrolo[2,1,5-cd]indolizine,
5-Benzyloxy-2-(4-benzyloxyphenyl)-1-ethyl-3-((7-piperidinoheptyloxy)methyl)pyrrolo[2,1,5-cd]indolizine,
5-Benzyloxy-2-(4-benzyloxyphenyl)-1-ethyl-3-((8-piperidinooctyloxy)methyl)pyrrolo[2,1,5-cd]indolizine,
5-Benzyloxy-1-ethyl-2-phenyl-3-((2-piperidinoethoxy)methyl)pyrrolo[2,1,5-cd]indolizine,
5-Benzyloxy-1-ethyl-2-phenyl-3-((3-piperidinopropoxy)methyl)pyrrolo[2,1,5-cd]indolizine,
2-(4-Benzyloxyphenyl)-1-ethyl-3-((2-piperidinoethoxy)methyl)pyrrolo[2,1,5-cd]indolizine,
5-Benzyloxy-2-(4-benzyloxyphenyl)-3-((5-chloropentyloxy)methyl)-1-ethylpyrrolo[2,1,5-cd]indolizine,
5-Benzyloxy-2-(4-benzyloxyphenyl)-3-((4-chlorobutoxy)methyl)-1-ethylpyrrolo[2,1,5-cd]indolizine,
5-Benzyloxy-2-(4-benzyloxyphenyl)-1-ethyl-3-((5-methoxypentoxy)methyl)pyrrolo[2,1,5-cd]indolizine,
2-(4-Benzyloxyphenyl)-1-ethyl-3-methoxymethylpyrrolo[2,1,5-cd]indolizine,
1-Ethyl-3-methoxymethyl-2-(4-methoxyphenyl)pyrrolo[2,1,5-cd]indolizine,
2-(4-Benzyloxyphenyl)-3-methoxymethylpyrrolo[2,1,5-cd]indolizine,
5-Benzyloxy-2-(4-benzyloxyphenyl)-1-ethyl-3-methoxymethylpyrrolo[2,1,5-cd]indolizine,
5-Benzyloxy-2-(4-benzyloxyphenyl)-1-ethyl-3-((5-piperidinopentoxy)methyl)pyrrolo[2,1,5-cd]indolizine,
5-Benzyloxy-2-(4-benzyloxyphenyl)-1-ethyl-3-((4-piperidinobutoxy)methyl)pyrrolo[2,1,5-cd]indolizine,
5-Benzyloxy-2-(4-benzyloxyphenyl)-1-ethyl-3-((4-pyrrolidinobutoxy)methyl)pyrrolo[2,1,5-cd]indolizine,
5-Benzyloxy-2-(4-benzyloxyphenyl)-3-((but-3-enyloxy)methyl)-1-ethylpyrrolo[2,1,5-cd]indolizine,
1-Ethyl-5-hydroxy-2-(4-hydroxyphenyl)-3-((8-piperidinooctyloxy)methyl)pyrrolo[2,1,5-cd]indolizine,
1-Ethyl-5-hydroxy-2-(4-hydroxyphenyl)-3-methoxymethylpyrrolo[2,1,5-cd]indolizine,
1-Ethyl-2-(4-hydroxyphenyl)-3-((2-piperidinoethoxy)methyl)pyrrolo[2,1,5-cd]indolizine,
1-Ethyl-5-hydroxy-2-(4-hydroxyphenyl)-3-((2-piperidinoethoxy)methyl)pyrrolo[2,1,5-cd]indolizine,
1-Ethyl-5-hydroxy-2-(4-hydroxyphenyl)-3-((3-piperidinopropoxy)methyl)pyrrolo[2,1,5-cd]indolizine,
1-Ethyl-5-hydroxy-2-phenyl-3-((2-piperidinoethoxy)methy)pyrrolo[2,1,5-cd]indolizine,
1-Ethyl-5-hydroxy-2-phenyl-3-((3-piperidinopropoxy)methyl)pyrrolo[2,1,5-cd]indolizine,
1-Ethyl-5-hydroxy-2-(4-hydroxyphenyl)-3-((5-methoxypentoxy)methyl)pyrrolo[2,1,5-cd]indolizine,
1-Ethyl-2-(4-hydroxyphenyl)-3-methoxymethylpyrrolo[2,1,5-cd]indolizine,
1-Ethyl-5-hydroxy-2-(4-hydroxyphenyl)-3-((6-piperidinohexyloxy)methyl)pyrrolo[2,1,5-cd]indolizine,
2-(4-Hydroxyphenyl)-3-methoxymethylpyrrolo[2,1,5-cd]indolizine,
1-Ethyl-5-hydroxy-2-(4-hydroxyphenyl)-3-((5-piperidinopentoxy)methyl)pyrrolo[2,1,5-cd]indolizine,
1-Ethyl-3-hydroxymethyl-2-(4-hydroxyphenyl)pyrrolo[2,1,5-cd]indolizine,
3-Hydroxymethyl-2-(4-hydroxyphenyl)pyrrolo[2,1,5-cd]indolizine,
1-Ethyl-5-hydroxy-3-hydroxymethyl-2-(4-hydroxyphenyl)pyrrolo[2,1,5-cd]indolizine,
2-[(2-Dimethylaminoethyl)methylcarbamoyl]-4-ethyl-6-methoxy-3-(4-methoxyphenyl)-pyrrolo[2,1,5-cd]indolizine-1-carboxylic acid,
2-[(2-Dimethylaminoethyl)methylcarbamoyl]-4-ethyl-3-(4-methoxyphenyl)pyrrolo[2,1,5-cd]indolizine-1-carboxylic acid,
2-[(2-Dimethylaminoethyl)methylcarbamoyl]-4-ethyl-6-methoxy-3-(4-methoxyphenyl)pyrrolo[2,1,5-cd]indolizine,
2-[(2-Dimethylaminoethyl)methylcarbamoyl]-4-ethyl-3-(4-methoxyphenyl)pyrrolo[2,1,5-cd]indolizine,
2-[(2-Dimethylaminoethyl)methylcarbamoyl]-4-ethyl-3-(4-hydroxyphenyl)-6-methoxypyrrolo[2,1,5-cd]indolizine,
2-[(2-Dimethylaminoethyl)methylcarbamoyl]-4-ethyl-3-(4-hydroxyphenyl)pyrrolo[2,1,5-cd]indolizine,
3-Dimethylaminomethyl-1-ethyl-2-(4-hydroxyphenyl)pyrrolo[2,1,5-cd]indolizine,
2-(4-Benzyloxyphenyl)-3-dimethylaminomethyl-1-ethylpyrrolo[2,1,5-cd]indolizine,
3-Benzoyl-2-(4-benzyloxyphenyl)-1-ethylpyrrolo[2,1,5-cd]indolizine,
3-Benzyl-1-ethyl-2-(4-hydroxyphenyl)pyrrolo[2.1.5-cd]indolizine,
2-(4-Acetoxyphenyl)-3-benzyl-1-ethylpyrrolo[2,1,5-cd]indolizine,
1-Ethyl-5-hydroxy-2-(4-hydroxyphenyl)-4-(1-oxopropyl)pyrrolo[2,1,5-cd]indolizine,
5-Acetoxy-2-(4-acetoxyphenyl)-1-ethyl-4-(1-oxopropyl)pyrrolo[2,1,5-cd]indolizine,
4-Benzoyl-1-ethyl-2-(4-methoxyphenyl)pyrrolo[2,1,5-cd]indolizine,
4-(4-Benzyloxybenzoyl)-1-ethyl-2-(4-methoxyphenyl)pyrrolo[2,1,5-cd]indolizine,
1-Ethyl-2-(4-methoxyphenyl)-4-[4-(2-piperidinoethoxy)phenyl]pyrrolo[2,1,5-cd]indolizine,
1-Ethyl-2-(4-hydroxyphenyl)-4-[4-(2-piperidinoethoxy)phenyl]pyrrolo[2,1,5-cd]indolizine,
4-Acetyl-1-ethyl-7-benzyloxy-2-(4-benzyloxyphenyl)pyrrolo[2,1,5-cd]indolizine,
4-Acetyl-1-ethyl-7-hydroxy-2-(4-hydroxyphenyl)pyrrolo[2,1,5-cd]indolizine,
4-Acetyl-2-(4-benzyloxyphenyl)-1-ethyl-7-hydroxymethylpyrrolo[2,1,5-cd]indolizine,
4-Acetyl-1-ethyl-7-hydroxymethyl-2-(4-hydroxyphenyl)pyrrolo[2,1,5-cd]indolizine,
3-(4-Benzyloxyphenyl)-4-ethyl-5-hydroxymethylpyrrolo[2,1,5-cd]indolizine-1,2-dicarboxylic acid,
2-(4-Benzyloxyphenyl)-1-ethyl-7-hydroxymethylpyrrolo[2,1,5-cd]indolizine,
1-Ethyl-7-hydroxymethyl-2-(4-hydroxyphenyl)pyrrolo[2,1,5-cd]indolizine,
3-(4-Benzyloxyphenyl)-4-ethyl-5-hydroxymethylpyrrolo[2,1,5-cd]indolizine-1-carboxylic acid,
2-(4-Benzyloxyphenyl)-1-ethyl-7-((2-pyrrolidinoethoxy)methyl)pyrrolo[2,1,5-cd]indolizine,
2-(4-Benzyloxyphenyl)-1-ethyl-7-((2-piperidinoethoxy)methyl)pyrrolo[2,1,5-cd]indolizine,
2-(4-Benzyloxyphenyl)-1-ethyl-7-((3-dimethylaminopropoxy)methyl)pyrrolo[2,1,5-cd]indolizine,
2-(4-Benzyloxyphenyl)-1-ethyl-7-((3-piperidinopropoxy)methyl)pyrrolo[2,1,5-cd]indolizine,
1-Ethyl-2-(4-hydroxyphenyl)-7-((2-pyrrolidinoethoxy)methyl)pyrrolo[2,1,5-cd]indolizine, 1-Ethyl-2-(4-hydroxyphenyl)-7-((2-piperidinoethoxy) methyl)pyrrolo[2,1,5-cd]indolizine,
1-Ethyl-2-(4-hydroxyphenyl)-7-((3-dimethylaminopropoxy)methyl)pyrrolo[2,1,5-cd] indolizine,
1-Ethyl-2-(4-hydroxyphenyl)-7-((3-piperidinopropoxy) methyl)pyrrolo[2,1,5-cd]indolizine,
5-Acetoxymethyl-3-(4-benzyloxyphenyl)-2-dimethylcarbamoylpyrrolo[2,1,5-cd]indolizine-1-carboxylic acid,
Dimethyl 3-(4-benzyloxyphenyl)-5-hydroxymethylpyrrolo [2,1,5-cd]indolizine-1,2-dicarboxylate,
4-Acetyl-1-ethyl-2-(4-hydroxymethylphenyl)pyrrolo[2,1,5-cd]indolizine,
4-Ethyl-3-(4-hydroxymethylphenyl)pyrrolo[2,1,5-cd] indolizine-1,2-dicarboxylic acid,
1-Ethyl-4-hydroxymethyl-2-(4-methoxyphenyl)pyrrolo[2,1, 5-cd]indolizine,
1-Ethyl-2-(4-methoxyphenyl)-4-((2-piperidinoethoxy) methyl)pyrrolo[2,1,5-cd]indolizine,
Dimethyl 3-(4-benzyloxyphenyl)-4-ethyl-7-methoxypyrrolo [2,1,5-cd]indolizine-1,2-dicarboxylate,
3-(4-Benzyloxyphenyl)-4-ethyl-7-methoxypyrrolo[2,1,5-cd]indolizine-1,2-dicarboxylic acid,
2-(4-Benzyloxyphenyl)-1-ethyl-5-methoxypyrrolo[2,1,5-cd]indolizine,
1-Ethyl-2-(4-hydroxyphenyl)-5-methoxypyrrolo[2,1,5-cd] indolizine,
Methyl 7-acetylamino-3-(4-benzyloxyphenyl)-4-ethylpyrrolo[2,1,5-cd]indolizine-1-carboxylate,
7-Acetylamino-3-(4-benzyloxyphenyl)-4-ethylpyrrolo[2,1, 5-cd]indolizine-1-carboxylic acid,
5-Acetylamino-2-(4-benzyloxyphenyl)-1-ethylpyrrolo[2,1, 5-cd]indolizine,
5-Acetylamino-1-ethyl-2-(4-hydroxyphenyl)pyrrolo[2,1,5-cd]indolizine,
5-Amino-2-(4-benzyloxyphenyl)-1-ethylpyrrolo[2,1,5-cd] indolizine,
5-Amino-1-ethyl-2-(4-hydroxyphenyl)pyrrolo[2,1,5-cd] indolizine,
1-Ethyl-6-hydroxymethyl-2-(4-hydroxyphenyl)-3-[4-(2-piperidinoethoxy)phenyl]pyrrolo-[2,1,5-cd]indolizine,
2-(4-Hydroxyphenyl)-1-(6-piperidinohexyl)pyrrolo[2,1,5-cd]indolizine,
1-(6-Carboxyhexyl)-2-(4-hydroxyphenyl)pyrrolo[2,1,5-cd] indolizine,
1-Ethyl-2-(3-fluoro-4-hydroxyphenyl)-3-(1-oxo-3-piperidinopropyl)pyrrolo[2,1,5cd]indolizine,
1-Ethyl-2-[4-hydroxy-2-(1-oxo-3-piperidinopropyl)phenyl] pyrrolo[2,1,5-cd]indolizine,
2-[2-(2-Dimethylaminoethoxy)phenyl]-4-hydroxy]phenyl-1-ethylpyrrolo[2,1,5-cd]indolizine,
2-[(4-Hydroxymethyl)phenyl]-1-methylethylpyrrolo[2,1,5-cd]indolizine,
N-[2-(4-Hydroxyphenyl)-1-ethyl-pyrrolo[2,1,5-cd] indolizin-5-yl]-butyramide;
or geometric or optical isomers, pharmaceutically acceptable esters, ethers or salts thereof.

The preparation of cycl[3,2,2]azines (i.e. pyrrolo[2,1,5-cd]indolizines) is well described in Advances in heterocyclic chemistry Vol. 22, p. 321–365, 1978, Title: Cyclazines and related N-bridged Annulenes, and a general review is given in Synthesis, Vol. 4, p. 209–36, 1976, Title: Methods for the Construction of the Indolizine Nucleus". Preparation of the intermediate indolizines is also well described in the literature, i.a. in Russian Chemical Reviews, 44 (9), 1975; Title: Indolizines.

The invention is furthermore concerned with a general method for the preparation of compounds of formula (I) comprising the steps of:
a) reacting a compound of the formula (II)

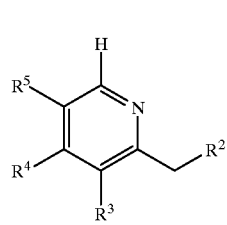

(II)

wherein $R^2$–$R^5$ are as defined above
with a compound of the formula (III)

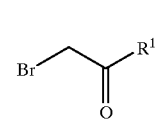

(III)

wherein $R^1$ is as defined above,
in a suitable solvent, preferably acetone, acetonitrile or tetrahydrofuran, to form a compound of the formula (IV)

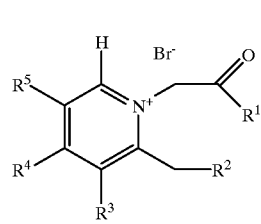

(IV)

wherein $R^1$–$R^5$ are as defined above;
b) reacting a compound of the formula (IV) with aqueous sodium hydrogen carbonate solution to form a compound of the formula (V)

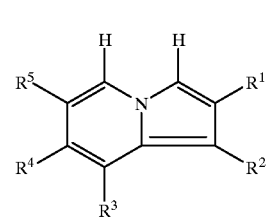

(V)

wherein $R^1$–$R^5$ are as defined above;
c) reacting a compound of the formula (V) with a compound of the formula (VI)

(VI)

wherein $R^6$ and $R^7$ independently are H, $COOCH_3$ or $COCH_3$, provided that at least one of $R^6$ and $R^7$ is $COOCH_3$ or $COCH_3$.
in a suitable solvent, preferably toluene, and oxidizing the dihydro intermediate with 2,3-dichloro-5,6-dicyano-1,4-benzoquinone (DDQ) to form a compound of the formula (I) wherein $R^1$–$R^7$ are as defined above;

d) hydrolyzing a compound of formula (I) wherein $R^6$ and $R^7$ are independently COOCH3, with a suitable base, preferably potassium hydroxide in methanol, to give a compound of formula (I), wherein $R^6$ and $R^7$ are independently COOH and $R^1$–$R^5$ are as defined above;

e) decarboxylating a compound of formula (I), wherein $R^6$ and $R^7$ are independently COOH, preferably by reaction with copper in quinoline, to give a compound of formula (I), wherein $R^6$ and $R^7$ are H and $R^1$–$R^5$ are as defined above.

The invention furthermore relates to a method of synthesizing compounds of formula (I), which method comprises the steps of:

a) reacting a compound of formula (VII)

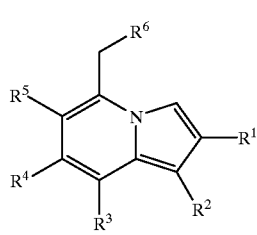

(VII)

wherein $R^1$–$R^6$ are as defined above,
with n-butyllithium followed by the N,N-dimethylamide (VIII)

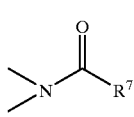

(VIII)

wherein $R^7$ is as defined above,
followed by hydrolysis to form a compound (IX)

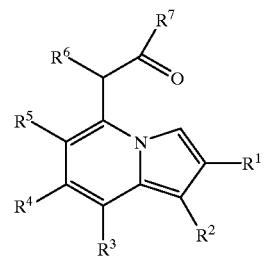

(IX)

wherein $R^1$–$R^7$ are as defined above; and b) ring closing the compound (IX) by treatment with acetic acid to form a compound of formula (I),
wherein $R^1$–$R^7$ are as defined above.

The invention furthermore relates to a method of synthesizing compounds of formula (I), which comprises the steps of:

a) reacting a compound of formula (I), wherein $R^6$ and $R^7$ are hydrogen, with bromine in acetic acid to give a compound of formula (I), wherein $R^1$–$R^5$ are as defined above, $R^6$ is bromine and $R^7$ is hydrogen, b) reacting a compound of formula (I), wherein $R^6$ is bromine, with a phenylboronic acid under suitable Suzuki cross coupling conditions in the presence of a palladium(0) catalyst, preferably tetrakistriphenylphosphine palladium (0), to give a compound of formula (I), wherein $R^6$ is a phenyl or substituted-phenyl group, $R^1$–$R^5$ are as defined above and $R^7$ is hydrogen.

The invention furthermore relates to a method of synthesizing compounds of formula (I), which method comprises the steps of:

a) reacting a compound of formula I, wherein $R^6$ and $R^7$ are COOH, with a dehydrating agent, preferably acetic acid anhydride in pyridine, to form a compound of formula (X)

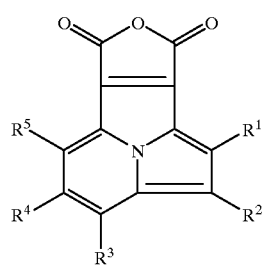

(X)

wherein $R^1$–$R^5$ are as defined above;

b) reacting a compound of formula (X), wherein $R^1$–$R^5$ are as defined above, with an alcohol in an appropriate solvent, preferably ethanol in pyridine, to form a compound of formula (XI),

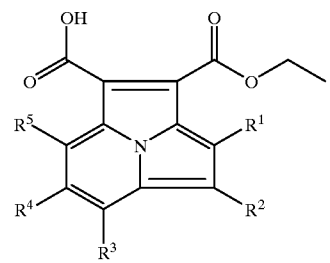

(XI)

wherein $R^1$–$R^5$ are as defined above;

c) decarboxylating a compound of formula (XI), wherein $R^1$–$R^5$ are as defined above, preferably by reaction with copper in quinoline, to give a compound of formula (I), wherein $R^6$ is H, $R^7$ is COOCH$_2$CH$_3$, and $R^1$–$R^5$ are as defined above;

d) reducing a compound of formula (I), wherein $R^6$ is H, $R^7$ is COOCH$_2$CH$_3$, and $R^1$–$R^5$ are as defined above, with a suitable hydride reagent, preferably lithium aluminium hydride, to form a compound of formula (I), wherein $R^6$ is H, $R^7$ is CH$_2$OH, and $R^1$–$R^5$ are as defined above.

The invention furthermore relates to a method of synthesizing compounds of formula (I), which method comprises the steps of:

a) reacting a compound of formula (X), wherein $R^1$–$R^5$ are as defined above, with a primary amine in an appropriate solvent, preferably pyridine, to form a compound of formula (XII),

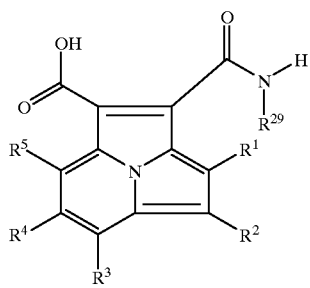

(XII)

wherein $R^{29}$ and $R^1–R^5$ are as defined above;

b) decarboxylating a compound of formula (XII), wherein $R^{29}$ and $R^1–R^5$ are as defined above, preferably by reaction with copper in quinoline, to give a compound of formula (I), wherein $R^6$ is H, $R^7$ is $CONHR^{29}$, wherein $R^{29}$ and $R^1–R^5$ are as defined above.

The invention furthermore relates to a method of synthesizing compounds of formula (I), which method comprises the steps of:

a) reacting a compound of formula (X), wherein $R^1–R^5$ are as defined above, with a secondary amine in an appropriate solvent, preferably pyridine, to form a compound of formula (XIII),

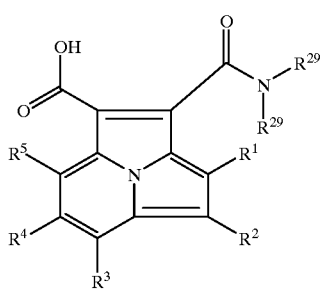

(XIII)

wherein $R^{29}$ and $R^1–R^5$ are as defined above;

b) decarboxylating a compound of formula (XIII), wherein $R^{29}$ and $R^1–R^5$ are as defined above, preferably by reaction with copper in quinoline, to give a compound of formula (I), wherein $R^6$ is H, $R^7$ is $CONR^{29}R^{29}$, wherein $R^{29}$ and $R^1–R^5$ are as defined above.

The invention furthermore relates to a method of synthesizing compounds of formula (I), which method comprises the steps of:

a) reducing a compound of formula (XIV)

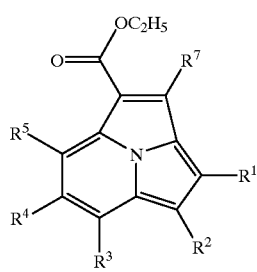

(XIV)

wherein $R^1–R^7$ are as defined above,
with a suitable hydride reducing agent to form a compound of formula (XV)

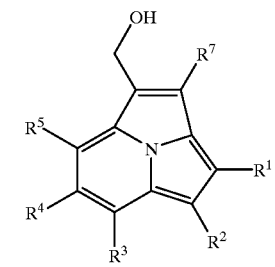

(XV)

wherein $R^1–R^7$ are as defined above;

b) alkylating a compound of the formula (XV) with an appropriate electrophile, preferentially an alkylhalogenide of the formula $R^{51}$-Hlg, wherein Hlg is Cl, Br or I
and $R^{51}$ is as defined above for $R^{10}$, $R^{11}$, $R^{15}$, $R^{18}$, $R^{19}$, $R^{22}$, and $R^{29}$ to form a compound of formula (I), wherein $R^1–R^7$ and $R^{51}$ are as defined above.

Any compound of formula (I), wherein $R^1–R^7$ are as defined above and wherein any R-substituent is or contains a methoxy group, may be deprotected with boron tribromide in methylene chloride or with pyridinium chloride fusion, to give a compound of formula (I), wherein said methoxy group is transformed to a hydroxy group. Any compound of formula (I) wherein $R^1–R^7$ are as defined above and wherein any R-substituent is or contains a benzyloxy group, may be deprotected using a palladium on carbon catalyst and hydrogen gas, to give a compound of formula (I), wherein said benzyloxy group is transformed to a hydroxy group.

Examples of pharmaceutically acceptable salts include inorganic and organic acid addition salts such as hydrochloride, hydrobromide, sulfate, phosphate, acetate, fumarate, maleate, citrate, lactate, tartrate, oxalate, or similar pharmaceutically acceptable inorganic or organic acid addition salts, and include the pharmaceutically acceptable salts listed in *Journal of Pharmaceutical Science*, 66, 2 (1977) which are known to the skilled artisan. The compounds of this invention may form solvates with standard low molecular weight solvents using methods known to the skilled artisan.

In Vitro Estrogen Receptor Binding Assay

An in vitro receptor binding assay was used to determine the estrogen receptor binding affinity of the compounds of this invention. This assay measures the ability of the compounds of this invention to displace $^3H$-17β-estradiol (17β-E2), from estrogen receptor (ER) obtained from rabbit uterus. Experimentally, the ER rich cytosol from rabbit uterine tissue is diluted with ER poor cytosol isolated from rabbit muscle to achieve approximately 20–25% maximal binding of 0.5 nM $^3H$-17β-E2. For each assay, fresh aliquots of cytosol are thawed on the day of analysis and diluted with assay buffer to ca. 3 mg cytosol protein/ml. The assay buffer (PB) is as follows: 10 mM $K_2HPO_4/KH_2PO_4$, 1.5 mM $K_2EDTA$, 10 mM monothioglycerol, 10 mM $Na_2MoO_4.2H_2O$, 10% glycerol (v/v); pH 7.5. Radio-inert 17β-E2 is obtained from Sigma.

Test solutions are prepared in appropriate solvents (ethanol or DMSO) at a concentration of 8×10-3 M and serial dilutions prepared with PB or DMSO. Aliquots of 10 μl are incubated in duplicate for each concentration tested in microtitre plates to which have been added 20 μl $^3H$-17β-E2 (assay concentration equals 0.4 nM) and 50 μl cytosol. For control samples as well as maximal binding sample, 10 μl PB is added in lieu of test compound.

Following an 18–20 hr incubation at 4° C. the reaction is terminated with 100 μl DCC slurry [0.5% activated charcoal (Sigma) and 0.005% Dextran T70 (Pharmacia) in PB] added to each sample and incubated with continuous shaking for 15 min at 4° C. DCC background counts are assessed using 50 μl of 0.3% BSA in PB in lieu of cytosol.

To separate bound and free $^3$H-17β-E2, Titertek plates are centrifuged for 10 min (800×g) at 4° C. and aliquots of 100 μl are removed from each sample for scintillation counting using Optiflour scintillation liquid. Standard and control samples are incubated in quadruplicate, while test compounds are incubated in duplicate. The mean counts per minute (cpm) in each sample is calculated, background (DCC) is subtracted, and the percent of maximal 3H-17β-E2 binding is determined. Individual cpm's are plotted against their respective concentrations of test compound (logarithmic scale), and the IC50 expressed as the compound concentration required to displace 50% of the maximal binding.

Bone Mineral Density

Bone mineral density (BMD) as a measure of bone mineral content (BMC) accounts for greater than 80% of a bone's strength. The loss of BMD with aging and the accelerated loss following the menopause reduce the strength of the skeleton and render specific sites more susceptible to fracture; i.e. most notably the spine, wrist and hip. True bone density can be measured gravimetrically using Archimede's Principle (an invasive technique). The BMD can also be measured non-invasively using dual energy x-ray absorptiometry (DEXA). In our laboratory, we have utilized a gravimetric method to evaluate changes in BMD due to estrogen deficiency in ovariectomized rodents. Following ovariectomy (the surgical removal of the ovaries), the animals are treated with vehicle, 17β-E2 as a positive control, and/or other estrogen agonists. The objective of these investigations is to evaluate the ability of the compounds of this invention to prevent bone loss in rodent models of human disease.

Female Sprague-Dawley rats (ca. 3 to 5 months old), or female Swiss-Webster mice (ca. 3 to 5 months old) underwent bilateral ovariectomy or sham surgery. Following recovery from anesthesia the animals are randomized to the following groups, minimum of 8 animals per group;

sham animals treated with vehicle;

ovariectomized animals teated with vehicle;

ovariectomized animals treated with 25 μg estradiol/kg; and ovariectomized animals treated with 200 μg/kg of test compound.

All compounds are weighted and dissolved in vehicle solvent in sterile saline and the animals are treated daily via subcutaneous injections for 35 days. At the conclusion of the 35 day protocol, the animals are sacrificed and the femora are excised and cleaned of adherent soft tissue. In rats, the distal 1 cm of the defleshed femora are removed with a diamond wheel cut-off saw and fixed in 70% ethyl alcohol (in mice the distal 0.5 cm are removed and fixed). Following fixation in 70% ethyl alcohol (EtOH) an automated tissue processor was used to dehydrate the bone specimens in an ascending series of alcohol to 100%. The dehydration program was followed by defatting in chloroform and rehydration in distilled water. All automated tissue processing occurred under vacuum. The hydrated bones were weighed in air and weighed while suspended in water on a Mettler balance equipped with a density measurement kit. The weight of each sample in air is divided by the difference between the air weight and the weight in water to determine total bone density; i.e. organic matrix plus mineral per unit volume of tissue. After the determination of total bone density the samples are ashed overnight in a muffle furnace at 600° C. The mineral density can then be determined by dividing the ash weight of each sample by the tissue volume (i.e. air weight—weight suspended in water). The mean bone densities (total and mineral bone densities) are calculated for each group and statistical differences from the vehicle-treated and estrogen-treated controls are determined using compouterized statistical programs.

Cholesterol Lowering Activity

The effects of the compounds of the present invention on the serum levels of total cholesterol were measured either in blood samples taken from the animals in the bone density studies described above or from ovariectomized female rats or mice that had been treated with compound for a period of not less than 28 days. In each type of experiment, blood from teated animals was collected via cardiac puncture and placed in a tube containing 30 μl of 5% EDTA/1 ml of blood. Following centrifugation at 2500 rpm for 10 minutes at 20° C. the plasma was removed and stored at −20° C. until assayed. Cholesterol was measured using a standard enzymatic determination kit purchased from Sigma Diagnostics (Kit No. 352).

The compounds of the invention are effective over a wide dosage range. For example, in the treatment of adult humans, dosages from about 0.05 to about 100 mg, preferably from about 0.1 to about 100 mg, per day may be used. A most preferable dosage is about 0.1 mg to about 70 mg per day. In choosing a regimen useful in the prevention or treatment of estrogen related diseases or syndromes it may frequently be necessary to begin with a dosage of from about 20 to about 70 mg per day and when the condition is under control to reduce the dosage as low as from about 0.1 to about 10 mg per day. The exact dosage will depend upon the mode of administration, form in which adminstered, the subject to be treated and the body weight of the subject to be treated, and the preference and experience of the physician or veterinarian in charge.

The route of administration may be any route, which effectively transports the active compound to the appropriate or desired site of action, such as oral or parenteral e.g. rectal, transdermal, depot, subcutaneous, intravenous, intraurethral, intramuscular, intranasal, ophthalmic solution or an ointment, the oral route being preferred.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active comound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

The pharmaceutical preparations can be sterilized and mixed, if desired, with auxiliary agents, emulsifiers, salt for influencing osmotic pressure, buffers and/or coloring substances and the like, which do not deleteriously react with the active comounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 0.1 to about 100 mg in a pharmaceutically acceptable carrier per unit dosage.

A typical tablet, appropriate for use in this method, may be prepared by conventional tabletting techniques and contains:

Active compound 5.0 mg
Lactosum 67.8 mg Ph.Eur.
Avicel® 31.4 mg
Amberlite® 1.0 mg
Magnesii stearas 0.25 mg Ph. Eur.

The compounds according to this invention may be suitable for administration to an animal. Such animals include both domestic animals, for example livestock, laboratory animals, and household pets, and non-domestic animals such as wildlife. More preferably, the animal is a vertebrate. Most preferably, a compound according to this invention shall be administered to a mammal. It is especially preferred that the animal is a domestic mammal or a human. The most preferred mammal is a human. For such purposes, a comound of this invention may be administered as a feed additive or in bulk form.

The invention is explained more in detail in the below examples, which illustrates the invention. It is not to be considered as limiting the scope of the invention being defined by the appended claims.

EXAMPLE 1

2-(4-Benzyloxyphenyl)-1-ethyl-4-hydroxymethylpyrrolo[2,1,5-cd]indolizine

Step 1
4-Benzyloxyphenacylbromide

4-Benzyloxyacetophenone (56.57 g, 250 mmol) was dissoved in 1350 ml of methanol, with warming, and bromine (15.5 ml, 300 mmol) was added dropwise as a solution in 150 ml of methanol. After stirring for 3 hours the methanol was evaporated and the residue was suspended in 200 ml of 1 M hydrochloric acid and stirred for 10 minutes. The organic material was extracted into dichloromethane (1×500 ml, and 1×200 ml). The combined organic layers were washed with brine, dried over magnesium sulfate, and evaporated to an off-white solid, which was recrystalized from hot ethanol and water, to afford 69.39 g (91%) of 4-benzyloxyphenacylbromide. M.p. 85–88° C. MS(GC): m/z 306 (M+1). $^1$H-NMR (CDCl$_3$, 200 MHz) δ: 4.39 (s, 2H); 5.13 (s, 2H); 7.03 (d, 2H); 7.32–7.46 (m, 5H); 7.98 (d, 2H).

Step 2
2-(4-Benzyloxyphenyl)-1-ethylindolizine

A solution of 4-benzyloxyphenacylbromide (15.7 g, 51 mmol) and 2-n-propylpyridine (12 ml, 108 mmol) in 75 ml of dry acetone was heated to reflux for four days. The mixture was cooled and the precipitate was isolated and dried to afford 17.34 g of 1-(4-benzyloxyphenacyl)-2-n-propylpyridinium bromide. The quaternary salt (17.34 g) was suspended in 250 ml of water and sodium hydrogen carbonate (17.1 g) was added. The mixture was refluxed for three hours. The resulting precipitate was filtered off, washed with water and dried to an overall yield of 12.86 g (77%) of 2-(4-benzyloxyphenyl)-1-ethylindolizine. M.p. 106–108° C. MS(SP): m/z 328 (M+1). $^1$H-NMR (DMSO-d$_6$, 200 MHz) δ: 1.10 (t, 3H); 2.81 (q, 2H); 5.13 (s, 2H); 6.48 (dd, 1H); 6.61 (dd, 1H); 7.08 (d, 2H); 7.31–7.45 (m, 6H); 7.49 (d, 2H); 7.56 (s, 1H); 8.13 (d, 1H). Analysis: Calculated for $C_{23}H_{21}N_1O_1$: C, 84.37; H, 6.48; N, 4.28%; Found: C, 84.33; H, 6.51; N, 4.17%.

Step 3
Methyl 3-(4-benzyloxyphenyl)-4-ethylpyrrolo[2,1,5-cd]indolizine-1-carboxylate A solution of 2-(4-benzyloxyphenyl)-1-ethylindolizine (6.55 g, 20 mmol) and methylpropiolate (10.4 g, 124 mmol) in 250 ml of dry toluene was heated to 100° C. under nitrogen atmosphere and stirred for 2½ hour. The mixture was cooled to room temperature and 2,3-dichloro-5,6-dicyano-1,4-benzoequinone (1.84 g, 8.1 mmol) was added and stirring was continued for 1 our. The mixture was filtered through celite and the solvent removed. The crude product was purified by column chromatography over silica gel 60, using 20% of diethyl ether in hexane as the eluent to afford 4.82 g (58%) of methyl 3-(4-benzyloxyphenyl)-4-ethylpyrrolo[2,1,5-cd]indolizine-1-carboxylate. M.p. 129–131° C. MS(SP): m/z 409 (M+). $^1$H-NMR (CDCl$_3$, 200 MHz) δ: 1.47 (t, 3H); 3.22 (q, 2H); 4.01 (s, 3H); 5.16 (s, 2H); 7.15 (d, 2H); 7.32–7.52 (m, 5H); 7.72 (d, 2H); 7.75–7.90 (m, 2H); 8.03 (s, 1H); 8.33 (dd, 1H). Analysis: Calculated for $C_{27}H_{23}N_1O_3$: C, 79.20; H, 5.66; N, 3.42%; Found: C, 79.10; H, 5.50; N, 3.20%.

Step 4
2-(4-Benzyloxyphenyl)-1-ethyl-4-hydroxymethylpyrrolo[2,1,5-cd]indolizine

Methyl 3-(4-benzyloxyphenyl)-4-ethylpyrrolo[2,1,5-cd]indolizine-1-carboxylate (8.5 g, 20.8 mmol) was dissolved in 170 ml of dry tetrahydrofurane under a nitrogen atmosphere. Lithium aluminium hydride (1.24 g, 32.6 mmol) was added in portions and stirring was continued for 2½ hours. Water (10 ml) was added dropwise, and 95 ml of saturated aqueous potassium carbonate and 200 ml of diethyl ether was added. The organic layer was separated, and the aqueous layer was extracted with diethyl ether (2×300 ml). The combined organic layers were washed with 200 ml of water and dried over sodium hydrogen carbonate. The solvent was evaporated and the remaining product was dried to afford 7.7 g (97%) of the title compound as yellow crystals. M.p. 148–150° C. MS(SP): m/z 381 (M+). $^1$H-NMR (CDCl$_3$, 300 MHz) δ: 1.48 (t, 3H); 3.23 (q, 2H); 5,17 (s, 2H); 5.18 (s, 2H); 7.14 (d, 2H); 7.32–7.52 (m, 5H); 7.57 (s, 1H); 7.65 (t, 1H); 7.72 (d, 2H); 7.92 (d, 1H); 8.02 (d, 1H).

EXAMPLE 2

2-(4-Benzyloxyphenyl)-1-ethyl-4-((2-piperidinoethoxy)methyl)pyrrolo[2,1,5-cd]indolizine 2-(4-Benzyloxyphenyl)-1-ethyl-4-hydroxymethylpyrrolo[2,1,5-cd]indolizine (0.88 g, 1.26 mmol) was dissolved in 40 ml of dry dimethylformamide under a nitrogen atmosphere. Sodium hydride (80% in oil) (0.24 g, 8.0 mmol) and potassium tert-butoxide (0.1 g, 0.9 mmol) was added in portions and stirring was continued for ten minutes. 1-(2-chloroethyl)piperidine hydrochloride (0.74 g, 4 mmol) was added, and the solution was stirred for four hours. Ethanol (10 ml) was added dropwise, and the reaction mixture was diluted with 200 ml of water. The organic material was extracted into toluene (3×50 ml), and the combined organic layers were dried over magnesium sulfate. The solvent was evaporated and the crude product was purified by column chromatography over silica gel 60, using 10% of methanol in dichloromethane as the eluent to afford 0.505 g (81%) of 2-(4-benzyloxyphenyl)-1-ethyl-4-((2-piperidinoethoxy)methyl)pyrrolo[2,1,5-cd]indolizine as a yellow oil. MS(SP): m/z 492 (M+). $^1$H-NMR (CDCl$_3$, 300 MHz) δ: 1.35–1.50 (m, 5H); 1.68 (m, 4H); 2.63 (m, 4H); 2.76 (t, 2H); 3.23 (q, 2H); 3.79 (t, 2H); 5.01 (s, 2H); 5.12 (s, 2H); 7.13 (d, 2H); 7.30–7.50 (m, 5H); 7.52 (s, 1H); 7.62 (t, 1H); 7.70 (d, 2H); 7.88 (d, 1H); 7.97 (d, 1H).

EXAMPLE 3

2-(4-Benzyloxyphenyl)-1-ethyl-4-methoxymethylpyrrolo[2,1,5-cd]indolizine 2-(4-Benzyloxyphenyl)-1-ethyl-4-hydroxymethylpyrrolo[2,1,5-cd]indolizine was alkylated, using a proper alkylating agent, by the general synthetic principle outlined in example 2, to afford 2-(4-benxyloxyphenyl)-1-ethyl-4-methoxymethylpyrrolo[2,1,5-cd]indolizine as yellow crystals in 60% yield. M.p. 111–113° C. MS(SP): m/z 395 (M+). $^1$H-NMR (CDCl$_3$, 300 MHz) δ: 1.47 (t, 3H); 3.26 (q, 2H); 3.44 (s, 3H); 4.97 (s, 2H); 5.16 (s, 2H); 7.13 (d, 2H); 7.34–7.52 (m, 5H); 7.56 (s, 1H); 7.63 (t, 1H); 7.73 (d, 2H); 7.91 (d, 1H); 7.99 (d, 1H).

EXAMPLE 4

2-(4-Benzyloxyphenyl)-1-ethyl-4-propoxymethylpyrrolo[2,1,5-cd]indolizine 2-(4-Benzyloxyphenyl)-1-ethyl-4-hydroxymethylpyrrolo[2,1,5-cd]indolizine was alkylated, using a proper alkylating agent, by the general synthetic principle outlined in example 2, to afford 2-(4-benzyloxyphenyl)-1-ethyl-4-propoxymethylpyrrolo[2,1,5-cd]indolizine as yellow crystals in 64% yield. M.p. 78–80° C. MS(SP): m/z 423 (M+). $^1$H-NMR (CDCl$_3$, 300 MHz) δ: 0.92 (t, 3H); 1.45 (t, 3H); 1.62 (m, 2H); 3.23 (q, 2H); 3.52 (t, 2H); 5.02 (s, 2H); 5.15 (s, 2H); 7.14 (d, 2H); 7.31–7.51 (m, 5H); 7.55 (s, 1H); 7.63 (t, 1H); 7.73 (d, 2H); 7.89 (d, 1H); 7.99 (d, 1H).

EXAMPLE 5

2-(4-Benxyloxyphenyl)-4-((3-dimethylaminopropoxy)methyl)-1-ethylpyrrolo[2,1,5-cd]indolizine 2-(4-Benzyloxyphenyl)-1-ethyl-4-hydroxymethylpyrrolo[2,1,5-cd]indolizine (1.0 g, 2.62 mmol) was dissolved in 100 ml of dry dimethylformamide under nitrogen atmosphere. Sodium hydride (60% in oil) (1.23 g, 30.8 mmol) and potassium-t-butoxide (0.03 g, 0.26 mmol) was added in portions and stirring was continued for ten minutes. 3-Dimethylamino-1-propylchloride hydrochloride (1.24 g, 7.84 mmol) was added, and the solution was stirred for twenty-four hours. Ethanol (20 ml) was added dropwise, and the reaction mixture was diluted with 250 ml of water. The organic material was extracted into ethyl acetate (2×100 ml), and the combined organic layers were dried over sodium hydrogen carbonate. The solvent was evaporated and the crude product was purified by column chromatography over silica gel 60, using 10% of methanol in dichloromethane as the eluent to afford 0.58 g (47%) of 2-(4-benzyloxyphenyl)-4-((3-dimethylaminopropoxy)methyl)-1-ethylpyrrolo[2,1,5-cd]indolizine as yellow crystals. M.p. 63–65° C. MS(SP): m/z 466 (M+). $^1$H-NMR (CDCl$_3$, 300 MHz) δ: 1.47 (t, 3H); 1.82 (m, 2H); 2.23 (s, 6H); 2.39 (t, 2H); 3.24 (q, 2H); 3.61 (t, 2H); 5.01 (s, 2H); 5.17 (s, 2H); 7.15 (d, 2H); 7.32–7.52 (m, 5H); 7.53 (s, 1H); 7.64 (t, 1H); 7.73 (d, 2H); 7.91 (d, 1H); 7.99 (d, 1H).

EXAMPLE 6

2-(4-Benzyloxyphenyl)-4-((2-diethylaminoethoxy)methyl)-1-ethylpyrrolo[2,1,5-cd]indolizine 2-(4-Benzyloxyphenyl)-1-ethyl-4-hydroxymethylpyrrolo[2,1,5-cd]indolizine was alkylated, using a proper alkylating agent, by the general synthetic principle outlined in example 5, to afford 2-(4-benzyloxyphenyl)-4-((2-diethylaminoethoxy)methyl)-1-ethylpyrrolo[2,1,5-cd]indolizine as a yellow oil in 79% yield. MS(SP): m/z 480 (M+). $^1$H-NMR (CDCl$_3$, 300 MHz) δ: 1.02 (t, 6H); 1.47 (t, 3H); 2.58 (q, 4H); 2.71 (t, 2H); 3.23 (q, 2H); 3.67 (t, 2H); 5.03 (s, 2H); 5.17 (s, 2H); 7.15 (d, 2H); 7.32–7.52 (m, 5H); 7.54 (s, 1H); 7.63 (t, 1H); 7.73 (d, 2H); 7.90 (d, 1H); 7.99 (d, 1H).

EXAMPLE 7

2-(4-Benzyloxyphenyl)-1-ethyl-4-((2-pyrrolidinoethoxy)methyl)pyrrolo[2,1,5-cd]indolizine 2-(4-Benzyloxyphenyl)-1-ethyl-4-hydroxymethylpyrrolo[2,1,5-cd]indolizine was alkylated, using a proper alkylating agent, by the general synthetic principle outlined in example 5, to afford 2-(4-benzyloxyphenyl)-1-ethyl-4-((2-pyrrolidinoethoxy)methyl)pyrrolo[2,1,5-cd]-indolizine as a yellow oil in 57% yield. MS(SP): m/z 478 (M+). $^1$H-NMR (CDCl$_3$, 300 MHz) δ: 1.48 (t, 3H); 1.82 (m, 4H); 2.68 (m, 4H); 2.80 (t, 2H); 3.32 (q, 2H); 3.74 (t, 2H); 5.04 (s, 2H); 5.15 (s, 2H); 7.15 (d, 2H); 7.32–7.52 (m, 5H); 7.54 (s, 1H); 7.64 (t, 1H); 7.72 (d, 2H); 7.90 (d, 1H); 7.99 (d, 1H).

EXAMPLE 8

2-(4-Benzyloxyphenyl)-1-ethyl-4-((2(morpholine-4-yl)ethoxy)methyl)pyrrolo[2,1,5- -cd]indolizine 2-(4-Benzyloxyphenyl)-1-ethyl-4-hydroxymethylpyrrolo[2,1,5-cd]indolizine was alkylated, using a proper alkylating agent, by the general synthetic principle outlined in example 5, to afford 2-(4-benzyloxyphenyl)-1-ethyl-4-((2-(morpholine-4-yl)ethoxy)methyl)pyrrolo[2,1,5-cd]indolizine as a yellow oil in 62% yield. $^1$H-NMR (CDCl$_3$, 300 MHz) δ: 1.47 (t, 3H); 2.45 (t, 4H); 2.60 (t, 2H); 3.32 (q, 2H); 3.62–3.72 (m, 6H); 5.04 (s, 2H); 5.16 (s, 2H); 7.15 (d, 2H); 7.31–7.55 (m, 6H); 7.63 (t, 1H); 7.72 (d, 2H); 7.91 (d, 1H); 7.99 (d, 1H).

EXAMPLE 9

2-(4-Benzyloxyphenyl)-4-((2-dimethylaminoethoxy)methyl)-1-ethylpyrrolo[2,1,5-cd]indolizine 2-(4-Benzyloxyphenyl)-1-ethyl-4-hydroxymethylpyrrolo[2,1,5-cd]indolizine was alkylated, using a proper alkylating agent, by the general synthetic principle outlined in example 5, to afford 2-(4-benzyloxyphenyl)-4-((2-dimethylaminoethoxy)methyl)-1-ethylpyrrolo[2,1,5-cd] indolizine as a yellow oil in 56% yield. $^1$H-NMR (CDCl$_3$, 300 MHz) δ: 1.47 (t, 3H); 22.7 (s, 6H); 2.54 (t, 2H); 3.32 (q, 2H); 3.63 (t, 2H); 5.05 (s, 2H); 5.16 (s, 2H); 7.14 (d, 2H); 7.32–7.52 (m, 5H); 7.55 (s, 1H); 7.63 (t, 1H); 7.72 (d, 2H); 7.90 (d, 1H); 8.00 (d, 1H).

EXAMPLE 10

2-(4-Benzyloxyphenyl)-1-ethyl-4-((3-piperidinopropoxy)methyl)pyrrolo[2,1,5-cd] indolizine 2-(4-Benzyloxyphenyl)-1-ethyl-4-hydroxymethylpyrrolo [2,1,5-cd]indolizine was alkylated, using a proper alkylating agent, by the general synthetic principle outlined in example 5, to afford 2-(4-benzyloxyphenyl)-1-ethyl-4-((3-piperidinopropoxy)methyl)pyrrolo[2,1,5-cd]indolizine as a yellow oil in 57% yield. $^1$H-NMR (CDCl$_3$, 300 MHz) δ: 1.37–1.62 (m, 9H); 1.82 (pentet, 2H); 2.30–2.45 (m, 6H); 3.24 (q, 2H); 3.59 (t, 2H); 5.02 (s, 2H); 5.17 (s, 2H); 7.15 (d, 2H); 7.32–7.54 (m, 6H); 7.63 (t, 1H); 7.74 (d, 2H); 7.90 (d, 1H); 7.99 (d, 1H).

EXAMPLE 11

6-[2-(4-Benzyloxyphenyl)-1-ethylpyrrolo[2,1,5-cd] indolizin-4-ylmethoxy]hexanoic Acid Dimethylamide 2-(4-Benzyloxyphenyl)-1-ethyl-4-hydroxymethylpyrrolo [2,1,5-cd]indolizine was alkylated, using 6-bromohexanoic acid dimethylamide as the alkylating agent, by the general synthetic principle outlined in Example 5, to afford 6-[2-(4-benzyloxyphenyl)-1-ethylpyrrolo[2,1,5-cd]indolizin-4-ylmethoxy]hexanoic acid dimethylamide as a yellow oil in 31% yield. $^1$H-NMR (CDCl$_3$, 300 MHz) δ: 1.37–1.50 (m, 5H); 160–1.71 (m, 4H); 2.28 (t, 2H); 2.91 (s, 3H); 2.93 (s, 3H); 3.24 (q, 2H); 3.56 (t, 2H); 5.01 (s, 2H); 5.17 (s, 2H); 7.15 (d, 2H); 7.32–7.54 (m, 6H); 7.63 (t, 1H); 7.73 (d, 2H); 7.90 (d, 1H); 7.99 (d, 1H).

EXAMPLE 12

1-Ethyl-2-(4-hydroxyphenyl)-4-((2-piperidinoethoxy)methyl)pyrrolo[2,1,5-cd]indolizine A suspension of 2-(4-benzyloxyphenyl)-1-ethyl-4-(2-piperidinoethoxy)methyl)pyrrolo[2,1,5-cd]indolizine (0.5 g, 1.02 mmol) and 50 mg 10% palladium on charcoal in 24 ml of ethanol and 16 ml of tetrahydrofuran was stirred in hydrogen atmosphere for 24 hours. The reaction mixture was filtered twice and the solvent was evaporated. The resulting oil was crystallised from dichloromethane and petroleum ether to afford 0.27 g (66% of 1-ethyl-2-(4-hydroxyphenyl)-4-((2-piperidinoethoxy)methyl)pyrrolo[2,1,5-cd]indolizine as yellow crystals. M.p. 132–134° C. MS(SP): m/z 402 (M+). $^1$H-NMR (DMSO-d$_6$, 300 MHz) δ: 1.35–1.48 (m, 5H); 1.49–1.62 (m, 4H); 2.57–2.89 (m, 6H); 3.22 (q, 2H); 3.70 (t, 2H); 5.01 (s, 2H); 6.98 (d, 2H); 7.62–7.78 (m, 4H); 8.07–8.13 (m, 2H); 9.77 (s, 1H).

EXAMPLE 13

1-Ethyl-2-(4-hydroxyphenyl)-4-methoxymethylpyrrolo[2,1,5-cd]indolizine 2-(4-Benzyloxyphenyl)-1-ethyl-4-methoxymethylpyrrolo [2,1,5-cd]indolizine was hydrogenated by the general synthetic principles outlined in example 12, to afford 1-ethyl-2-(4-hydroxyphenyl)-4-methoxymethylpyrrolo[2,1,5-cd] indolizine as yellow crystals in 71% yield. M.p. 137–141° C. MS(SP): m/z 306 (M+1). $^1$H-NMR (DMSO-d$_6$, 300 MHz) δ: 1.40 (t, 3H); 3.21 (q, 2H); 3.34 (s, 3H); 4.90 (s, 2H); 6.98 (d, 2H); 7.63–7.74 (m, 4H); 8.07–8.12 (m, 2H); 9.70 (s, 1H).

EXAMPLE 14

1-Ethyl-2-(4-hydroxyphenyl)-4-propoxymethylpyrrolo[2,1,5-cd]indolizine 2-(4-Benzyloxyphenyl)-1-ethyl-4-propoxymethylpyrrolo [2,1,5-cd]indolizine was hydrogenated by the general synthetic principles outlined in example 12, to afford 1-ethyl-2-(4-hydroxyphenyl)-4-propoxymethylpyrrolo[2,1,5-cd] indolizine as a red oil in 94% yield. MS(SP): m/z 333 (M+). $^1$H-NMR (CDCl$_3$, 200 MHz) δ: 0.92 (t, 3H); 1.46 (t, 3H); 1.64 (m, 2H); 3.22 (q, 2H); 3.52 (t, 2H); 5.02 (s, 2H); 6.99 (d, 2H); 7.52–7.72 (m, 4H); 7.90 (d, 1H); 8.00 (d, 1H).

EXAMPLE 15

4-((3-Dimethylaminopropoxy)methyl)-1-ethyl-2-(4-hydroxyphenyl)pyrrolo[2,1,5-cd]indolizine 2-(4-Benzyloxyphenyl)-4-((3-dimethylaminopropoxy) methyl)-1-ethylpyrrolo[2,1,5-cd]indolizine was hydrogenated by the general synthetic principles outlined in example 12, to afford 4-((3-dimethylaminopropoxy)methyl)-1-ethyl-2-(4-hydroxyphenyl)pyrrolo[2,1,5-cd]indolizine as yellow crystals in 84% yield. M.p. 146–147° C. MS(SP): m/z 376 (M+). $^1$H-NMR (CDCl$_3$, 300 MHz) δ: 1.43 (t, 3H); 1.87 (m, 2H); 2.29 (s, 6H); 2.48 (t, 2H); 3.19 (q, 2H); 3.61 (t, 2H); 5.00 (s, 2H); 6.88 (d, 2H); 7.51 (s, 1H); 7.58–7.64 (m, 3H); 7.87 (d, 1H); 7.96 (d, 1H). Analysis: Calculated for C$_{24}$H$_{28}$N$_2$O$_2$: C, 76.56; H, 7.50; N, 7.44%; Found: C, 76.47; H, 7.56; N, 7.13%.

EXAMPLE 16

4-((2-Diethylaminoethoxy)methyl)-1-ethyl-2-(4-hydroxyphenyl)pyrrolo[2,1,5-cd]indolizine 2-(4-Benzyloxyphenyl)-4-((2-diethylaminoethoxy) methyl)-1-ethylpyrrolo[2,1,5-cd]indolizine was hydrogenated by the general synthetic principles outlined in example 12, to afford 4-((2-diethylaminoethoxy)methyl)-1-ethyl-2-(4-hydroxyphenyl)pyrrolo[2,1,5-cd]indolizine as yellow crystals in 70% yield. M.p. 93–95° C. MS(SP): m/z 390 (M+). $^1$H-NMR (CDCl$_3$, 300 MHz) δ: 1.03 (t, 6H); 1.43 (t, 3H); 2.63 (q, 4H); 2.77 (t, 2H); 3.18 (q, 2H); 3.71 (t, 2H); 5.02 (s, 2H); 6.89 (d, 2H); 7.48–7.67 (m, 4H); 7.88 (d, 1H); 7.98 (d, 1H). Calculated for C$_{25}$H$_{30}$N$_2$O$_2$+0.73 mol % dichloromethane: C, 76.43; H, 7.70; N, 7.12%; Found: C, 76.43; H, 7.62; N, 7.03%.

EXAMPLE 17

1-Ethyl-2-(4-hydroxyphenyl)-4-((2-pyrrolidinoethoxy)methyl)pyrrolo[2,1,5-cd] indolizine 2-(4-Benzyloxyphenyl)-1-ethyl-4-(2-pyrrolidinoethoxy) methyl)pyrrolo[2,1,5-cd]indolizine was hydrogenated by the general synthetic principles outlined in example 12, to afford 1-ethyl-2-(4-hydroxyphenyl)-4-((2-pyrrolidinoethoxy)methyl)pyrrolo[2,1,5-cd]indolizine as yellow crystals in 77% Yield. M.p 128–130° C. MS(SP): m/z 388 (M+). $^1$H-NMR (DMSO-d$_6$, 300 MHz) δ: 1.40 (t, 3H); 1.67 (m, 4H); 2.57 (m, 4H); 2.74 (t, 2H); 3.21 (q, 2H); 3.63 (t, 2H); 4.98 (s, 2H); 6.98 (d, 2H); 7.62–7.73 (m, 4H); 8.08–8.12 (m, 2H), 9.70 (s, 1H). Calculated for $C_{25}H_{28}N_2O_2+3.58$ mol % dichloromethane: C, 75.03; H, 7.09; N, 6.95%; Found: C, 74.98; H, 7.26; N, 6.87%.

EXAMPLE 18

1-Ethyl-2-(4-hydroxyphenyl)-4-((2-morpholine-4-yl) ethoxy))methyl)pyrrolo[2,1,5-cd]indolizine 2-(4-Benzyloxyphenyl)-1-ethyl-4-((2-(morpholine-4-yl) ethoxy)methyl)pyrrolo[2,1,5-cd]indolizine was hydrogenated by the general synthetic principles outlined in example 12, to afford 1-ethyl-2-(4-hydroxyphenyl)-4-((2-(morpholine-4-yl)ethoxy))methyl)pyrrolo[2,1,5-cd] indolizine as yellow crystals in 84% Yield. M.p. 122–124° C. MS(SP): m/z 405 (M+). $^1$H-NMR (CDCl$_3$, 300 MHz) δ: 1.42 (t, 3H); 2.52 (t, 4H); 2.64 (t, 2H); 3.19 (q, 2H), 3.67–3.75 (m, 6H); 5.03 (s, 2H); 6.92 (d, 2H); 7.50 (s, 1H); 7.55–7.68 (m, 3H); 7.90 (d, 1H); 7.99 (d, 1H). Calculated for $C_{25}H_{28}N_2O_3+0.96$ mol % dichloromethane: C, 73.64; H, 6.93; N, 6.86%; Found: C, 73.65; H, 6.95; N, 6.65%.

EXAMPLE 19

4-((2-Dimethylaminoethoxy)methyl)-1-ethyl-2-(4-hydroxyphenyl)pyrrolo[2,1,5-cd]indolizine 2-(4-benzyloxyphenyl)-4-((2-dimethylaminoethoxy) methyl)-1-ethylpyrrolo[2,1,5-cd]indolizine was hydrogenated by the general synthetic principles outlined in example 12, to afford 4-((2-dimethylaminoethoxy)methyl)-1-ethyl-2-(4-hydroxyphenyl)pyrrolo[2,1,5-cd]indolizine as yellow crystals in 96% Yield. M.p. 141–143° C. MS(SP): m/z 362 (M+). $^1$H-NMR (CDCl$_3$, 300 MHz) δ: 1.41 (t, 3H); 2.32 (s, 6H); 2.62 (t, 2H); 3.13 (q, 2H); 3.71 (t, 2H); 5.03 (s, 2H); 6.89 (d, 2H); 7.49 (s, 1H); 7.53 (d, 2H); 7.62 (t, 1H); 7.88 (d, 1H); 8.98 (d, 1H). Analysis: Calculated for $C_{23}H_{26}N_2O_2+2.29$ mol % dichloromethane: C, 74.79; H, 7.12; N, 7.55%; Found: C, 74.71; H, 7.15; N, 7.43%.

EXAMPLE 20

1-Ethyl-2-(4-hydroxyphenyl)-4-((3-piperidinopropoxy)methyl)pyrrolo[2,1,5-cd] indolizine 2-(4-benzyloxyphenyl)-1-ethyl-4-((3-piperidinopropoxy) methyl)pyrrolo[2,1,5-cd]indolizine was hydrogenated by the general synthetic principles outlined in example 12, to afford 1-ethyl-2-(4-hydroxyphenyl)-4-((3-piperidinopropoxy)methyl)pyrrolo[2,1,5-cd]indolizine as yellow crystals in 79% Yield. M.p. 176–178° C. MS(SP): m/z 416 (M+). $^1$H-NMR (DMSO-d$_6$, 300 MHz) δ: 1.28–1.45 (m, 9H); 1.67 (pentet, 2H); 2.18–2.28 (m, 6H); 3.21 (q, 2H); 3.52 (t, 2H); 4.93 (s, 2H); 6.98 (d, 2H); 7.62–7.73 (m, 4H); 8.04–8.10 (m, 2H); 9.70 (s, 1H). Analysis: Calculated for $C_{27}H_{32}N_2O_2$: C, 77.85; H, 7.74; N, 6.72%; Found: C, 77.82; H, 7.75; N, 6.55%.

EXAMPLE 21

6-[1-Ethyl-2-(4-hydroxyphenyl)pyrrolo[2,1,5-cd] indolizin-4-ylmethoxy]hexanoic acid dimethylamide 6-[2-(4-Benzyloxyphenyl)-1-ethylpyrrolo[2,1,5-cd] indolizin-4-ylmethoxy]hexanoic acid dimethylamide was hydrogenated by the general synthetic principles outlined in example 12, to afford 6-[1-ethyl-2-(4-hydroxyphenyl) pyrrolo[2,1,5-cd]indolizin-4-ylmethoxy]hexanoic acid dimethylamide as an unstable yellow oil in 100% Yield. MS(FAB): m/z 433 (M+1). $^1$H-NMR (DMSO-d$_6$, 300 MHz) δ: 1.21–1.60 (m, 9H); 2.21 (t, 2H); 2.78 (s, 3H); 2.88 (s, 3H); 3.21 (q, 2H); 3.49 (t, 2H); 4.95 (s, 2H); 7.01 (d, 2H); 7.62–7.73 (m, 4H); 8.08 (d, 2H); 9.75 (br s, 1H).

EXAMPLE 22

3-(4-Benzyloxyphenyl)-4-ethyl-pyrrolo[2,1,5-cd] indolizine-1-carboxylic acid dimethylamide Step 1:

3-(4-Benzyloxyphenyl)-4-ethylpyrrolo[2,1,5-cd] indolizine-1-carboxylic acid

Methyl 3-(4-benzyloxyphenyl)-4-ethylpyrrolo[2,1,5-cd] indolizine-1-carboxylate (2.92 g, 7.13 mmol) was dissolved in 200 ml of methanol and 20 ml of water. Potassium hydroxide (6.40 g, 114 mmol) was added and the mixture was heated to reflux for 3 days. The reaction mixture was allowed to cool to room temperature and the methanol was evaporated. The orange solid was partitioned between 200 ml of dichloromethane and 200 ml of 1M hydrochloric acid and acidified with concentrated hydrochloric acid until pH=1. This resulted in the formation of a suspension. A further 800 ml of dichloromethane and 200 ml of water was added and the suspension was filtered to give 0.74 g (26%) of 3-(4-benzyloxyphenyl)-4-ethylpyrrolo[2,1,5-cd] indolizine-1-carboxylic acid as a yellow solid. The organic solution was washed with brine, dried over magnesium sulfate and evaporated to give a orange solid. This solid was recrystallised from acetone to afford 1.23 g (43%) of 3-(4-benzyloxyphenyl)-4-ethylpyrrolo[2,1,5-cd]indolizine-1-carboxylic acid as a yellow solid. M.p. 223–224° C. MS(SP): m/z 395 (M+). $^1$H-NMR (DMSO-d$_6$, 200 MHz) δ: 1.41 (t, 3H); 3.02 (q, 2H); 5.22 (s, 2H); 7.24 (d, 2H); 7.31–7.56 (m, 5H); 7.81 (d, 2H); 7.95 (t, 1H); 8.03 (s, 1H); 8.20 (d, 1H); 8.32 (d, 1H); 12.46 (bs, 1H).

Step 2:

Dimethyl-3-(4-benzyloxyphenyl)-4-ethylpyrrolo[2,1, 5-cd]indolizine-1-carboxamide 3-(4-Benzyloxyphenyl)-4-ethylpyrrolo[2,1,5-cd] indolizine-1-carboxylic acid (1.19 g, 3.01 mmol) was suspended in 100 ml of dry toluene and thionyl chloride (2.20 ml, 3.60 mmol) was added. A few drops of dimethylformamide was added as the catalyst and the mixture was stirred at room temperature for 4 hours. The reaction mixture was evaporated and the acid chloride intermediate was redissolved in 100 ml of dry tetrahydrofuran. A 2M solution of dimethyl amine in tetrahydrofuran (7 ml, 14 mmol) was added and the reaction mixture was stirred overnight. The solvents were evaporated and the remaining solid was partitioned between 150 ml of ethyl acetate and 50 ml of water and the solution was acidified with 1M hydrochloric acid until pH=1. The aqueous layer was extracted with 2×50 ml of ethyl acetate and the combined organic layers were washed with brine, dried over sodium sulfate and evaporated to give a dark gum. This gum was purified by column chromatography over silica gel 60, using a mixture of ethyl acetate and hexane (2:1) as the eluent. This gave 1.14 g (89%) of the title compound as an orange gum. MS(SP): m/z 422 (M+). $^1$H-NMR (CDCl$_3$, 300 MHz) δ: 1.47 (t, 3H); 3.22 (q, 2H); 3.30 (s, 6H); 5.16 (s, 2H); 7.16 (d, 2H), 7.32–7.53 (m, 5H); 7.68–7.78 (m, 4H); 7.90 (d, 1H); 8.24 (d, 1H).

EXAMPLE 23

5-Benzyloxy-2-(4-benzyloxyphenyl)-1-ethyl-3-hydroxymethylpyrrolo[2,1,5-cd]indolizine Step 1:

5-Nitro-2-n-propylpyridine

Sodium metal (6.9 g, 300 mmol) was added in small pieces to a refluxing solution of diethyl malonate (90 ml, 480 mmol). When the sodium was completely dissolved, 2-chloro-5-nitropyridine (45 g, 285 mmol) was added in small portions. Reflux was continued for 20 hours. Water (500 ml) was added and the organic material was extracted into 4×200 ml of ethyl acetate. The combined organic layers were washed with brine, dried over sodium sulfate, and the solvent was evaporated. The crude malonate intermediate was then dissolved in 100 ml of water and 100 ml of concentrated sulphuric acid, and the mixture was refluxed at 110° C. for 18 hours. The mixture was then poured into 1200 ml of concentrated sodium hydroxide solution, and the organic material was extracted into 5×350 ml of dichloromethane. The combined organic layers were washed with brine, dried over magnesium sulfate, and the solvent was evaporated. This gave 42.60 g (90%) of 5-nitro-2-n-propylpyridine as an orange oil. $^1$H-NMR (MeOD, 200 MHz) δ: 0.98 (t, 3H); 1.79 (sext, 2H); 2.89 (t, 2H); 7.51 (d, 1H); 8.48 (dd, 1H); 9.25 (d, 1H).

Step 2:

5-Amino-2-n-propylpyridine

A suspension of 5-nitro-2-n-propylpyridine (8.31 g, 50 mmol) and 400 mg 5% palladium on charcoal in 200 ml of ethanol was stirred in a hydrogen atmosphere until no more hydrogen was absorbed. The reaction mixture was filtered twice and the solvent was evaporated. The resulting oil was purified by kugelrohr destillation at 150° C. and high vacuum pressure. This gave 6.72 g (98%) of 5-amino-2-n-propylpyridine as a colourless oil. MS(GC): m/z 136 (M+). $^1$H-NMR (CDCl$_3$, 200 MHz) δ: 0.83 (t, 3H); 1.60 (sext, 2H); 2.54 (t, 2H); 3.67 (br s, 2H); 6.81 (d, 2H); 7.91 (d, 1H).

Step 3:

5-Hydroxy-2-n-propylpyridine

5-Amino-2-n-propylpyridine (70.3 g, 516 mmol) was dissolved in 1300 ml of 1M hydrochloric acid and sodium nitrite (35.6 g, 516 mmol) dissolved in 300 ml of water was added dropwise at 0° C. The reaction mixture was stirred at 0° C. for ½ hour, heated to 70° C. for 2 hours, and then stirred at room temperature the overnight. The reaction mixture was neutralised to pH=8 by adding solid sodium hydrogen carbonate, and the product was extracted into ethyl acetate. The combined organic layers were washed with brine, dried over sodium sulfate, and the solvent was evaporated. The crude product was purified by column chromatography over silica gel 60, using ethyl acetate:petroleum ether (1:1) as the eluent. This gave 65.7 g (92%) of 5-hydroxy-2-n-propylpyridine as an orange wax. $^1$H-NMR (CDCl$_3$, 200 MHz) δ: 0.91 (t, 3H); 1.68 (sext, 2H); 2.71 (t, 2H); 7.09 (d, 1H); 7.25 (dd, 1H); 8.13 (d, 1H); 11.79 (s, 1H).

Step 4:

5-Benzyloxy-2-n-propylpyridine

5-Hydroxy-2-n-propylpyridine (13.72 g, 100 mmol) was dissolved in 200 ml of dry tetrahydrofuran under a nitrogen atmosphere, and at 0° C., 60% sodium hydride (7.0 g, 175 mmol) was added in small portions. The reaction mixture was stirred for ½ hour when a precipitate became visible. This precipitate was redissolved by adding 30 ml of dimethyl sulfoxide. Benzylbromide (13.1 ml, 18.84 mmol) was added dropwise and the resulting mixture was stirred at room temperature for 3 hours. Water (200 mol) and 20 ml of triethylamine was added and The pH was adjusted to 12 with a saturated sodium hydrogen carbonate solution. The organic material was extracted into ethyl acetate and the combined organic layers were washed with brine, dried over sodium sulfate, and the solvent was evaporated. The crude product was purified by destillation and gave 19.39 g (85%) of 5-benzyloxy-2-n-propylpyridine as an orange coloured oil. B.p. 160–170° C. 0.3 mbar. MS(SP): m/z 227 (m+). $^1$H-NMR (CDCl$_3$, 200 MHz) δ: 0.95 (t, 3H); 1.72 (sext, 2H); 2.70 (t, 2H); 5.05 (s, 2H); 7.02 (d, 1H); 7.18 (dd, 1H); 7.24–7.46 (m, 5H); 8.30 (d, 1H).

Step 5:

6-Benzyloxy-2-(4-benzyloxyphenyl)-1-ethylindolizine

5-Benzyloxy-2-n-propylpyridine (50.15 g, 221 mmol) and 4-benzyloxyphenacylbromide (67.34 g, 221 mmol) was dissolved in 400 ml of dry acetone under a nitrogen atmosphere. The mixture was heated to reflux for 5 days. The reaction was cooled to room temperature and the solvent was removed. The remaining quaternary salt was suspended in 250 ml of water and 250 ml of diethyl ether and filtered off. The dried salt was suspended in 600 ml of water and sodium hydrogen carbonate (74 g, 884 mmol) was added. The mixture was refluxed for 3 days. The resulting precipitate was filtered off, washed with water and dried to afford 75.38 g (78%) of 6-benzyloxy-2-(4-benzyloxyphenyl)-1-ethylindolizine as brown crystals. $^1$H-NMR (DMSO-d$_6$, 200 MHz) δ: 1.10 (t, 3H); 2.79 (q, 2H); 5.02 (s, 2H); 5.12 (s, 2H); 6.52 (dd, 1H); 7.08 (d, 2H); 7.29–7.51 (m, 14H); 7.96 (s, 1H).

Step 6:

Dimethyl 7-benzyloxy-3-(4-benzyloxyphenyl)-4-ethylpyrrolo[2,1,5-cd]indolizine-1,2-dicarboxylate 6-Benzyloxy-2-(4-benzyloxyphenyl)-1-ethylindolizine (50.0 g, 115 mmol) and dimethyl acetylene dicarboxylate (18.5 ml, 150 mmol) was dissolved in 1100 ml of dry toluene at 0° C. The reaction was slowly heated to room temperature and stirred for 3 hours. 2,3-Dichloro-5,6-dicyano-1,4-benzoquinone (26 g, 115 mmol) was added and stirring was continued for ½ hour. The mixture was filtered through celite and the solvent removed. The crude product was crystallised from methanol to afford 47.4 g (71%) of dimethyl 7-benzyloxy-3-(4-benzyloxyphenyl)-4-ethylpyrrolo[2,1,5-cd]indolizine-1,2-dicarboxylate as yellow crystals. M.p. 115–120° C. $^1$H-NMR (DMSO-d$_6$, 300 MHz) δ: 1.32 (t, 3H); 3.01 (q, 2H); 3.56 (s, 3H); 3.72 (s, 3H); 5.21 (s, 2H); 5.50 (s, 2H); 7.17 (d, 2H; 7.32–7.53 (m, 10H); 7.60 (d, 2H); 7.67 (d, 1H); 8.22 (d, 1H).

Step 7:

7-Benzyloxy-3-(4-benzyloxyphenyl)-4-ethylpyrrolo[2,1,5-cd]indolizine-1,2-dicarboxylic acid Dimethyl 7-Benzyloxy-3-(4-benzyloxyphenyl)-4-ethylpyrrolo[2,1,5-cd]indolizine-1,2-dicarboxylate (1.0 g, 1.7 mmol) was dissolved in 100 ml of methanol. Potassium hydroxide (3.37 g, 60 mmol) and 2 ml of water was added and the mixture was heated to reflux for 4 days. The reaction mixture was allowed to cool to room temperature and acidified with concentrated hydrochloric acid until pH=1.

The resulting precipitate was filtered off, and washed with water and ethanol. This gave 0.89 g (96%) of 7-benzyloxy-3-(4-benzyloxyphenyl)-4-ethylpyrrolo[2,1,5-cd]indolizine-1,2-dicarboxylic acid as yellow crystals. M.p. 151–161° C. MS(SP): m/z 545 (M+). $^1$H-NMR (DMSO-$d_6$, 200 MHz) δ: 1.32 (t, 3H); 3.02 (q, 2H); 5.18 (s, 2H); 5.52 (s, 2H); 7.15 (d, 2H); 7.29–7.56 (m, 10H); 7.61–7.71 (m, 3H); 8.18 (d, 1H).

Step 8:

7-Benzyloxy-3-(4-benzyloxyphenyl)-4-ethylpyrrolo[2,1,5-cd]indolizine-1,2-dicarboxylic acid anhydride 7Benzyloxy-3-(4-benzyloxyphenyl)-4-ethylpyrrolo[2,1,5-cd]indolizine-1,2-dicarboxylic acid (34.00 g, 60 mmol) was dissolved in 200 ml of pyridine under a nitrogen atmosphere. Acetic acid anhydride (8.8 ml, 90 mmol) was added and the mixture was stirred at room temperature for 2½ hours. The reaction mixture was allowed to cool to room temperature and the product was filtered off, and washed with petroleum ether. This gave 25.63 g (81%) of the title compound as yellow crystals. M.p. 229–231° C. MS(SP): m/z 527 (M+). $^1$H-NMR (CDCl$_3$, and DMSO-$d_6$, 300 MHz) δ: 1.47 (t, 3H); 3.20 (q, 2H); 5.18 (s, 2H); 5.59 (s, 2H); 7.19 (d, 2H); 7.30–7.55 (m, 9H); 7.62 (d, 2H); 7.79 (d, 2H); 7.98 (d, 1H).

Step 9:

7-Benzyloxy-3-(4-benzyloxyphenyl)-2-ethoxycarbonyl-4-ethylpyrrolo[2,1,5-cd]indolizine-1-carboxylic acid 7-Benzyloxy-3-(4-benzyloxyphenyl)-4-ethylpyrrolo[2,1,5-cd]indolizine-1,2-dicarboxylic acid anhydride (25.62 g, 49 mmol) was suspended in pyridine (12.85 ml, 159 mmol) and 400 ml of ethanol under a nitrogen atmosphere. The mixture was heated to reflux for 3 days. The reaction mixture was allowed to cool to room temperature and the product was filtered off, and washed with petroleum ether. This gave 21.6 g (77%) of 7-benzyloxy-3-(4-benzyloxyphenyl)-2-ethoxycarbonyl-4-ethylpyrrolo[2,1,5-cd]indolizine-1-carboxylic acid as yellow crystals. M.p. 171–173° C. MS(SP): m/z 573 (M+). $^1$H-NMR (CDCl$_3$, 300 MHz) δ: 1.04 (t, 3H); 1.35 (t, 3H); 3.01 (q, 2H); 4.16 (q, 2H); 5.15 (s, 2H); 5.54 (s, 2H); 7.09 (d, 2H); 7.30–7.51 (m, 11H); 7.58 (d, 2H); 7.81 (d, 1H); 11.70 (br s, 1H).

Step 10:

Ethyl 7-benzyloxy-3-(4-benzyloxyphenyl)-4-ethylpyrrolo[2,1,5-cd]indolizine-2-carboxylate 7-Benzyloxy-3-(4-benzyloxyphenyl)-2-ethoxycarbonyl-4-ethylpyrrolo[2,1,5-cd]indolizine-1-carboxylic acid (21.63 g, 38 mmol) was dissolved in 220 ml of quinoline under a nitrogen atmosphere. Copper powder (3.35 g, 50 mmol) was added and the mixture was heated to 170° C. for 2½ hour. The reaction mixture was filtered when hot, and the filtrate was flash chromatographed over silica gel 60, using toluene: petroleum ether (1:1) as the eluent. Fractions containing the product were combined and added 300 ml of water was added and the pH was adjusted to 2 with 6N hydrochloric acid. The organic material was extracted into 3×300 ml of dichloromethane and the combined organic layers were washed with brine, dried over sodium sulfate and the solvent was evaporated. The crude product was purified by column chromatography over silica gel 60, using toluene:petroleum ether (1:1) as the eluent. The crude product was crystallised from hot toluene and petroleum ether. This gave 15.90 g (79%) of ethyl 7-benzyloxy-3-(4-benzyloxyphenyl)-4-ethylpyrrolo[2,1,5-cd]indolizine-2-carboxylate as yellow crystals. M.p. 114–116° C. MS(SP): m/z 529 (M+). $^1$H-NMR (DMSO-$d_6$, 300 MHz) δ: 0.92 (t, 3H); 1.28 (t, 3H); 2.93 (q, 2H); 4.00 (q, 2H); 5.19 (s, 2H); 5.61 (s, 2H); 7.12 (d, 2H); 7.32–7.53 (m, 11H); 7.59 (d, 2H); 7.74 (s, 1H); 8.16 (d, 1H).

Step 11:

5-Benzyloxy-2-(4-benzyloxyphenyl)-1-ethyl-3-hydroxymethylpyrrolo[2,1,5-cd]indolizine Ethyl 7-benzyloxy-3-(4-benzyloxyphenyl)-4-ethylpyrrolo[2,1,5-cd]indolizine-2-carboxylate (15.79 g, 30 mmol) was dissolved in 250 ml of dry tetrahydrofuran under a nitrogen atmosphere. Lithium aluminium hydride (1.8 g, 50 mmol) was added in small portions, and the mixture was stirred at room temperature for 2½ hours. Water was added until effervescence terminated and solid potassium carbonate was added until a white suspension was formed. Diethyl ether (200 ml) was added and the reaction mixture was stirred vigorously. The reaction mixture was filtered through celite and the organic material was extracted into 3×100 ml of diethyl ether and 3×100 ml of ethyl acetate. The combined organic layers were washed with brine, dried over sodium sulfate and the solvent was evaporated. The crude product was recrystallized from hot ethyl acetate and petroleum ether. This gave 13.06 g (89%) of 5-benzyloxy-2-(4-benzyloxyphenyl)-1-ethyl-3-hydroxymethyl-pyrrolo[2,1,5-cd]indolizine as yellow crystals. M.p. 133–134° C. MS(SP): m/z 487 (M+). $^1$H-NMR (DMSO-$d_6$, 400 MHz) δ: 1.34 (t, 3H); 3.04 (q, 2H); 4.81 (s, 2H); 5.18 (m, 3H); 5.57 (s, 2H); 7.20 (d, 2H); 7.31–7.64 (m, 14H); 7.92 (d, 1H). The structure has been proven by COSY, ROESY and NOESY, 400 MHz.

The general synthetic principles outlined in example 23 have been applied in the preparation of compounds mentioned in examples 24–27

EXAMPLE 24

1-Ethyl-3-hydroxymethyl-2-(4-methoxyphenyl)pyrrolo[2,1,5-cd]indolizine

M.p. 97–100° C. HPLC (eluent: 65% CH$_3$CN isocratic, 35% buffer H$_3$PO$_4$pH=3): Rt=8.98 min (99% purity). $^1$H-NMR (CDCl$_3$, 200 MHz) δ: 1.42 (t, 3H); 1.70 (t, 1H); 3.15 (q, 2H); 3.90 (s, 3H); 5.04 (d, 2H); 7.08 (d, 2H); 7.19 (s, 1H); 7.56–7.68 (m, 3H); 7.87 (d, 1H); 7.91 (d, 1H).

EXAMPLE 25

2-(4-Benzyloxyphenyl)-3-hydroxymethylpyrrolo[2,1,5-cd]indolizine

HPLC (eluent: 85% CH$_3$CN isocratic, 15% buffer H$_3$PO$_4$pH=3): Rt=4.50 min (98% purity).

EXAMPLE 26

5-Benzyloxy-1-ethyl-3-hydroxymethyl-2-phenylpyrrolo[2,1,5-cd]indolizine

M.p. 135–136° C. MS(SP): m/z 381 (M+). $^1$H-NMR (DMSO-$d_6$, 400 MHz) δ: 1.32 (t, 3H); 3.08 (q, 2H); 4.81 (d, 2H); 5.19 (t, 1H); 5.58 (s, 2H); 7.32–7.58 (m, 10H); 7.68 (d, 2H); 7.97 (d, 1H). The structure has been proven by COSY, ROESY and NOESY, 400 MHz.

EXAMPLE 27

2-(4-Benzyloxyphenyl)-1-ethyl-3-hydroxymethylpyrrolo[2,1,5-cd]indolizine

M.P. 140–141° C. MS(SP): m/z 381 (M+). $^1$H-NMR (CDCl$_3$, 200 MHz) δ: 1.42 (t, 3H); 1.66 (br s, 1H); 3.04 (q,

2H); 5.05 (s, 2H); 5.15 (s, 2H); 7.10–7.21 (m, 3H); 7.30–7.53 (m, 5H); 7.56–7.69 (m, 3H); 7.82–7.94 (m, 2H).

EXAMPLE 28

5-Benzyloxy-2-(4-benzyloxyphenyl)-1-ethyl-3-((2-piperidinoethoxy)methyl)pyrrolo[2,1,5-cd]indolizine 5-Benzyloxy-2-(4-benzyloxyphenyl)-1-ethyl-3-hydroxymethylpyrrolo[2,1,5-cd]indoliziine (0.40 g, 0.82 mmol) was dissolvedin 50 ml of dry dimethylformamide under a nitrogen atmosphere. Sodium hydride (6% in oil) (0.3 g, 7.4 mmol), potassium tert-butoxide (9 mg, 0.1 mmol) and 1-(2-chloroethyl)piperidine monohydrochloride (0.30 g, 1.64 mmol) was added, and the mixture was stirred at room temperature for 2 days. Ethanol (10 ml) was added dropwise, and the reaction mixture was diluted with 250 ml of water. The organic material was extracted into ethyl acetate (3×100 ml), and the combined organic layers were washed with brine and dried over sodium sulfate. The solvent was evaporated and the crude product was purified by column chromatography over silica gel 60, using 5% of methanol in dichloromethane as the eluent. This gave 458 mg (93%) of 5-benzyloxy-2-(4-benzyloxyphenyl)-1-ethyl-3-((2-piperidinoethoxy)methyl)pyrrolo[2,1,5-cd ]indolizine as a red oil. MS (SP): m/z 598 (M+). $^1$H-NMR (DMSO-$d_6$, 300 MHz)δ: 1.19–1.46 (m, 9H); 2.22–2.37 (m, 6H); 3.06 (q, 2H); 3.48 (t, 2H); 4.71 (s, 2H); 5.19 (s, 2H); 5.58 (s, 2H); 7.19 (d, 2H); 7.30–7.63 (m, 14H); 7.97 (d, 1H).

EXAMPLE 29

5-Benzyloxy-2-(4-benzyloxyphenyl)-1-ethyl-3-((3-piperidinopropoxy)methyl)-pyrrolo[2,1,5-cd ]indolizine 5-Benzyloxy-2-(4-benzyloxyphenyl)-1-ehtyl-3-hydroxymethylpyrrolo[2,1,5-cd]indolizine was alkylated, using a proper alkylating agent, by the general synthetic principles outlined in example 28, to afford 5-benzyloxy-2-(4-benzyloxyphenyl)-1-ethyl-3-((3-piperidinopropopoxy)-methylpyrrolo[2,1,5-cd ]indolizine as a red-brown oil in 76% yiield. MS(SP): m/z 612(M+). $^1$H-NMR (DMSO-$d_6$, 300 MHz)δ: 127–149 (m, 9H); 159 (quintet, 2H); 2.18–2.33 (m, 6H); 3.40 (q, 2H); 3.40 (t, 2H); 4.69 (s, 2H); 5.18 (s, 2H); 5.57 (s, 2H); 7.20 (d, 2H); 7.32–7.64 (m, 14H); 7.97 (d, 1H).

EXAMPLE 30

5-Benzloyx-2-(4-benzyloxyphenyl)-1-ethyl-3-((6-piperidinohexyloxy)methyl)-pyrrolo[2,1,5-cd ]indolizine
5-Benzloxy-2-(4-benzyloxyphenyl)-1-ethyl-3-hydroxymethylpyrrolo [2,1,5-cd]indolizine was alkylated using a proper alkylating agent, by the general synthetic principles outlined in example 28, to afford 5-benzyloxy-2-(4-benzyloxyphenyl)-1-ethyl-3-((6-piperidonhexyloxy)-methyl)pyrrolo[2,1,5-cd ]indolizine as an oil in 99% yield. MS(SP): m/z 654 (M+). $^1$H-NMR (DMSO-$d_6$, 200 MHz) δ: 109–1.49 (m, 17H ); 2.05–2.28 (m, 6H); 3.03 (q, 2H); 3.32 (t, 2H); 456 (s, 2H); 5.18 (s, 2H); 5.57 (s, 2H); 7.13 (d, 2H); 7.28–7.63 (m, 14H); 7.96 (d, 1H).

EXAMPLE 31

5-Benzyloxy-2-(4-benzyloxyphenyl)-1-ethyl-3-((7-piperidinoheptyloxy)methyl)-pyrrolo[2,1,5-cd]indolizine
5-Benzyloxy-2-(4-benzyloxyphenyl)-1-ethyl-3-hydroxymethylpyrrolo[2,1,5-cd]indolizine was alkylated using aproper aklylating agent, by the general synthetic principles outlined in example 28, to afford 5-benzyloxy-2-(4-benzyloxyphenyl)-1-ethyl-3-((7-piperidino-heptloxy)methyl)pyrrolo[2,1,5-cd ]indolizine as yellow crystals in 67% yield. M.p. 86–90° C. MS(FAB): m/z 669 (M+1). $^1$H-NMR (DMSO-$d_6$, 300 MHz)δ: 1.12–1.47 (m, 19H); 2.12 (t, 2H); 2.18–2.29 (m, 4H); 3.04 (q, 2H); 3.36 (t, 2H); 4.69 (s, 2H); 5.18 (s, 2H); 5.57 (s, 2H); 7.16 (d, 2H); 7.30–7.63 (m, 14H); 7.95 (d, 1H).

EXAMPLE 32

5-Benzyloxy-2-(4-benzyloxyphenyl)-1-ethyl-3-((8-piperidinooctyloxy)methyl)-pyrrolo[2,1,5-cd ]indolizine
5-Benzyloxy-2-(4-benzyloxyphenyl)-1-ethyl-3-hydroxymethylpyrrolo[2,1,5-cd]indolizine was alkylated using a proper alkylating agent, by the general synthetic principles outlined in example, 28, to afford 5-benzyloxy-2-(4-benzyloxyphenyl)-1-ethyl-3-((8-piperidinooctyloxy)-methyl)pyrrolo[2,1,5-cd ]indolizine as a yellow oil in 79% yield. MS(FAB): m/z 683 (M+) $^1$H-NMR (DMSO-$d_6$, 300 MHz) δ; 1.12–1.47 (m, 21H); 212 (t, 2H); 2.18–2.30 (m, 4H); 3.04 (q, 2H); 3.35 (t, 2H); 4.69 (s, 2H); 5.18 (s, 2H); 5.57 (s, 2H); 7.17 (d, 2H); 7.30–7.62 (m, 14H); 7.95 (d, 1H).

EXAMPLE 33

5-Benzyloxy-1-ethyl-2-phenyl-3-((2-piperidinoethoxy) methyl)pyrrolo[2,1,5-cd]indolizine
5-Benzyloxy-1-ethyl-3-hydroxmethyl-2-phenylpyrrolo [2,1,5-cd ]indolizine was alkylated using a proper alkylating agent, by the general synthetic principles outlined in exmaple 28, to afford 5-benzyloxy-1-ethyl-2-phenyl-3-((2-piperidinoethoxy)methyl)pyrrolo[2,1,5-cd]indolizine as yellow crystals in 85% yield. M.p. 190–194° C. MS(SP): m/z 492 (M+). $^1$H-NMR (DMSO-$d_6$, 300 MHz) δ: 1.30 –1.74 (m, 9H); 2.69–3.30 (m, 8H); 3.69 (t, 2H); 4.48 (s, 2H); 5,57 (s, 2H); 7.33–7.50 (m, 6H); 7.58 (m, 4H); 7.68 (d, 2H); 8.04 (d, 1H).

EXAMPLE 34

5Benzyloxy-1-ethyl-2-phenyl-3-((3-piperidinoproopoxy) methyl)pyrrolo[2,1,5-cd]indolizine
5-Benzyloxy-1-ethyl-3-hydroxymethyl-2-phenylpyrrolo [2,1,5-cd]indolizine was alkylated using a proper alkylating agent, by the general synthetic principles outlined in example 28to afford 5-benzyloxy-1-ethyl-2-phenyl-3-((3-piperidinopropoxy)methyl)pyrrolo[2,1,5-cd]inddolizine as yellow crystals in 84% yield M.p. 160–161° C. (MS(SP): m/z 506 (M+). $^1$H-NMR (DMSO-$d_6$, 300 MHz) δ: 1.30–1.86 (m, 11H); 2.68–2.89 (m, 4H); 3.09 (q, 2H); 3.30 (m, 2H+$H_2O$); 3.43 (t, 2H); 4.75 (s, 2H); 5.58 (s, 2H); 7.32–7.49 (m, 6H); 7.58 (m, 4H); 7.68 (d, 2H); 8.02 (d, 1H).

EXAMPLE 35

2-(4-Benzyloxyphenyl)-1-ethyl-3-((2-piperidinoethoxy) methyl)pyrrolo[2,1,5-cd]indolizine
2-(4-Benzyloxyphenyl)-1-ethyl-3-hydroxymethylpyrrolo [2,1,5-cd]indolizine was alkylated using a proper alkylating agent, by the general synthetic principles outlined in example 28, to afford 2-(4-benzyloxyphenyl)-1-ethyl-3-((2-piperidinoethoxy)methyl)pyrrolo[2,1,5-cd]indolizine as an oil. $^1$H-NMR (CDCl$_3$, 200 MHz) δ: 1.35–1.69 (m, 9H); 2.39–2.62 (m, 6H); 3.03 (q, 2H); 3.65 (t, 2H); 4.86 (s, 2H); 5.15 (s, 2H); 7.10–7.20 (m, 3H); 7.29–7.52 (m, 5H); 7.56–7.57 (m, 3H); 7.82–7.91 (m, 2H).

EXAMPLE 36

5-Benzyloxy-2-(4-benzyloxyphenyl)-3-((5-chloropentyloxy)methyl)-1-ethylpyrrolo[2,1,5-cd ]indolizine
5-Benzyloxy-2-(4-benzyloxyphenyl)-1-ethyl-3-hydroxymethylpyrrolo[2,1,5-cd]indolizine was alkylated using a proper alkylating agent, by the general synthetic principles outlined in example 28, to afford 5-benzyloxy-2-(4-benzyloxyphenyl)-3-((5-chloropentyloxy)methyl)-1-ethylpyrrolo[2,1,5-cd]indolizine as a yellow oil in 90% yield. MS(SP): m/z 593 (M+1). $^1$H-NMR (DMSO-$d_6$, 300 MHz) δ: 1.28–1.48 (m, 7H); 1.64 (pentet, 2H); 3.05 (q, 2H); 3.36 (t, 2H+$H_2O$); 3.56 (t, 2H); 4.69 (s, 2H); 5.18 (s, 2H); 5.56 (s, 2H); 7.17 (d, 2H); 7.32–7.63 (m, 14H); 7.96 (d, 1H).

EXAMPLE 37

5-Benzyloxy-2-(4-benzyloxyphenyl)-3-((4-chlorobutoxy)methyl)-1-ethylpyrrolo[2,1,5-cd]indolizine 5-Benzyloxy-2-(4-benzyloxyphenyl)-1-ethyl-3-hydroxymethylpyrrolo[2,1,5-cd]indolizine was aklylated using a proper alkylating agent, by the general synthetic princples outlined in exmaple 28, to afford 5-benzyloxy-2-(4-benzyloxyphenyl)-3-((4-chlorobutoxy)methyl)-1-ethylpyrrolo[2,1,5-cd]indolizine as a red oil in 51% yield. MS(SP): m/z 579 (M+1). $^1$H-NMR (DMSO-$d_6$, 300 MHz) δ: 1.33 (t, 3H); 1.47–1.68 (m, 4H); 3.05 (q, 2H); 3.40 (t, 2H); 3.56 (t, 2H); 4.71 (s, 2H); 5.18 (s, 2H); 5.57 (s, 2H); 7.18 (d, 2H); 7.33–7.63 (m, 14H); 7.98 (d, 1H).

EXAMPLE 38

5-Benzyloxy-2-(4-benzyloxyphenyl)-1-ethyl-3-((5-methoxypentyloxy)methyl)pyrrolo [2.1.5-cd]indolizine 5-Benzyloxy-2-(4-benzyloxyphenyl)-1-ethyl-3-hydroxymethylpyrrolo[2,1,5-cd]indolizine was alkylated using a proper alkylating agent, by the general synthetic principles outlined in example 28, to afford 5-benzyloxy-2-(4-benzyloxyphenyl)-1-ethyl-3-((5-methoxypentyloxy)methyl)pyrrolo[2,1,5-cd]indolizine as a yellow oil in 37% yield. MS(SP): m/z 587 (M+). $^1$H-NMR (DMSO-$d_6$, 300 MHz) δ: 1.17–1.48 (m, 9H); 3.05 (q, 2H); 3.16 (s, 3H); 3.22 (t, 2H); 3.36 (t, 2H+$H_2O$); 4.69 (s, 2H); 5.17 (s, 2H); 5.55 (s, 2H); 7.17 (d, 2H); 7.31–762 (m, 14H); 7.94 (d, 1H).

EXAMPLE 39

2-(4-Benzyloxyphenyl)-1-ethyl-3-methoxymethylpyrrolo[2,1,5-cd]indolizine 2-(4-Benzyloxyphenyl)-1-ethyl-3-hydroxymethylpyrrolo[2,1,5-cd]indolizine was alkylated using a proper alkylating agent, by the general synthetic principles outlined in example 28, to afford 2-(4-benzyloxyphenyl)-1-ethyl-3-methoxymethylpyrrolo[2,1,5-cd]indolizine as an orange gum in 44% yield. MS(SP): m/z 395 (M+). $^1$H-NMR (CDCl$_3$, 300 MHz) δ: 1.42 (t, 3H); 3.15 (q, 2H); 3.40 (s, 3H); 4.79 (s, 2H); 5.16 (s, 2H); 7.14 (d, 2H); 7.21 (s, 1H); 7.30–7.52 (m, 5H); 7.59–7.68 (m, 3H); 7.85–7.92 (m, 2H).

EXAMPLE 40

1-Ethyl-3-methoxymethyl-2-(4-methoxyphenyl)pyrrolo[2,1,5-cd]indolizine

1-Ethyl-3-hydroxymethyl-2-(4-methoxyphenyl)pyrrolo[2,1,5-cd]indolizine (0.40 g, 1.31 mmol) was dissolved in 15 ml of dry tetrahydrofuran under a nitrogen atmosphere. Sodium hydrode (50% in oil) (0.06 g, 1.3 mmol) was added, and stirring was continued for ½ hour. Dimethyl sulfate (0.283 g, 2.25 mmol) was added, and the mixture was stirred at room temperature for 1day. 15 ml of water was added dropwise, and ther eaction mixture was diluted with 25 ml of diethyl ether. The organic material was extracted into diethyl ether, and the combined organic layers was washed with brine and dried over magnesium sulfate. The solvent was evaporated to afford 0.3 g (70%) of 1-ethyl-3-methoxymethyl-2-(4-methyoxyphenyl)pyrrolo[2,1,5-cd]indolizine. HPLC (Eluent: 65% $CH_3CN$ isocratic, 35% buffer $H_3PO_4$pH=3): Rt=23.75 min (94% purity). $^1$H-NMR (CDCl$_3$/CD$_3$OD, 200 MHz) δ: 1.42 (t, 3H); 3.16 (q, 2H); 3.41 (s, 3H); 3.88 (s, 3H); 4.78 (s, 2H); 7.07 (d, 2H); 7.21 (s, 1H); 7.56–7.69 (m, 3H); 7.81–7.91 (m, 2H).

EXAMPLE 41

2-(4-Benzyloxyphenyl)-3-methoxymethylpyrrolo[2,1,5-cd]indolizine 2-(4-Benzyloxyphenyl)-3-hydroxymethylpyrrolo[2,1,5-cd]indoolizine was alkylated by the general synthetic principles outlined in example 40, to afford 2-(4-benzyloxyphenyl)-3-methoxymethylpyrrolo[2,1,5-cd]indolizine as a solid in 94% yield. HPLC (eluent: 65% $CH_3CN$ isocratic, 35% buffer $H_3PO_4$pH=3): Rt=7.90 min (98% purity).

EXAMPLE 42

5-Benzyloxy-2-(4-benzyloxyphenyl)-1-ethyl-3-methoxymethylpyrrolo[2,1,5-cd]indolizine 5-Benzyloxy-2-(4-benzyloxyphenyl)-1-ethyl-3-hydroxymethylpyrrolo[2,1,5-cd]indolizine was alkylated by the general synthetic princples outlined in example 40, to afford 5-benzyloxy-2-(4-benzyloxyphenyl)-1-ethyl-3-methoxymethylpyrrolo[2,1,5-cd]indolizine as yellow crystals in 55% yield. HPLC (eluent: 65% $CH_3CN$ isocratic, 35% buffer $H_3PO_4$pH=3): Rt=16.36 min. M.p. 127–130° C. MS(SP): m/z 501 (M+). $^1$H-NMR (DMSO-$d_6$, 200 MHz) δ: 1.33 (t, 3H); 3.06 (q, 2H); 3.27 (s, 3H); 4.67 (s, 2H); 5.19 (s, 2H); 5.58 (s, 2H); 7.19 (d, 2H); 7.32–7.65 (m, 14H); 7.98 (d, 1H). Analysis: Calculated for $C_{34}H_{31}N_1O_3$+0.67 mol% dichloromethane: C, 80.96; H, 6.20; N, 2.77%; Found: C, 80.96; H, 6.22; N, 2.63%.

EXAMPLE 43

5-Benzyloxy-2-(4-benzyloxyphenyl)-1-ethyl-3-((5-piperidinopentyloxy)methyl)-pyrrolo [2,1,5- cd]indolizine 5-Benzyloxy-2-(4-benzyloxyphenyl)-3-((5-chloropentyloxy)methyl)-1-ethylpyrrolo[2,1,5-cd]indolizine (0.41 g, 0.69 mmol) was dissolved in 50 ml of dry dimethylformamide under a nitrogen atmosphere. Sodium hydride (60% in oil) (0.40 g, 10 mmol) and piperidine (0.93 g, 11mmol) was added, and the mixture was stirred at 60° for 5 days. Ethanol (10 ml) was added dropwise, and the reaction mixture was diluted with 200 ml of water. The organic material was extracted into ethyl acetate (3×100 ml), and the combined organic layers were washed with brine and dried over sodium sulfate. The solvent was evaporated and the crude produce was purified by column chromatography over silica gel 60, using 10% of methanol in dichloromethane as the eluent. Fractions containing the product were collected and crystallised from diethyl ether and dichloromethane to afford 161 mg (36%) of 5-benzyloxy-2-(4-benzyloxyphenyl)-1-ethyl-3-((5-piperidinopentyloxy)methyl)pyrrolo[2,1,5-cd]indolizine as yellow crystals. M.p. 106–107° C. MS(SP): m/z 627 (M+1). $^1$H-NMR (DMSO-$d_6$, 300 MHz) δ: 1.16–1.75 (m, 15H); 2.61–2.95 (m, 4H); 3.07 (q, 2H); 3.21–3.24 (m, 4H); 4.71 (s, 2H); 5.20 (s, 2H); 5.56 (s, 2,H); 7.30–7.64 (m, 14H); 7.99 (d, 1H).

EXAMPLE 44

5-Benzyloxy-2-(4-benzyloxyphenyl)-1-ethyl-3-((4-piperidinobutoxy)methyl)-pyrrolo[2,1,5-cd]indolizine Piperidine (0.104 g, 1.22 mmol) was dissolved in 50 ml of dry dimethylformamide under a nitrogen atmosphere and sodium hydride (60% in oil) 47 mg, 1.16 mmol) was added. The mixture was stirred for ½ hour. 5-Benzyloxy-2-(4-benzyloxyphenyl)-3-((4-chlorobutoxy)methyl)-1-ethylpyrrolo[2,1,5-cd]indolizine (0.337 g, 0.583 mmol) was added and the mixture was stirred at 55–65° for 7 days.

Ethanol (10 ml) was added dropwise, and the reaction mxiture was diluted with 250 ml of water. The organic material was extracted into ethyl acetate (3×100 ml), and the combined organic layers were washed with brine and dried over sodium sulfate. The solvent was eaporated and the crude product was purified by column chromatography over silica gel 60, using 5% of methanol in dichloromethane as the eluent. Fractions containing the product were collected to afford 21 mg (5%) of 5-benzyloxy-2-(4-benzyloxyphenyl)-1-ethyl-3-((4-piperidinobutoxy)methyl) pyrrolo[2,1,5-cd]indolizine as an oil. MS(SP): m/z 640 (M+). $^1$H-NMR (DMSO-$d_6$, 300 MHz) δ: 1.28–1.58 (m, 13H); 2.21–2.57 (m, 6H); 3.08 (q, 2H); 3.37–3.48 (m, 2H+H$_2$O); 4.72 (s, 2H); 5.20 (s, 2H); 5.60 (s, 2H); 7.22 (d, 2H); 7.32–7.69 (m, 14H); 7.98 (d, 1H).

EXAMPLE 45

5-Benzyloxy-2-(4-benzyloxyphenyl)-1-ethyl-3-((4-pyrrolidinobutoxy)methyl)-pyrrolo[2,1,5-cd]indolizine Pyrrolidine (66 mg, 0.93 mmol) was dissolved in 50 ml of dry dimethylformamide under a nitrogen atmosphere and sodium hydride (60% in oil) (36 mg, 0.89 mmol) was added. The mixture was stirred for ½ hour. 5Benzyloxy-2-(4-benzyloxyphenyl)-3-((4-chlorobutoxy)methyl)-1-ethylpyrrolo[2,1,5-cd]indolizine (0.256 g, 0.443 mmol) was added and the mixture was stirred at 55–65° for 6 days. Ethanol (10 ml) was added dropwise, and the reaction mixture was diluted with 250 ml of water. The organic material was extacted into ethyl acetate (4×100 ml), and the combined oranic layers were washed with brine and dried over sodium solfate. The solvent was evaporated and the crude product was purified by column chromatography over silica gel 60, using 6% of methanol in dichloromethane as the eluent. Fractions contaiing the product were collected to afford 34 mg (12%) of 5-benzyloxy-2-(4-benzyloxyphenyl)-1-ethyl-3-((4-pyrrolidinobutoxy)methyl)pyrrolo[2,1,5-cd]indolizine as an oil. MS(FAB): m/z613 (M+1). $^1$H-NMR (DMSO-$d_6$, 300 MHz) δ: 1.27–1.49 (m, 11H); 2.50–2.56 (m, 6H); 3.05 (q, 2H); 3.40 (t, 2H); 4.71 (s, 2H); 5.20 (s, 2H); 5.58 (s, 2H); 7.20 (d, 2H); 7.31–7.64 (m, 14H); 7.95 (d, 1H).

EXAMPLE 46

5-Benzyloxy-2-(4-benzyloxyphenyl)-3-((but-3-enyloxy)methyl)-1-ethylpyrrolo[2,1,5-cd]indolizine Piperidine (0.14 g, 1.22 mmol) was dissolved in 50 ml of dry dimethylformamide under a nitrogen atmosphere and sodium hydride (60% in oil) (47 mg, 1.16 mmol) was added. The mixture was stirred for ½ hour. 5-Benzyloxy-2-(4-benzyloxyphenyl)-3-((4-chlorobutoxy)methyl)-1-ethylpyrrolo[2,1,5-cd]indolizine (0.337 g, 0.583 mmol) was added and the mixture was stirred at 55–64° for 7 days. Ethanol (10 ml) was added dropwise, and the reaction mixture was diluted with 250 ml of water. The organic material was extracted into ethyl acetate (3×100 ml), and the combined organic layers were washed with brine and dried over sodium sulfate. The solvent was evaporated and the crude product was purified by column chromatography over silica gel 60, using 5% of methanol in dichloromethane as the eluent. Fractions contaiing the product wre collected to afford 165 mg (52%) of 5-benzyloxy-2-(4-benzyloxyphenyl)-3-((but-3-enyloxy)methyl)-1-ethylpyrrolo[2,1,5-cd]indolizine as an oil. MS(SP): m/z 541 (M+). $^1$H-NMR (DMSO-$d_6$, 300 MHz) δ: 1.33 (t, 3H); 2.18 (m, 2H); 3.05 (q, 2H); 3.43 (t, 2H); 4.71 (s, 2H); 4.93–5.07 (m, 2H); 5.19 (s, 2H); 5.58 (s, 2H); 5.72 (m, 1H); 7.18 (d, 2H); 7.30–7.62 (m, 14H); 7.98 (d, 1H).

EXAMPLE 47

1-Ethyl-5-hydroxy-2-(4-hydroxyphenyl)-3-(8-piperidinooctyloxy)methyl)pyrrolo[2,1,5-cd]indolizine A suspension of 5-benzyloxy-2-(4-benzyloxyphenyl)-1-ethyl-3-((8-piperidinooctyloxy)-methyl)pyrrolo[2,1,5-cd]indolizine (0.30 g, 0.44 mmol) and 30 mg 10% palladium on charcoal in 12 ml of ethanol and 8 ml of tetrahydrofuran was stirred in a hydrogen atmosphere for 6 hours. The reaction mixture was filtered twice and the solvent was evaporated. The resulting oil was purified by column chromatography over netural aluminium oxide activity grade I, using 10% of methanol in dichloromethane as the eluent. The product was crystallised from dichloromethane, diethyl ether and petroleum ether to afford 189 mg (85%) of 1-ethyl-5-hydroxy-2-(4-hydroxyphenyl)-3-((8-piperidinooctyloxy)methyl)pyrrolo[2,1,5-cd]indolizine as yellow crystals. M.p. 91–95° C. (decomp.). MS(FAB): m/z 503 (M+1). $^1$H-NMR (DMSO-$d_6$, 300 MHz) δ:1.17–1.71 (m, 21H); 2.61–3.09 (m, 8H); 3.38 (t, 2H); 4.68 (s, 2H); 6.92 (d, 2H); 7.12 (d, 1H); 7.22 (s, 1H); 7.48 (d, 2H); 7.83 (d, 1H); 9.58 (s, 1H); 10.59 (s, 1H).

EXAMPLE 48

1-Ethyl-5-hydroxy-2-(4-hydroxyphenyl)-3-methoxymethylpyrrolo[2,1,5-cd]indolizine 5-Benzyloxy-2-(4-benzyloxyphenyl)-1-ethyl-3-methoxymethylpyrrolo[2,1,5-cd]indolizine wash hydrogenated by the general synthetic principles outlined in example 47, to afford 1-ethyl-5-hydroxy-2-(4-hydroxyphenyl)-3-methoxymethylpyrrolo[2,1,5-cd]indolizine as brown crystals in 98% yield. M.p. 60–80° C. (decomp.). MS(SP): m/z 321 (M+). $^1$H-NMR (DMSO-$d_6$, 200 MHz) δ: 1.32 (t, 3H); 3.303 (q, 2H); 3.27 (s, 3H); 4.65 (s, 2H); 6.92 (d, 2H); 7.12 (d, 1H); 7.22 (s, 1H); 7.48 (d, 2H); 7.83 (d, 1H).

EXAMPLE 49

1-Ethyl-2-(4-hydroxyphenyl)-3-((2-piperidinoethoxy)methyl)pyrrolo[2,1,5-cd]indolizine 2-(4-Benzyloxyphenyl)-1-ethyl-3-((2-piperidinoethyoxy)methyl)pyrrolo[2,1,5-cd]indolizine was hydrogenated by the general synthetic principles outlined in example 47, to afford 1-ethyl-2-(4-hydroxyphenyl)-3-((2-piperidinoethyoxy)methyl)pyrrolo[2,1,5-cd]indolizine as yellow crystal. M.p. 154–158° C. MS(SP): m/z 402 (M+). $^1$H-NMR (DMSO-$d_6$, 300 MHz) δ: 1.26–1.41 (m, 4H); 1.53–1.80 (m, 5H); 2.70–2.89 (m, 2H); 3.05–3.21(m, 4H); 3.24–3.32 (m, 2H); 3.72 (t, 2H); 4.91 (s, 2H); 6.99 (d, 2H); 7.29 (s, 1H); 7.52 (d, 2H); 7.72 (t, 1H); 8.02 (d, 1H); 8.11 (d, 1H); 9.70 (s, 1H).

EXAMPLE 50

1-Ethyl-5-hydroxy-2-(4-hydroxyphenyl)-3-((2-piperidinoethoxy)methyl)pyrrolo[2,1,5-cd]indolizine 5-Benzyloxy-2-(4-benzyloxyphenyl)-1-ethyl-3-((2-piperidinoethoxy)methyl)pyrrolo[2,1,5-cd]indolizine was hydrogenated by the general synthetic princples outlined in example 47, to afford 1-ethyl-5-hydroxy-2-(4-hydroxyphenyl)-3-((2-piperidinoethoxy)methyl)pyrrolo[2,1,5-cd]indolizine as yellow crystals in 73% yield. M.p. ca 160° C. (decomp.). MS(FAB): m/z 419 (M+1). $^1$H-NMR (DMSO-$d_6$, 300 MHz) δ: 1.25–1.38 (m, 5H); 1.39–1.48 (m, 4H); 2.27–2.40 (m, 6H); 3.02 (q, 2H); 3.50 (t, 2H); 4.69 (s, 2H); 6.92 (d, 2H); 7.11 (d, 1H); 7.22 (s, 1H); 7.48 (d, 2H); 7.83 (d, 1H); 9.57 (s, 1H); 10.65 (s, 1H).

EXAMPLE 51
1-Ethyl-5-hydroxy-2-(4-hydroxyphenyl)-3-((3-piperidinopropoxy)methyl)pyrrolo[2,1,5-cd]indolizine 5-Benzyloxy-2-(4-benzyloxyphenyl)-1-ethyl-3-((3-piperidinopropoxy)methyl)pyrrolo[2,1,5-cd]indolizine was hydrogenated by the general synthetic princples outlined in example 47, to afford 1-ethyl-5-hydroxy-2-(4-hydroxyphenyl)-3-((3-piperidinopropoxy)methylpyrrolo[2,1,5-cd]indolizine as yellow crystals in 70% yield. M.p. ca 127° C. (decomp.). MS(FAB): m/z 433 (M+1). $^1$H-NMR (DMSO-$d_6$, 300 MHz) δ: 1.23–1.49 (m, 9H); 1.58 (quintet, 2H); 2.17–2.29 (m, 6H); 3.02 (q, 2H); 3.42 (t, 2H); 4.68 (s, 2H); 6.91 (d, 2H); 7.12 (d, 1H); 7.21 (s, 1H); 7.48 (d, 2H); 7.82 (d, 1H); 9.59 (s, 1H); 10.61 (s, 1H).

EXAMPLE 52
1-Ethyl-5-hydroxy-2-phenyl-3-((2-piperidinoethoxy)methyl)pyrrolo[2,1,5-cd]indolizine 5-Benzyloxy-1-ethyl-2-phenyl-3-((2-piperidinoethoxy)methyl)pyrrolo[2,1,5-cd]indolizine was hydrogenated by the general synthetic principles outlined in example 47, to afford 1-ethyl-5-hydroxy-2-phenyl-3-((2-piperidinoethoxy)methyl)pyrrolo[2,1,5-cd]indolizine as yellow crystals in 93% yield. M.p. 196–198° C. MS(SP): m/z 402 (M+). $^1$H-NMR (DMSO-$d_6$, 300 MHz) δ: 1.27–1.38 (m, 4H); 1.57–1.76 (m, 5H); 2.70–2.85 (m, 2H); 3.02–3.13 (m, 4H); 3.21–3.31 (m, 2H); 3.69 (t, 2H); 4.82 (s, 2H); 7.18 (d, 1H); 7.32 (s, 1H); 7.39–7.69 (m, 5H); 7.93 (d, 1H); 10.82 (s, 1H).

EXAMPLE 53
1-Ethyl-5-hydroxy-2-phenyl-3-((3-piperidinopropoxy)methyl)pyrrolo[2,1,5-cd]indolizine 5-Benzyloxy-1-ethyl-2-phenyl-3-((3-piperidinopropoxy)methyl)pyrrolo[2,1,5-cd]indolizine was hydrogenated by the general synthetic princples outlined in example 47, to afford 1-ethyl-5-hydroxy-2-phenyl-3-((3-piperidinopropoxy)methyl)pyrrolo[2,1,5-cd]indolizine as a yellow foam in 69% yield. M.p. 93–99° C. MS(SP): m/z 416 (M+). $^1$H-NMR (DMSO-$d_6$, 300 MHz) δ: 1.28–1.49 (m, 9H); 1.54 (quintet, 2H); 2.12–2.28 (m, 6H); 3.07 (q, 2H); 3.35 (t, 2H); 4.68 (s, 2H); 7.14 (d, 1H); 7.25 (s, 1H); 7.37–7.69 (m, 5H); 7.90 (d, 1H); 10.71 (s, 1H).

EXAMPLE 54
1-Ethyl-5-hydroxy-2-(4-hydroxyphenyl)-3-((5-methoxypentyloxy)methyl)pyrrolo[2,1,5-cd]indolizine 5-Benzyloxy-2-(4-benzyloxyphenyl)-1-ethyl-3-((5-methoxypentyloxy)methyl)pyrrolo [2,1,5-cd]indolizine was hydrogenated by the general synthetic principles outlined in exmaple 47, to afford 1-ethyl-5-hydroxy-2-(4-hydroxyphenyl)-3-((5-methoxypentyloxy)methyl)pyrrolo[2,1,5-cd]indolizine as an oil in 50% yield. MS(SP): m/z 407 (M+). $^1$H-NMR (DMSO-$d_6$, 300 MHz) δ: 1.21–1.37 (m, 5H): 1.39–1.51 (m, 4H); 3.03 (q, 2H); 3.18 (s, 3H); 3.26 (t, 2H); 3.39 (t, 2H); 4.68 (s, 2H); 6.92 (d, 2H); 7.12 (d, 1H); 7.22 (s, 1H); 7.48 (d, 2H); 7.82 (d, 2H); 9.56 (s, 1H); 10.62 (s, 1H).

EXAMPLE 55
1-Ethyl-2-(4-hydroxyphenyl)-3-methoxymethylpyrrolo[2,1,5-cd]indolizine 2-(4-Benzyloxphenyl)-1-ethyl-3-methoxmethylpyrrolo[2,1,5-cd]indolizine was hydrogenated by the general synthetic princples outlined in example 47, to afford 1-ethyl-2-(4-hydroxyphenyl)-3-methoxymethylpyrrolo[2,1,5-cd]indolizine as an organge amorphous solid in 64% yield. M.p.>130° C. MS(SP): m/z 305 (M+). $^1$H-NMR (CDCl$_3$, 300 MHz) δ: 1.41(t, 3H); 3.13 (q, 2H); 3.40 (s, 3H); 4.81 (s, 2H); 6.94 (d, 2H); 7.21 (s, 1H); 7.55 (d, 2H); 7.62 (dd, 1H); 7.89 (m, 2H).

EXAMPLE 56
1-Ethyl-5-hydroxy-2-(4-hydroxyphenyl)-3-((6-piperidinohexyloxy)methyl)pyrrolo[2,1,5-cd]indolizine 5-Benzyloxy-2-(4-benzyloxyphenyl)-1-ethyl-3-((6-piperidinohexyloxy)methyl)pyrrolo [2,1,5-cd]indolizine was hydrogenated by the general synthetic princples outlined in example 47, to afford 1-ethyl-5-hydroxy-2-(4-hydroxyphenyl)-3-((6-piperidinohexyloxy)methyl)pyrrolo [2,1,5-cd]indolizine as yellow crystals in 64% yield. M.p. 129–131° C. MS(FAB): m/z 475 (M+1). $^1$H-NMR (DMSO-$d_6$, 300 MHz) δ: 1.14–1.50 (m, 17H); 2.12 (t, 2H); 2.18–2.30 (m, 4H); 3.02 (q, 2H); 3.38 (t, 2H); 4.65 (s, 2H); 6.90 (d, 2H); 7.10 (d, 1H); 7.20 (s, 1H); 7.48 (d, 2H); 7.81 (d, 1H).

EXAMPLE 57
2-(4-Hydroxyphenyl)-3-methoxymethylpyrrolo[2,1,5-cd]indolizine 2-(4-benzyloxyphenyl)-3-methoxymethylpyrrolo[2,1,15-cd]indolizine was hydrogenated by the general synthetic principles outlined in exmaple 47, to afford 2-(4-hydroxyphenyl)-3-methoxymethylpyrrolo[2,1,5-cd]indolizine as a red oil in 86% yield. MS(SP): m/z 277 (M+). $^1$H-NMR (DMSO-$d_6$, 200 MHz) δ: 3.43 (s, 3H); 4.91 (s, 2H); 6.99 (d, 2H); 7.33 (s, 1H); 7.43 (s, 1H); 7.74 (t, 1H); 7.87 (d, 2H); 7.99 (d, 2H); 9.78 (s, 1H).

EXAMPLE 58
1-Ethyl-5-hydroxy-2-(4-hydroxyphenyl)-3-((5-piperidinopentyloxy)methyl)pyrrolo[2,1,5-cd]indolizine 5-Benzyloxy-2-(4-benzyloxyphenyl)-1-ethyl-3-((5-piperidinopentyloxy)methyl)pyrrolo[2,1,5-cd]indolizine was hydrogenated by the general synthetic principles outlined in example 47, to afford 1-ethyl-5-hydroxy-2-(4-hydroxyphenyl)-3-((5-piperidinopentyloxy)methyl)-pyrrolo[2,1,5-cd]indolizine as yellow crystals in 54% yield. M.p. 120–121° C. MS(FAB): m/z 461 (M+1). $^1$H-NMR (DMSO-$d_6$, 300 MHz)δ: 1.17–1.50 (m, 15H); 2.13 (t, 2H); 2.18–2.28 (m, 4H); 3.02 (q, 2H); 3.38 (t, 2H); 4.66 (s, 2H); 6.90 (d, 2H); 7.10 (d, 1H); 7.20 (s, 1H); 7.48 (d, 2H); 7.82 (d, 1H).

EXAMPLE 59
1-Ethyl-3-hydroxymethyl-2-(4-hydroxyphenyl)pyrrolo[2,1,5-cd]indolizine 2-(4-Benzyloxyphenyl)-1-ethyl-3-hydroxymethylpyrrolo[2,1,5-cd]indolizine was hydrogenated by the general synthetic principles outlined in example 47, to afford 1-ethyl-3-hydroxymethyl-2-(4-hydroxyphenyl)pyrrolo[2,1,5-cd]indolizine as a yellow solid in 78% yield. MS(SP: m/z 291 (M+). $^1$H-NMR (DMSO-$d_6$, 200 MHz)δ: 1.35 (t, 3H); 3.10 (q, 2H); 4.85 (s, 2H); 5.27 br s, 1H); 6.96 (d, 2H); 7.23 (s, 1H); 7.52 (d, 2H); 7.68 (t, 1H); 7.96 (d, 1H); 8.04 (d, 1H); 9.70 (br s, 1H).

EXAMPLE 60
3-Hydroxymethyl-2-(4-hydroxyphenyl)pyrrolo[2,1,5-cd]indolizine 2-(4-Benzyloxyphenyl)-3-hydroxymethylpyrrolo[2,1,5-cd]indolizine was hydrogenated by the general synthetic principles outlined in example 47, to afford 3-hydroxymethyl-2-(4-hydroxyphenyl)pyrrolo[2,1,5-cd]indolizine as yellow crystals in 86% yield. M.p. 185–190° C. $^1$H-NMR (DMSL-$d_6$, 200 MHz)δ: 5.04 (s, 2H); 5.48 (br s, 1H); 6.93 (d, 2H); 7.32 (s, 1H); 7.40 (s, 1H); 7.71 (t, 1H); 7.86 (d, 2H); 7.97 (d, 2H); 9.70 (br s, 1H).

EXAMPLE 61

1-Ethyl-5-hydroxy-3-hydroxymethyl-2-(4-hydroxyphenyl)pyrrolo[2,1,5-cd]indolizine 5-Benzyloxy-2-(4-benzyloxyphenyl)-1-ethyl-3-hydroxymethylpyrrolo[2,1,5-cd]indolizine was hydrogenated by the general synthetic principles outlined in example 63, to afford 1-ethyl-5-hydroxy-3-hydroxymethyl-2-(4-hydroxyphenyl)pyrrolo[2,1,5-cd]indolizine as yellow crystals in 103% yield. M.p 155–160° C. $^1$H-NMR (DMSO-$d_6$, 200 MHz)δ: 1.32 (t, 3H); 3.02 (q, 2H); 4.80 (s, 2H); 6.92 (d, 2H); 7.11 (d, 1H); 7.25 (s, 1H); 7.48 (d, 2H); 7.79 (d, 1H); 9.95 (br s, 1H).

EXAMPLE 62

2-[(2-Dimethylaminoethyl)methylcarbamoyl]-4-ethyl-6-methoxy-3-(4-methoxyphenyl)-pyrrolo[2,1,5-cd]indolizine-1-carboxylic acid Step 1:

2-n-Propylpyridine-N-oxide

To a solution of 2-n-propylpyridine (187.4 g, 1.505 mol) in 900 ml of acetic acid was added 149 ml of 35% aqueous hydrogen peroxide and the mixture was stirred and heated to 70–80° C. After three hours a further 104 ml of the hydrogen peroxide solution was added, and the mixture was maintained at the same temperature for an additional nine hours. The mixture was concentrated to about 300 ml in volume, 300 ml of water was added, and the mixture was concentrated as far as possible. The residue was made alkaline with anhydrous sodium carbonate, shaken with 750 ml of dichloromethane, and allowed to stand overnight. The resulting deposit of sodium carbonate and sodium acetate was removed by filtration. The filtrate was dried over magnesium sulfate, the solvent removed, and the residue distilled under reduced pressure. This gave 176 g (81%) of 2-n-propylpyridine-N-oxide. B.p. 120–140° C./9–15 mbar. $^1$H-NMR (CDCl$_3$, 200 MHz) δ: 1.05 (t, 3H); 1.80 (sext, 2H); 2.89 (t, 2H); 7.10–7.28 (m, 3H); 8.28 (d, 1H).

Step 2:

4-Nitro-2-n-propylpyridine-N-oxide

A mixture of 2-n-propylpyridine-N-oxide (137.2 g, 1.0 mol) in 200 ml of sulfuric acid (sp. gr. 1.84) was stirred in an ice-salt bath and 320 ml of nitric acid (sp. gr. 1.52) was added. The mixture was carefully heated to 70–72° C. and reacted for 22 hours. The reaction mixture was cooled and poured onto ice and, with stirring, neutralized with portions of sodium carbonate (500 g). The resulting precipitate was collected, washed with water and dried. The dried substance was slurred in 1 liter of dichloromethane and anhydrous sodium sulfate was added. The mixture was filtered and the solvent was evaporated. The yellow residue from evaporation of the dichloromethane solution was dried to afford 89.2 g (49%) of 4-nitro-2-n-propylpyridine-N-oxide. M.p. 89–91° C. $^1$H-NMR (CDCl$_3$, 200 MHz) δ: 1.10 (t, 3H); 1.70 (sext, 2H); 2.94 (t, 2H); 7.96 (dd, 1H); 8.08 (dd, 1H); 8.30 (dd, 1H).

Step 3:

4-Methoxy-2-n-propylpyridine-N-oxide

A solution of 4-nitro-2-n-propylpyridine-N-oxide (146.0 g, 0.8 mol) in 500 ml of anhydrous methanol was stirred and 190 ml of a 4.6 M methanolic sodium methoxide solution was added dropwise. When the addition was complete, the mixture was stirred for three hours. The precipitated sodium nitrite was filtered off and washed with methanol. The filtrate was evaporated and the residue was stirred with 300 ml of dichloromethane. The mixture was filtered and evaporated to afford 129 g (97%) of 4-methoxy-2-n-propylpyridine-N-oxide as an oil. $^1$H-NMR (CDCl$_3$, 200 MHz) δ: 1.07 (t, 3H); 1.80 (sext, 2H); 2.80 (t, 2H); 3.87 (s, 3H); 6.66–6.78 (m, 2H); 8.17 (d, 2H).

Step 4:

4-Methoxy-2-n-propylpyridine

A solution of 4-methoxy-2-n-propylpyridine-N-oxide (59.3 g, 0.355 mol) in 800 ml of 1 M sulfuric acid was stirred and heated to 70–80° C. Zinc dust (140.0 g, 214 mol) was added in portions over four hours. When the addition was complete, heating was continued for a further eight hours. The resulting precipitate was filtered off and washed with water. The filtrate was made strongly alkaline by addition of a 32% sodium hydroxide solution and extracted with dichloromethane (3×250 ml). The extracts were combined, dried over sodium sulfate, filtered, evaporated and distilled. This gave 46.1 g (86%) of 4-methoxy-2-n-propylpyridine as a colourless oil. B.p. 44–46° C./0.1–0.2 mbar. $^1$H-NMR (CDCl$_3$, 200 MHz) δ: 0.99 (t, 3H); 1.75 (sext, 2H); 2.72 (t, 2H); 3.81 (s, 3H); 6.10–6.18 (m, 2H); 8.35 (d, 1H).

Step 5:

1-Ethyl-7-methoxy-2-(4-methoxyphenyl)indolizine

4-Methoxy-2-n-propylpyridine was reacted with 4-methoxyphenacylbromide by the general synthetic principle outlined in example 23, step 5, to afford 1-ethyl-7-methoxy-2-(4-methoxyphenyl)indolizine in 86% yield. M.p. 101–103° C. $^1$H-NMR (DMSO-$d_6$, 200 MHz) δ: 1.10 (t, 3H); 2.77 (q, 2H); 3.77 (s, 3H); 3.80 (s, 3H); 6.23 (dd, 1H); 6.65 (d, 1H); 7.00 (d, 2H); 7.35 (s, 1H); 7.38 (d, 2H); 8.06 (d, 1H). Analysis: Calculated for $C_{18}H_{19}N_1O_2$: C, 76.84; H, 6.81; N, 4.98%. Found: C, 76.73; H, 6.94; N, 4.80%.

Step 6:

Dimethyl 4-Ethyl-6-methoxy-3-(4-methoxyphenyl)pyrrolo[2,1,5-cd]indolizine-12,2-di carboxylate 1-7-methoxy-2-(4-methoxyphenyl)indolizine was reacted with dimethyl acetylene di-carboxylate by the general synthetic principle outlined in example 23, step 6, to afford Dimethyl 4-Ethyl-6-methoxy-3-(4-methoxyphenyl)pyrrolo[2,1,5-cd]indolizine-1,2-dicarboxylate in 92% yield. M.p. 153–155° C. $^1$H-NMR (DMSO-$d_6$, 200 MHz) δ: 1.36 (t, 3H); 3.07 (q, 2H); 3.76 (s, 3H); 3.86 (s, 3H); 3.89 (s, 3H); 4.10 (s, 3H); 7.15 (d, 2H); 7.53 (d, 2H); 7.84 (d, 1H); 8.00 (d, 1H). Analysis: Calculated for $C_{24}H_{23}N_1O_6$: C, 68.40; H 5.50; N, 3.32%. Found: C, 68.48; H, 5.64; N, 3.27%.

Step 7:

4-Ethyl-6-methoxy-3-(4-methoxyphenyl)pyrrolo[2,1,5-cd]indolizine-1,2-dicarboxylic acid Dimethyl 4-Ethyl-6-methoxy-3-(4-methoxyphenyl)pyrrolo[2,1,5-cd]indolizine-1,2-dicarboxylate was hydrolysed by the general synthetic principle outlined in example 23, step 7, to afford 4-ethyl-6-methoxy-3-(4-methoxyphenyl)pyrrolo[2,1,5-cd]indolizine-1,2-dicarboxylic acid in 95% yield. M.p. 209–211° C. $^1$H-NMR (DMSO-$d_6$, 200 MHz) δ: 1.34 (t, 3H); 3.00 (q, 2H); 3.85 (s, 3H); 4.08 (s, 3H); 7.10 (d, 2H); 7.55 (d, 2H); 7.85 (d, 1H);

7.94 (d, 1H). Analysis: Calculated for $C_{22}H_{19}N_1O_6$, 0.5 $H_2O$: C, 65.67; H, 5.01; N, 3.48%. Found: C, 65.80; H, 5.16; N, 3.20%.

Step 8:

4-Ethyl-6-methoxy-3-(4-methoxyphenyl)pyrrolo[2,1 5-cd]indolizine-1,2-dicarboxylic acid anhydride 4-Ethyl-6-methoxy-3-(4-methoxyphenyl)pyrrolo[2,1,5-cd]indolizine-1,2-dicarboxylic acid was dehydrated by the general synthetic principles outlined in example 23, step 8, to afford 4-Ethyl-6-methoxy-3-(4-methoxyphenyl)pyrrolo[2,1,5-cd]indolizine-1,2-dicarboxylic acid anhydride as yellow crystals in 58% yield. M.p. 249–251° C. HPLC (eluent: 65% $CH_3CN$ isocratic, 35% buffer $H_3PO_4$ pH=3): Rt=18.02 min (100% purity). $^1$H-NMR (CDCl$_3$, 200 MHz) δ: 1.48 (t, 3H); 3.17 (q, 2H); 3.91 (s, 3H); 4.09 (s, 3H); 7.13 (d, 2H); 7.62 (s, 2H); 7.84 (d, 2).

Step 9:

2-[(2-Dimethylaminoethyl)methylcarbamoyl]-4-ethyl-6-methoxy-3-(4-methoxyphenyl)pyrrolo[2,1,5-cd]indolizine-1-carboxylic acid A suspension of 4-ethyl-6-methoxy-3-(4-methoxyphenyl)pyrrolo[2,1,5-cd]indolizine-1,2-dicarboxylic acid anhydride (1,5 g, 4 mmol) in 50 ml of dichloromethane, was added to a 0° solution of N,N,N'-triethylenediamine (5ml, 40 mmol). The reaction mixture was allowed to heat to room temperature, and stirred for 4 hours whereas the solvent was evaporated. 25 ml of water was added and pH was adjusted to pH=5 with acetic acid. The solution was stored in the refrigerator for 12 hours whereas a yellow precipitate appeared, which was filtered off and washed with water. This gave 1.73 g (90%) of the title compound as green crystals. M.p. 221–223° C. HPLC (eluent: 65% $CH_3CN$ isocratic, 35% buffer $H_3PO_4$ pH=3): Rt=8.91 min (96% purity). $^1$H-NMR (CDCl$_3$, 200 MHz) δ: 1.42 (t, 3H); 2.82 (s, 3H); 2.92 (s, 6H); 2.95–3.38 (m, 6H); 3.89 (s, 3H); 4.10 (s, 3H); 7.02 (d, 2H); 7.50–7.61 (m, 3H); 8.11 (d, 1H).

EXAMPLE 63

2-[(2-Dimethylaminoethyl)methylcarbamoyl]-4-ethyl-3-(4-methoxyphenyl)pyrrolo[2,1,5-cd]indolizine-1-carboxylic acid 4-Ethyl-3-(4-methoxyphenyl)pyrrolo[2,1,5-cd]indolizine-1,2-dicarboxylic acid anhydride (obtained in analogy with synthetic principles outlined in example 62, step 1–8) was aminolysed by the general synthetic principles outlined in example 62, step 9, to afford 2-[(2-dimethylaminoethyl)methylcarbamoyl]-4-ethyl-3-(4-methoxyphenyl)pyrrolo[2,1,5-cd]indolizine-1-carboxylic acid as crystals in 87% yield. HPLC (eluent: 65% $CH_3CN$ isocratic, 35% buffer $H_3PO_4$ pH=3): Rt=7.32 min (95%) purity. $^1$H-NMR (DMSO-d$_6$, 200 MHz) δ: 1.39 (t, 3H); 1.72 (s, 3H); 1.89–3.90 (m, 15H); 7.11 (d, 2H); 7.58 (d, 2H); 7.94 (dd, 1H); 8.22 (d, 2H); 8.37 (d, 2H).

EXAMPLE 64

2-[(2-Dimethylaminoethyl)methylcarbamoyl]-4-ethyl-6-methoxy-3-(4-methoyxphenyl)-pyrrolo[2,1,5-cd]indolizine 2-[(2-Dimethylaminoethyl)methylcarbamoyl]-4-ethyl-6-methoxy-3-(4-methoxyphenyl)-pyrrolo[2,1,5-cd]indolizine-1-carboxylic was decarboxylated by the general synthetic principles outlined in example 33, step 10 to afford 2-[(2-dimethylaminoethyl)-methylcarbamoyl]-4-ethyl-6-methoxy-3-(4-methoxyphenyl)pyrrolo[2,1,5-cd]indolizine as green crystals in 55% yield. M.p. 206–209° C. HPLC (eluent: 65% $CH_3CN$ isocratic, 35% buffer $H_3PO_4$ pH=3): Rt=10.04 min (95% purity). $^1$H-NMR (CDCl$_3$, 200 MHz) δ: 1.40 (t, 3H); 2.67 (s, 3H); 2.87 (s, 6H); 3.01–3.16 (m, 4H); 3.81–3.93 (m, 5H); 4.04 (s, 3H);l 7.01 (d, 2H); 7.12 (s, 1H); 7.45–7.61 (m, 4H). The structure has been proven by COSY, ROESY and NOESY, 400 MHz.

EXAMPLE 65

2-[(2-Dimethylaminoethyl)methylcarbamoyl]-4-ethyl-3(4-methoxyphenyl)pyrrolo[2,1,5-cd]indolizine 2-[(2-Dimethylaminoethyl)methylcarbamoyl]-4-ethyl-3-(4-methoxyphenyl)pyrrolo[2,1,5-cd]indolizine-1-carboxylic acid was decarboxylated by the general synthetic principles outlined in example 33, step 10 to afford 2-[(2-dimethylaminoethyl)methylcarbamoyl]-4-ethyl-3-(4-methoxyphenyl)pyrrolo[2,1,5-cd]indolizine as an oil in 5% yield. HPLC (eluent: MeOH isocratic 90%, buffer DEA): Rt=3.91 min (94% purity). $^1$H-NMR (CDCl$_3$, 200 MHz) δ: 1.44 (t, 3H); 1.85 (s, 3H); 2.03 (t, 1H); 2.31 (s, 3H); 2.44 (t, 1H); 2.56 (s, 2H); 2.96–3.06 (m, 2H); 3.20 (m, 2H); 3.52 (t, 1H); 3.88 (s, 3H); 7.03 (d, 1H); 7.32 (d, 1H); 7.52–7.72 (m, 3H); 7.95 (m, 2H).

EXAMPLE 66

2-[(2-Dimethylaminoethyl)methylcarbamoyl]-4-ethyl-3-(4-hydroxyphenyl)-6-methoxypyrrolo[2,1,5-cd]indolizine 2-[(2-diemthylaminoethyl)methylcarbamoyl]-4-ethyl-6-methoxy-3-(4-methoxyphenyl)-pyrrolo[2,1,5-cd]indolizine (0.2 g, 0.460 mmol) was dissolved in 15 ml of dichloromethane under a nitrogen atmosphere and cooled to −78° C. 1 M borontribromide in dichloromethane (2.8 ml, 2.8 mmol) was added dropwise. The mixture was allowed to reach room temperature and stirred for 3 days. The reaction mixture was poured into 100 ml of saturated aqueous sodium hydrogen carbonate and the pH was adjusted to 7 with 4 N hydrochloric acid. The organic material was extracted into diethyl ether (2×100 ml). The combined organic layers were dried over magnesium sulfate, and evaporated to give yellow brown crystals, which was purified by column chromatography over silica gel 60, using 20% of methanol in di-chloromethane as the eluent. Fractions containing the product were collected and the solvent was evaporated. The crude product was crystallised from dichloromethane and petroleum ether to afford 50 mg (26%) of 2-[(2-dimethylaminoethyl)methylcarbamoyl]-4-ethyl-3-(4-hydroxyphenyl)-6-methoxypyrrolo[2,1,5-cd]indolizine. M.p. 190–200° C. $^1$H-NMR (DMSO-d$_6$, 200 MHz) δ: 1.33 (t, 3H); 1.74 (s, 3H); 1.87 (s, 3H); 2.01 (t, 1H); 2.18 (s, 3H); 2.33 (t, 1H); 2.92–3.20 (m, 3H); 3.41 (t, 1H); 4.02 (s, 3H); 6.91 (d, 2H); 7.08 (s, 1H); 7.40 (d, 2H); 7.71 (s, 1H); 7.81 (s, 1H).

EXAMPLE 67

2-[(2-Dimethylaminoethyl)methylcarbamoyl]-4-ethyl-3-(4-hydroxyphenyl)pyrrolo[2,1,5-cd]indolizine 2-[(2-Dimethylaminoethyl)methylcarbamoyl]-4-ethyl-3-(4-methoxyphenyl)pyrrolo[2,1,5-cd]indolizine was demethylated by the general synthetic principles outlined in example 66, to afford 2- [(2-dimethylaminoethyl) methylcarbamoyl]-4-ethyl-3-(4-hydroxyphenyl)pyrrolo-[2,1,5-cd]indolizine as a yellow oil in 26% yield. HPLC (eluent: MeOH isocratic 90%, buffer DEA): Rt=3.19 min (94% purity). $^1$H-NMR (acetone-d$_6$, 200 MHz); δ: 1.43 (t, 3H); 1.80 (s, 3H); 2.08 (t, 1H+acetone); 2.28 (s, 3H); 2.48 (t, 1H); 2.67 (s, 2H); 2.98 (s, 1H); 3.08 (t, 1H); 3.23 (m, 2H); 3.53 (t, 1H); 7.01 (d, 2H); 7.29 (s, 1H); 7.48–7.59 (m, 3H); 7.77 (dd, 1 H); 8.06 (d, 1H); 8.12 (d, 1H).

EXAMPLE 68

3-Dimethylaminomethyl-1-ethyl-2-(4-hydroxyphenyl)pyrrolo[2,1,5-cd]indolizine

Step 1:

3-(4-Benzyloxyphenyl)-2-dimethylcarbamoyl-4-ethylpyrrolo[2,1,5-cd]indolizine-1-carboxylic acid 3-(4-benzyloxyphenyl)-4-ethylpyrrolo[2,1,5-cd] indolizine-1,2-dicarboxylic acid anhydride (prepared in analogy with the synthetic principles outlined in example 23, step 1–8) was aminolyzed by the general synthetic principles outlined in example 62, step 9, to afford 3-(4-benzyloxyphenyl)-2-dimethylcarbamoyl-4-ethylpyrrolo[2,1,5-cd]indolizine-1-carboxylic acid as a yellow solid in 73% yield. M.p. 236–238° C. MS(SP): m/z 466 (M+). $^1$H-NMR (CDCl$_3$, 200 MHz) δ: 1.46 (t, 3H); 2.53 (x, 3H); 2.91 (s, 3H); 3.17 (m, 2H); 5.18 (s, 2H); 7.12 (d, 2H); 7.30–7.58 (m, 7H); 7.85–8.00 (m, 2H); 8.55 (d, 1H).

Step 2:

3-(4-Benzyloxyphenyl)-4-ethylpyrrolo[2,1,5-cd] indolizine-2-carboxylic acid dimethylamide 3-(4-Benzyloxyphenyl)-2-dimethylcarbamoyl-4-ethylpyrrolo[2,1,5-cd]indolizine-1-carboxylic acid was decarboxylated by the general synthetic principles outlined in example 23, step 10 to afford 3-(4-benzyloxyphenyl)-4-ethylpyrrolo[2,1,5-cd]indolizine-2-carboxylic acid dimethylamide as a yellow solid in 85% yield. M.p. 92–95° C. MS(SP): m/z 422 (M+). $^1$H-NMR (CDCl$_3$, 200 MHz) δ: 1.47 (t, 3H); 2.43 (s, 3H); 2.86 (s, 3H); 3.22 (q, 2H); 5.17 (s, 2H); 7.11 (d, 2H); 7.30–7.60 (m, 8H); 7.68 (dd, 1H); 7.95 (d, 2H).

Step 3:

4-Ethyl-3-(4-benzyloxyphenyl)pyrrolo[2,1,5-cd] indolizine-2-carboxylic acid dimethylamide 4-Ethyl-3-(4-benzyloxyphenyl)pyrrolo[2,1,5-cd] indolizine-2-carboxylic acid dimethlamide was hydrogenated by the general synthetic principles outlined in example 12, to afford 4-ethyl-3-(4-hydroxyphenyl)pyrrolo[2,1,5-cd] indolizine-2-carboxylic acid dimethylamide as a yellow gum in 113% yield (ethanol incl.). $^1$H-NMR (CDCl$_3$, 300 MHz) δ: 1.43 (t, 3H); 2.56 (s, 3H); 2.98 (s, 3H); 3.19 (q, 2H); 7.00 (d, 2H); 7.33 (s, 1H); 7.49 (d, 2H); 7.68 (dd, 1H); 7.96 (d, 2H).

Step 4:

3-Dimethylaminomethyl-1-ethyl-2-(4-hydroxyphenyl)pyrrolo[2,1,5-cd]indolizine

4-Ethyl-3-(4-hydroxyphenyl)pyrrolo[2,1,5-cd]indolizine-2-carboxylic acid dimethylamide (0.14 g, 0.37 mmol) was dissolved in 25 ml of dry tetrahydofurane under a nitrogen atmosphere. Lithium aluminium hydride (20 mg, 0.53 mmol) was added in portions and stirring was continued for ½ hours. The reaction mixture was quenched with 0.02 ml of water, 0.04 ml of a 2 M sodium hydroxide solution and then 0.04 ml of water again. The resulting precipitate was filtered off and washed with ethyl acetate. The solvent was removed and the crude product was purified by column chromatography over silica gel 60, using 10% of methanol in dichloromethane as the eluent. Fractions containing the product were collected and the solvent was evaporated to afford 63 mg (53%) of the title compound as a yellow solid. M.p. 176–178° C. MS(SP): m/z 318 (M+). $^1$H-NMR (DMSO-d$_6$, 300 MHz) δ: 1.35 (t, 3H); 2.27 (s, 6H); 3.10 (q, 2H); 3.94 (s, 2H); 6.98 (d, 2H); 7.25 (s, 1H); 7.57 (d, 2H); 7.72 (dd, 1H); 8.02 (d, 1H); 8.09 (d, 1H); 9.70 (s, 1H).

EXAMPLE 69

2-(4-Benzyloxyphenyl)-3-dimethylaminomethyl-1-ethylpyrrolo[2,1,5-cd]indolizine 3-(4-benzyloxyphenyl)-4-ethylpyrrolo[2,1,5-cd] indolizine-2-carboxylic acid dimethylamide, prepared in example 68, step 2, was reduced by the general synthetic principles outlined in example 68, step 4, to afford 2-(4-benzyloxyphenyl)-3-dimethylaminomethyl-1-ethylpyrrolo [2,1,5-cd]indolizine as a yellow gum in 90% yield. MS(SP): m/z 408 (M+). $^1$H-NMR (CDCl$_3$, 200 MHz) δ: 1.41 (t, 3H); 2.22 (s, 6H); 3.13 (q, 2H); 3.78 (s, 2H); 5.16 (s, 2H); 7.10–7.18 (m, 3H); 7.30–7.71 (m, 8H); 7.83 (d, 1H); 7.88 (d, 1H).

EXAMPLE 70

3-(4-Benzyloxyphenyl)-4-ethylpyrrolo[2,1,5-cd] indolizine-2-carboxylic acid dimethylamide (0.42 g, 0.99 mmol), prepared in example 68, step 2, was dissolved in 10 ml of dry tetrahydofurane under a nitrogen atmosphere. This solution was cooled down to −78° C. whereas 1.8 M phenyllithium in cyclohexane/diethyl ether (0.8 ml, 1.44 mmol) was added. The reaction mixture was stirred for 2 hours, warming to room temperature. The mixture was poured into 50 ml of saturated aqueous ammonium chloride and the organic material was extracted into 4×50 ml of dichloromethane. The combined organic layers were washed with brine, dried over magnesium sulfate, and evaporated to an orange gum. The crude product was purified by column chromatography over silica gel 60, using 10% of diethyl ether in petroleum ether as the eluent. Fractions containing the product were collected and the solvent was evaporated to afford 376 mg (82%) of 3-benzoyl-2-(4-benzyloxyphenyl)-1-ethylpyrrolo[2,1,5-cd] indolizine as a yellow solid. MS(SP): m/z 455 (M+). $^1$H-NMR (CDCl$_3$, 200 MHz) δ: 1.42 (t, 3H); 3.13 (q, 2H); 5.05 (s, 2H); 6.90 (d, 2H); 7.18–7.52 (m, 10H); 7.58 (s, 1H); 7.73 (dd, 1H); 7.89 (d, 2H); 8.05 (m, 2H).

EXAMPLE 71

3-Benzyl-1-ethyl-2-(4-hydroxyphenyl)pyrrolo[2,1,5-cd]indolizine

3-Benzoyl-2-(4-benzyloxyphenyl)-1-ethylpyrrolo[2,1,5-cd]indolizine was hydrogenated by the general synthetic principles outlined in example 12, to afford 3-benzyl-1-ethyl-2(4-hydroxyphenyl)pyrrolo[2,1,5-cd]indolizine as an orange solid in 59% yield. $^1$H-NMR (CDCl$_3$, 300 MHz) δ: 1.39 (t, 3H); 3.10 (q, 2H); 4.30 (s, 2H); 6.89–6.95 (m, 3H); 7.08–7.30 (m, 5H); 7.42 (d, 2H); 7.60 (dd, 1H); 7.78 (d, 1H); 7.86 (d, 1H).

EXAMPLE 72

2-(4-Acetoxyphenyl)-3-benzyl-1-ethylpyrrolo[2,1,5-cd]indolizine

3-Benzyl-1-ethyl-2-(4-hydroxyphenyl)pyrrolo[2,1,5-cd]indolizine (143 mg, 0.66 mmol) was dissolved in 10 ml of dry tetrahydrofuran and -.10 ml of dry pyridine and acetic anhydride (0.6 ml, 5.43 mmol) was added. The mixture was stirred at room temperature for 24 hours. The reaction mixture was poured into 100 ml of saturated sodium hydrogen carbonate and stirred for 20 minutes. The organic material was extracted into dichloromethane (4×50 ml), and the combined organic layers were washed with brine, dried over magnesium sulfate and the solvent was evaporated. The crude product was purified by column chromatography over silica gel 60, using 5% of diethyl ether in petroleum ether as the eluent to afford 91 mg (35%) of 2-(4-acetoxyphenyl)-3-benzyl-1-ethylpyrrolo[2,1,5-cd]indolizine as a solid. MS(SP): m/z 393 (M+). $^1$H-NMR (CDCl$_3$, 300 MHz) δ: 1.39 (t, 3H); 2.37 (s, 3H); 3.10 (q, 2H); 4.29 (s, 2H); 6.94 (s, 1H); 7.05–7.25 (m, 7H); 7.52 (d, 2H); 7.61 (dd, 1H); 7.80 (d, 1H), 7.89 (d, 1H).

EXAMPLE 73

1-Ethyl-5-hydroxy-2-(4-hydroxyphenyl)-4-(1-oxopropyl)pyrrolo[2,1,5-cd]indolizine Step 1:

4-Acetyl-5-benzyloxy-2-(4-benzyloxyphenyl)-1-ethylpyrrolo[2,1,5-cd]indolizine 6-Benzyloxy-2-(4-benzyloxyphenyl)-1-ehtylindolizine, prepared in example 23, step 5, (2.17 g, 5.0 mmol) was dissolved in 100 ml of dry toluene under a nitrogen atmosphere, and the mixture was stirred in an ice bath, while 3-butyn-2-one (0.34 ml, 5.75 mmol) was added dropwise. The cooling source was removed and stirring was continued for twenty hours. 2,3-Dichloro-5,6-dicyano-1,4-benzoquinone (0.57 g, 0.25 mmol) was added in portions and stirring was continued for 1½ hour. The solvent was evaporated and the crude product was purified by column chromatography over silica gel 60, using 20% of ethyl acetate in petroleum ether as the eluent. Fractions containing the product were colleted and the solvent was evaporated. The crude product was and crystallized from diethyl ether to afford 0.955 g (38%) of 4-acetyl-5-benzyloxy-2-(4-benzyloxyphenyl)-1-ethylpyrrolo[2,1,5-cd]indolizine as crystals. MS(SP): m/z 499 (M+). $^1$H-NMR (CDCl$_3$, 400 MHz) δ: 1.44 (t, 3H); 2.79 (s, 3H); 3.15 (q, 2H); 5.15 (s, 2H); 5.44 (s, 2H); 7.15 (d, 2H); 7.32–7.46 (m, 7H); 7.50 (d, 2H); 7.60 (d, 2H); 7.67–7.74 (m, 3H); 7.94 (s, 1H).

Step 2

5-Benzyloxy-2-(4-benzyloxyphenyl)-1-ethyl-4-(1-oxo-3-piperidinopropyl)pyrrolo[2,1,5-cd]indolizine Dipiperidinomethane (0.3 ml, 1.5 mmol) was dissolved in 20 ml of dimethoxyethane and acetyl chloride (0.11 ml, 1.5 mmol) was added. The mixture was stirred for 30 minutes, while 4-acetyl-5-benzyloxy-2-(4benzyloxyphenyl)-1-ethylpyrrolo[2,1,5-cd]indolizine (0.5 g, 1.0 mmol) was added and HCl-gas was bubbled through the mixture for 15 minutes. The reaction mixture was refluxed for 5 hours and stirred at room temperature for 16 hours. The solvent was evaporated, and the crude HCl-salt was purified by column chromatography over silica gel 60, using 5% of methanol in dichloromethane as the eluent. Fractions containing the HCl-salt were combined and the solvent was evaporated. The salt was dissolved in 20 ml of dry dichloromethane and 2.13 g sodium sulfate and 2.76 g potassium carbonate was added. The mixture was stirred at room temperature for 24 hours. Remaining salts were filtered off, and the solvent was evaporated. The crude product was purified by column chromatography over silica gel 60, using 5% methanol in dichloromethane as the eluent to afford 170 mg (28%) of 5-benzyloxy-2-(4-benzyloxyphenyl)-1-ethyl-4-(1-oxo-3-piperidinopropyl)pyrrolo[2,1,5-cd]indolizine as an oil. $^1$H—NMR (CDCl$_3$, 200 MHz) δ: 1.35–1.75 (m, 9 H); 2.34–3.75 (m, 10 H); 5.17 (s, 4 H); 7.10–7.78 (m, 17 H).

Step 3

1-Ethyl-5-hydroxy-2-(4-hydroxyphenyl)-4-(1-oxopropyl)pyrrolo[2,1,5-cd]indolizine 5-Benzyloxy-2-(4-benzyloxyphenyl)-1-ethyl-4-(1-oxo-3-piperidinopropyl)pyrrolo[2,1,5-cd]indolizine was hydrogenated by the general synthetic principles outlined in example 47, to afford the title compound as crystals in 43% yield. MS(FAB): m/z 334 (M+1). MS(SP): m/z 333 (M+). $^1$H—NMR (DMSO-d$_6$, 400 MHz) δ: 1.23 (t,3 H); 1.38 (t, 3 H); 3.12 (q, 2 H); 3.22 (q, 2 H); 6.99 (d, 2 H); 7.37 (d, 1 H); 7.63 (d, 2 H); 8.03 (d, 1 H); 8.17 (s, 1 H); 9.74 (s, 1 H); 11.90 (s, 1 H). Analysis: Calculated for C$_{21}$H$_{19}$N$_1$O$_3$+14.21 mol % dichloromethane: C, 66.92; H, 5.27; N, 3.60%; Found: C, 66.97; H, 5.24; N, 3.49%.

EXAMPLE 74

5-Acetoxy-2-(4-acetoxyphenyl)-1-ethyl-4-(1-oxopropyl)pyrrolo[2,1,5-cd]indolizine 1-Ethyl-5-hydroxy-2-(4-hydroxyphenyl)-4-(1-oxopropyl)pyrrolo[2,1,5-cd]indolizine was acetylated by the general synthetic principles outlined in example 72, to afford 5-acetoxy-2-(4-acetoxyphenyl)-1-ethyl-4-(1-oxopropyl)pyrrolo[2,1,5-cd]indolizine in 52% yield. $^1$H—NMR (DMSO-d$_6$, 400 MHz) δ: 1.24 (t,3 H); 1.38 (t, 3 H); 2.33 (s, 3 H); 2.53 (s, 3 H); 3.01–3.21 (m, 4 H); 7.22–8.05 (m, 7 H).

EXAMPLE 75

4-Benzoyl-1-ethyl-2-(4-methoxyphenyl)pyrrolo[2,1,5-cd]indolizine

Step 1

1-Ethyl-2-(4-methoxyphenyl)pyrrolo[2,1,5-cd]indolizine

4-Ethyl-2-(4-methoxyphenyl)pyrrolo[2,1,5-cd]indolizine-1,2-dicarboxylic acid, prepared by the general synthetic pathway outlined in example 23, step 7, using proper starting materials, was decarboxylated by the general synthetic principles outlined in example 23, step 10, to afford 1-ethyl-2-(4-methoxyphenyl)pyrrolo[2,1,5-cd]indolizine as an oil in 84% yield. $^1$H—NMR (DMSO-d$_6$, 400 MHz) δ: 1.42 (s, 3 H); 3.24 (q, 2 H); 3.86 (s, 3 H); 7.18 (d, 2 H); 7.32 (d, 1 H); 7.71 (d, 1 H); 7.74 (t, 1 H); 7.78 (d, 2 H); 8.08 (d, 1 H); 8.13 (d, 1 H).

Step 2

4-Bromo-1-ethyl-2-(4-methoxyphenyl)pyrrolo[2,1,5-cd]indolizine

1-Ethyl-2-(4-methoxyphenyl)pyrrolo[2,1,5-cd]indolizine was brominated by the general synthetic principles outlined in example 75, step 2, to afford 4-bromo-1-ethyl-2-(4-methoxyphenyl)pyrrolo[2,1,5-cd]indolizine as green crystals in 78% yield. $^1$H—NMR (CDCl$_3$, 300 MHz) δ: 1.45 (t, 3 H); 3.23 (q, 2 H); 3.90 (s, 3 H); 7.08 (d, 2 H); 7.58 (s, 1 H); 7.63–7.72 (m, 3 H); 7.90 (d, 1 H); 7.92 (d, 1 H).

Step 3

4-Benzoyl-1-ethyl-2-(4-methoxyphenyl)pyrrolo[2,1,5-cd]indolizine

4-Bromo-1-ethyl-2-(4-methoxyphenyl)pyrrolo[2,1,5-cd]indolizine (0.345 g, 1.0 mmol), was dissolved in 10 ml of dry tetrahydrofuran under a nitrogen atmosphere, and the solution was cooled to −78° C., while 1.35 M t-butyllithium in pentane (1.5 ml, 2.03 mmol) was added slowly. The orange solution was stirred for 30 minutes at −78° C. N,N-dimethylbenzamide (0.19 g, 1.27 mmol) dissolved in 5 ml of tetrahydrofuran was added and the reaction was stirred for 20 minutes. The reaction mixture was heated to room temperature, and stirred for 2 days. The mixture was poured into 50 ml of a saturated ammonium chloride solution and the organic material was extracted into dichloromethane (4×50 ml). The combined organic layers was washed with brine, dried overmagnesium sulfate, and evaporated to a yellow gum. The crude product was purified by column chromatography over silica gel 60, using 20% of diethyl ether in hexane as the eluent to afford 0.15 g (40%) of 4-benzoyl-1-ethyl-2-(4-methoxyphenyl)pyrrolo[2,1,5-cd]indolizine as a yellow solid. MS(SP): m/z 379 (M+). $^1$H—NMR (CDCl$_3$, 200 MHz) δ: 1.47 (t, 3 H); 3.21 (q, 2 H); 3.89 (s, 3 H); 7.08 (d, 2 H); 7.46–7.60 (m,3 H); 7.69 (d, 2 H); 7.81–7.98 (m, 5 H); 8.39 (dd, 1 H).

EXAMPLE 76

4-(4-Benzyloxybenzoyl)-1-ethyl-2-(4-methoxyphenyl)pyrrolo[2,1,5-cd]indolizine 4-Bromo-1-ethyl-2-(4-methoxyphenyl)pyrrolo[2,1,5-cd]indolizine, prepared in example 75, step 2, was reacted with t-butyllithium and N,N-dimethyl 4-benzyloxybenzamide by the general synthetic principles outlined in example 75, to afford 4-(4-benzyloxybenzoyl)-1-ethyl-2-(4-methoxyphenyl)pyrrolo[2,1,5-cd]indolizine in 14% yield. MS(SP): m/z 485 (M+). $^1$H—NMR (CDCl$_3$, 200 MHz) δ: 1.48 (t, 3 H); 3.21 (q, 2 H); 3.90 (s, 3 H); 5.17 (s, 2 H); 7.03–7.12 (m,4 H); 7.30–7.50 (m, 5 H); 7.70 (d, 2 H); 7.80–8.01 (m, 5 H); 8.39 (dd, 1 H).

EXAMPLE 77

1-Ethyl-2-(4-methoxyphenyl)-4-(4-(2-piperidinoethoxy)phenyl)pyrrolo[2,1,5-cd]indolizine Step 1

4-(4-Benzyloxyphenyl)-1-ethyl-2-(4-methoxyphenyl)pyrrolo[2,1,5-cd]indolizine 4-Bromo-1-ethyl-2-(4-methoxyphenyl)pyrrolo[2,1,5-cd]indolizine (0.354 g, 1.0 mmol), prepared in example 75, step 2, was dissolved in 15 ml of 1,2-dimethoxyethane under a nitrogen atmosphere. tetrakistriphenylphospine palladium (0) (0.06 g, 0.052 mmol) was added, and the mixture was stirred for 10 minutes. Sodium carbonate (0.65 g, 6.13 mmol) and water 2 ml was added and stirring was continued for 10 minutes. 4-Benzyloxyphenyl boronic acid (0.91 g, 3.99 mmol) dissolved in 10 ml of hot 1,2-dimethoxyethane was added and the mixture was heated to 85–90° C. for 18 hours. The suspension was poured into 100 ml of water and the organic material was extracted into dichloromethane (1×100 ml and 3×50 ml). The combined organic layers were washed with brine, dried overmagnesium sulfate, and evaporated. The crude product was purified by column chromatography over silica gel 60, using 3% of diethyl ether in hexane as the eluent to afford a yellow solid, which was recrystallised from dichloromethane and petroleum ether, to afford 0.31 g (68%) of 4-(4-benzyloxyphenyl)-1-ethyl-2-(4-methoxyphenyl)pyrrolo[2,1,5-cd]indolizine as yellow crystals. MS(SP): m/z 457 (M+). $^1$H—NMR (CDCl$_3$, 400 MHz) δ: 1.48 (t, 3 H); 3.25 (q, 2 H); 3.91 (s, 3 H); 5.14 (s, 2 H); 7.07–7.13 (m,4 H); 7.31–7.51 (m, 5 H); 7.67 (dd, 1 H); 7.70 (s, 1 H); 7.73–7.82 (m, 4 H); 7.92 (d, 1 H); 8.13 (d, 1 H). Analysis: Calculated for C$_{32}$H$_{27}$N$_1$O$_2$: C, 84.00; H, 5.95; N, 3.06%; Found: C, 84.07; H, 6.02; N, 2.90%.

Step 2

1-Ethyl-4-(4-hydroxyphenyl)-2-(4-methoxyphenyl)pyrrolo[2,1,5-cd]indolizine 4-(4-Benzyloxyphenyl)-1-ethyl-2-(4-methoxyphenyl)pyrrolo[2,1,5-cd]indolizine hydrogenated by the general synthetic principles outlined in example 12, to afford 1-ethyl-4-(4-hydroxyphenyl)-2-(4-methoxyphenyl)pyrrolo[2,1,5-cd]indolizine as a yellow solid in 93% yield. MS(SP): m/z 367 (M+). $^1$H—NMR (DMSO-d$_6$, 400 MHz) δ: 1.41 (t,3 H); 3.23 (q, 2 H); 3.87 (s, 3 H); 6.90 (d, 2 H); 7.17 (d, 2 H); 7.73 (dd, 1 H); 7.78 (d, 2 H); 7.82 (d, 2 H); 7.89 (s, 1 H); 8.13 (d, 1 H); 8.30 (d, 1 H); 9.83 (br s, 1 H).

Step 3

1-Ethyl-2-(4-methoxyphenyl)-4-(4-(2-piperidinoethoxy)phenyl)pyrrolo[2,1,5-cd]indolizine 1-Ethyl-4-(4-hydroxyphenyl)-2-(4-methoxyphenyl)pyrrolo[2,1,5-cd]indolizine (0.368 g, 1.0 mmol), potassium carbonate (2.07 g, 15.9 mmol), sodium iodide (8 mg, 0.05 mmol) and 1-(2-chloroethyl)piperidine hydrochloride was suspended in 70 ml of dry acetone. The mixture was refluxed for 6 hours, and stirred at room temperature for 16 hours. Remaining salts were filtered off, and the solvent was evaporated. The crude product was purified by column chromatography over silica gel 60, using 15% of methanol in dichloromethane as the eluent. Fractions containing the product were combined and the solvent was evaporated. The crude product was crystallised from diethyl ether and petroleum ether to afford 0.326 g (68%) of the title compound. $^1$H—NMR (CDCl$_3$, 200 MHz) δ: 1.40–1.70 (m,9 H); 2.50–2.60 (m, 4 H); 2.82 (t, 2 H); 3.26 (q, 2 H); 3.91 (s, 3 H); 4.19 (t, 2 H); 7.01–7.13 (m, 4 H); 7.62–7.83 (m, 6 H); 7.92 (d, 1 H); 8.14 (d, 1 H).

EXAMPLE 78

1-Ethyl-2-(4-hydroxyphenyl)-4-[4-(2-piperidinoethoxy)phenyl]pyrrolo[2,1,5-cd]indolizine 1-Ethyl-2-(4-methoxyphenyl)-4-[4-(2-piperidinoethoxy)phenyl]pyrrolo[2,1,5-cd]indolizine (190 mg, 0.4 mmol) and pyridinium hydrochloride (462 mg, 4.0 mmol) was melted together at 170° C., and stirring was continued for 24 hours at 170° C. The mixture was cooled to room temperature and dissolved in 10 ml of methanol and 50 ml of dichloromethane. 100 ml of water and solid sodium hydrogen carbonate was added until pH=8. The aqueous layer was extracted with 10% of methanol in dichloromethane (2×50 ml), and the combined organic layers were washed with brine, dried oversodium sulfate and evaporated. The crude product was purified by column chromatography over silica gel 60, using 10% of methanol in dichloromethane as the eluent. The crude product was recrystallized from methanol, dichloromethane and petroleum ether to afford 55 mg (29%)

of 1-ethyl-2-(4-hydroxyphenyl)-4-[4-(2-piperidinoethoxy) phenyl]pyrrolo[2,1,5-cd]indolizine. MS(SP): m/z 464 (M+). $^1$H—NMR (DMSO-d$_6$, 200 MHz) δ: 1.31–1.58 (m,9 H); 2.39–2.49 (m, 4 H); 2.68 (t, 2 H); 3.22 (q, 2 H); 4.12 (t, 2 H); 7.00 (d, 2 H); 7.07 (d, 2 H); 7.66–7.79 (m, 3 H); 7.83–7.98 (m, 3 H); 8.11 (d, 1 H); 8.29 (d, 1 H); 9.83 (br s, 1 H).

EXAMPLE 79

4-Acetyl-1-ethyl-7-benzyloxy-2-(4-benzyloxyphenyl)pyrrolo[2,1,5-cd]indolizine

Step 1

3-Benzyloxy-2-bromopyridine

2-Bromo-3-hydroxypyridine (15 g, 86 mmol) and Triton® B (37.5 g, 40 mmol) was refluxed in 100 ml of ethanol for 5 hours. The solution was evaporated to a fat oil and headed to 150° C. for 3 hours. The mixture was cooled to room temperature and 100 ml of water was added. The organic material was extracted into diethyl ether (3×50 ml), and the combined organic layers were dried over magnesium sulfate, and the solvent was evaporated. The crude product was purified by column chromatography over silica gel 60, using 50% of diethyl ether in petroleum ether as the eluent to afford 7.7 g (34%) of 3-benzyloxy-2-bromopyridine. $^1$H—NMR (CDCl$_3$, 200 MHz) δ: 5.18 (s, 2 H); 7.16 (d, 2 H); 7.28–7.49 (m, 5 H); 7.99 (dd, 1 H).

Step 2

3-Benzyloxy-2-propylpyridine

Solid magnesium (0.7 g, 30 mmol) was stirred in 15 ml of dry diethyl ether under a nitrogen atmosphere. An iodine crystal and 1 drop of 1-bromopropane was added and the mixture was heated to reflux. The heating source was removed and the remaining 1-bromopropane (2.46 g, 20 mmol) was added in portions. The Grignard reagent was stirred for ½ hour at room temperature. 3-Benzyloxy-2-bromopyridine (3.66 g, 13.8 mmol) and a catalytic amount of [1,2-bis(diphenylphosphino)ethane]dichloronickel(II) was dissolved in 200 ml of dry diethyl ether under a nitrogen atmosphere, and the Grignard reagent was added dropwise. The reaction mixture was stirred for 3 hours, and carefully poured into 200 ml of water. The aqueous layer was extracted with 2×100 ml of diethyl ether. The combined organic layers were dried overmagnesium sulfate and the solvent was evaporated. The crude product was purified by column chromatography over silica gel 60, using 50% of diethyl ether in petroleum ether as the eluent to afford 2.25 g (71%) of 3-benzyloxy-2-propylpyridine. $^1$H—NMR (CDCl$_3$, 200 MHz) δ: 0.98 (t,3 H); 1.77 (sextet, 2 H); 1.86 (t, 2 H); 5.07 (s, 2 H); 7.02–7.16 (m, 2 H); 7.27–7.45 (m, 5 H); 8.12 (dd, 1 H).

Step 3

1-Ethyl-8-benzyloxy-2-(4-benzyloxyphenyl) indolizine

3-Benzyloxy-2-propylpyridine was reacted with 4-benzyloxyphenacylbromide and with sodium hydrogen carbonate by the general synthetic principles outlined in example 1, step 2, to afford 1-ethyl-8-benzyloxy-2-(4-benzyloxyphenyl)indolizine as yellow crystals in 66% yield. M.p. 104–105° C. MS(SP): m/z 433 (M+). $^1$H—NMR (DMSO-d$_6$, 200 MHz) δ: 1.10 (t, 3 H); 2.86 (q, 2 H); 5.12 (s, 2 H); 5.19 (s, 2 H); 6.13 (d, 1 H); 6.38 (t, 1 H); 7.06 (d, 2 H); 7.28–7.54 (m, 13 H); 7.77 (d, 1 H).

Step 4

4-Acetyl-1-ethyl-7-benzyloxy-2-(4-benzyloxyphenyl)pyrrolo[2,1,5-cd]indolizine

1-Ethyl-8-benzyloxy-2-(4-benzyloxyphenyl)indolizine was reacted with 3-butyn-2-one by the general synthetic principles outlined in example 73, step 1, to afford the title compound as yellow crystals in 14% yield. M.p. 147–149° C. MS(SP): m/z 499 (M+). $^1$H—NMR (DMSO-d$_6$, 200 MHz) δ: 1.37 (t, 3 H); 2.65 (s, 3 H); 3.16 (q, 2 H); 5.22 (s, 2 H); 5.53 (s, 2 H); 7.23 (d, 2 H); 7.33–7.83 (m, 13 H); 8.13 (s, 1 H); 8.28 (d, 1 H).

EXAMPLE 80

4-Acetyl-1-ethyl-7-hydroxy-2-(4-hydroxyphenyl) pyrrolo[2,1,5-cd]indolizine

4-Acetyl-1-ethyl-7-benzyloxy-2-(4-benzyloxyphenyl) pyrrolo[2,1,5-cd]indolizine was hydrogenated by the general synthetic principles outlined in example 12, to afford 4-acetyl-1-ethyl-7-hydroxy-2-(4-hydroxyphenyl)pyrrolo[2,1,5-cd]indolizine as green crystals in 66% yield. M.p. 167–173° C. MS(SP): m/z 319 (M+). $^1$H—NMR (DMSO-d$_6$, 200 MHz) δ: 1.40 (t, 3 H); 2.62 (s, 3 H); 3.18 (q, 2 H); 6.98 (d, 2 H); 7.43 (d, 1 H); 7.61 (d, 2 H); 7.98 (s, 1 H); 8.13 (d, 1 H); 9.72 (br s, 1 H); 10.90 (br s, 1 H).

EXAMPLE 81

4-Acetyl-2-(4-benzyloxyphenyl)-1-ethyl-7-hydroxymethylpyrrolo[2,1,5-cd]indolizine Step 1

Ethyl 3-amino-hex-2-enoate

Ethyl 3-oxo-hexanoate (100 g, 0.63 mmol) was dissolved in 400 ml of diethyl ether and ammonia was bobbled through the solution for 8 hours. During the reaction magnesium sulfate was added in portions as a drying agent. When no starting material was detected on TLC, the mixture was filtered, and the solvent was evaporated to afford 75 g (76%) of ethyl 3-amino-hex-2-enoate as an oil. $^1$H—NMR (CDCl$_3$, 200 MHz) δ: 0.95 (t, 3 H); 1.25 (t, 3 H); 1.58 (sextet, 2 H); 2.09 (t, 2 H); 4.11 (q, 2 H); 4.52 (s, 1 H).

Step 2

Ethyl 2-n-propylpyridine-3-carboxylate

Acrolein (30 g, 0.52 mmol) was added during a period of 2 hours to a stirred solution of ethyl 3-amino-hex-2-enoate (62 g, 0.4 mmol) dissolved in 2 g of piperidine and 300 ml of anhydrous ethanol. The mixture was refluxed for 3 hours and the ethanol was evaporated. The remaining oil was heated to 100° C. and solid sulfur (52 g, 1.6 mmol) was carefully added in portions. The temperature was elevated to 150° C. for 3 hours. The mixture was cooled to room temperature and 200 ml of diethyl ether and 800 ml of water was added. The organic material was extracted into diethyl ether (2×200 ml). The combined organic layer were dried overmagnesium sulfate, and evaporated to an oil. The crude product was purified by column chromatography over silica gel 60, using diethyl ether as the eluent to afford 50 g (65%) of ethyl 2-n-propylpyridine-3-carboxylate as an oil. $^1$H—NMR (CDCl$_3$, 200 MHz) δ: 1.01 (t, 3 H); 1.40 (t, 3 H); 1.75 (sextet, 2 H); 3.12 (t, 2 H); 4.38 (q, 2 H); 7.19 (dd, 1 H); 8.13 (dd, 1 H); 8.63 (dd, 1 H).

Step 3

3-Hydroxymethyl-2-n-propylpyridin

Ethyl 2-n-propylpyridine-3-carboxylate was reduced with lithium aluminum hydride by the general synthetic principle outlined in example 1, step 4, to afford 3 hydroxymethyl-2-n-propylpyridin as a yellow oil in 90% yield. $^1$H—NMR (CDCl$_3$, 200 MHz) δ: 0.98 (t, 3 H); 1.72 (sextet, 2 H); 2.75 (t, 2 H); 3.35 (br s, 1 H); 4.74 (s, 2 H); 7.12 (dd, 1 H); 7.74 (dd, 1 H); 8.39 (dd, 1 H).

Step 4

1-Ethyl-2-(4-benzyloxyphenyl)-8-hydroxymethylindolizine

3-Hydroxymethyl-2-n-propylpyridin was reacted with 4-benzyloxyphenacylbromide by the general synthetic principles outlined in example 1, step 2, to afford 1-ethyl-2-(4-benzyloxyphenyl)-8-hydroxymethylindolizine as yellow crystals in 83% yield. M.p. 144–145° C. MS(SP): m/z 357 (M+). $^1$H—NMR (DMSO-d$_6$, 200 MHz) δ: 1.08 (t, 3 H); 2.83 (q, 2 H); 4.73 (d, 2 H); 5.12 (s, 2 H); 5.22 (t, 1 H); 6.43 (dd, 1 H); 6.66 (d, 1 H); 7.07 (d, 2 H); 7.28–7.53 (m, 8 H); 8.04 (d, 1 H).

Step 5

2-(4-Benzyloxyphenyl)-8-(tert-butyldimethylsilanyloxymethyl)-1-ethylindolizine

1-Ethyl-2-(4-benzyloxyphenyl)-8-hydroxymethylindolizine (21.3 g, 60 mmol), triethylamine (7.88 g, 78 mmol) and tert-butyldimethylsilylchloride (17.8 g, 118 mmol) was dissolved in 200 ml of dry dichloromethane, and the mixture was stirred for 2 days. The solvent was evaporated and the crude product was purified by column chromatography over silica gel 60, using diethyl ether as the eluent. Fractions containing the product were combined and the solvent was evaporated. The product was crystallised from diethyl ether and petroleum ether to afford 25.5 g (90%) of 2-(4-benzyloxyphenyl)-8-(tert-butyldimethylsilanyloxymethyl)-1-ethylindolizine as yellow crystals. M.p. 79–81° C. $^1$H—NMR (CDCl$_3$, 200 MHz) δ: 0.01 (s, 6 H); 0.83 (s, 9 H); 1.02 (t, 3 H); 2.74 (q, 2 H); 4.92 (s, 2 H); 4.96 (s, 2 H); 6.25 (dd, 1 H); 6.61 (d, 1 H); 6.89 (d, 2 H); 7.11 (s, 1 H); 7.17–7.37 (m, 7 H); 7.59 (d, 1 H).

Step 6

4-Acetyl-2-(4-benzyloxyphenyl)-7-(tert-butyldimethylsilanyloxymethyl)-1-ethylpyrrolo[2,1,5-cd]indolizine 2-(4-Benzyloxyphenyl)-8-(tert-butyldimethylsilanyloxymethyl)-1-ethylindolizine was reacted with 3-butyn-2-one by the general synthetic principles outlined in example 73, step 1, to afford 4-acetyl-2-(4-benzyloxyphenyl)-7-(tert-butyldimethylsilanyloxymethyl)-1-ethylpyrrolo[2,1,5-cd] indolizine as a brown oil in 70% yield. $^1$H—NMR (DMSO-d$_6$, 200 MHz) δ: 0.13 (s, 6 H); 0.89 (s, 9 H); 1.37 (t, 3 H); 2.64 (s, 3 H); 3.18 (q, 2 H); 5.20 (s, 2 H); 5.32 (s, 2 H); 7.12–7.54 (m, 7 H); 7.73 (d, 2 H); 7.94 (d, 2 H); 8.18 (s, 1 H); 8.34 (d, 1 H).

Step 7

4-Acetyl-2-(4-benzyloxyphenyl)-1-ethyl-7-hydroxymethylpyrrolo[2,1,5-cd]indolizine 4-Acetyl-2-(4-benzyloxyphenyl)-7-(tert-butyldimethylsilanyloxymethyl)-1-ethylpyrrolo[2,1,5-cd] indolizine (1.5 g, 2.79 mmol) and tetrabutylammoniumfluoride hydrate (2.92 g. 11.16 mmol) was dissolved in 20 ml of dry tetrahydrofuran and stirred for 24 hours. Diethyl ether (100 ml) was added and the organic layer was extracted with 100 ml of 15% acetic acid, 100 ml of saturated sodium hydrogen carbonate, 100 ml of water, washed with brine, dried over sodium sulfate, and evaporated to a red-brown solid. The crude product was purified by column chromatography over silica gel 60, using 10% of ethyl acetate in toluene as the eluent. Fractions containing the product were combined an the solvent was evaporated. The remaining solid was crystallised from toluene and petroleum ether to afford 0.7 g (59%) of the title compound. M.p. 190–191° C. MS(SP): m/z 423 (M+). $^1$H—NMR (DMSO-d$_6$, 200 MHz) δ: 1.39 (t, 3 H); 2.64 (s, 3 H); 3.20 (q, 2 H); 5.18 (s, 2 H); 5.22 (s, 2 H); 7.25 (d, 2 H); 7.31–7.55 (m, 5 H); 7.75 (d, 2 H); 8.01 (d, 1 H); 8.20 (s, 1 H); 8.36 (d, 1 H). Analysis: Calculated for C$_{28}$H$_{25}$N$_1$O$_3$: C, 79.41; H, 5.95; N, 3.31%; Found: C, 79.2; H, 5.7; N, 3.2%.

EXAMPLE 82

4-Acetyl-1-ethyl-7-hydroxymethyl-2-(4-hydroxyphenyl)pyrrolo[2,1,5-cd]indolizine

4-Acetyl-2-(4-benzyloxyphenyl)-1-ethyl-7-hydroxymethylpyrrolo[2,1,5-cd]indolizine was hydrogenated by the general synthetic principles outlined in example 12, to afford 4-acetyl-1-ethyl-7-hydroxymethyl-2-(4-hydroxyphenyl)pyrrolo[2,1,5-cd]indolizine as yellow crystals in 89% yield. M.p. 194–195° C. MS(SP): m/z 333 (M+). $^1$H—NMR (DMSO-d$_6$, 200 MHz) δ: 1.39 (t, 3 H); 2.66 (s, 3 H); 3.20 (q, 2 H); 5.18 (s, 2 H); 7.01 (d, 2 H); 7.65 (d, 2 H); 8.00 (d, 1 H); 8.19 (s, 1 H); 8.35 (d, 1 H). Analysis: Calculated for C$_{21}$H$_{19}$N$_1$O$_3$: C, 75.65; H, 5.74; N, 4.20%; Found: C, 75.29; H, 5.83; N, 4.01%.

EXAMPLE 83

3-(4-Benzyloxyphenyl)-4-ethyl-5-hydroxymethylpyrrolo[2,1,5-cd]indolizine-1,2-dicarboxylic acid 2-(4-Benzyloxyphenyl)-8-(tert-butyldimethylsilanyloxymethyl)-1-ethylindolizine, prepared in example 81, step 5, was reacted with dimethyl acetylene dicarboxylate by the general synthetic principle outlined in example 23, step 6, to afford dimethyl 3-(4-benzyloxyphenyl)-5-(tert-butyldimethylsilanyloxymethyl)-4-ethylpyrrolo[2,1,5-cd]indolizine-1,2-dicarboxylate, which was hydrolysed and desilylated by the general synthetic principle outlined in example 23, step 7, to afford 3-(4-benzyloxyphenyl)-4-ethyl-5-hydroxymethylpyrrolo[2,1,5-cd]indolizine-1,2-dicarboxylic acid as yellow crystals in 70% yield. $^1$H—NMR (DMSO-d$_6$, 200 MHz) δ: 1.32 (t, 3 H); 3.09 (q, 2 H); 5.18 (s, 2 H); 5.19 (s, 2 H); 7.19 (d, 2 H); 7.31–7.58 (m, 7 H); 8.08 (d, 1 H); 8.40 (d, 1 H).

EXAMPLE 84

2-(4-Benzyloxyphenyl)-1-ethyl-7-hydroxymethylpyrrolo[2,1,5-cd]indolizine 3-(4-Benzyloxyphenyl)-4-ethyl-5-hydroxymethylpyrrolo[2,1,5-cd]indolizine-1,2-dicarboxylic acid was decarboxylated by the general synthetic principles outlined in example 23, step 10, to afford 2-(4-benzyloxyphenyl)-1-ethyl-7-hydroxymethylpyrrolo[2,1,5-cd]indolizine as yellow crystals in 42% yield. M.p. 99–102° C. $^1$H—NMR (CDCl$_3$, 200 MHz) δ: 1.43 (t, 3 H); 1.28 (q, 2 H); 5.13 (s, 2 H); 5.33 (s, 2 H); 7.14 (d, 2 H); 7.21 (d, 1 H); 7.29–7.52 (m, 5 H); 7.55 (d, 1 H); 7.63–7.73 (m, 3 H); 7.87 (d, 1 H).

EXAMPLE 85

1-Ethyl-7-hydroxymethyl-2-(4-hydroxyphenyl)pyrrolo[2,1,5-cd]indolizine 2-(4-benzyloxyphenyl)-1-ethyl-7-hydroxymethylpyrrolo[2,1,5-cd]indolizine was hydrogenated by the general synthetic principles outlined in example 12, to afford 1-ethyl-7-hydroxymethyl-2-(4-hydroxyphenyl)pyrrolo[2,1,5-cd]indolizine as yellow crystals in 17% yield. M.p. 154–156° C. MS(SP): m/z 291 (M+). $^1$H—NMR (DMSO-d$_6$, 300 MHz) δ: 1.39 (t, 3 H); 3.22 (q, 2 H); 5.20 (s, 2 H); 6.99 (d, 2 H); 7.25 (d, 1 H); 7.58–7.63 (m, 3 H); 7.76 (d, 1 H); 8.01 (d, 1 H); 9.69 (br s, 1 H).

EXAMPLE 86

3-(4-Benzyloxyphenyl)-4-ethyl-5-hydroxymethylpyrrolo[2,1,5-cd]indolizine-1-carboxylic acid 2-(4-Benzyloxyphenyl)-8-(tert-butyldimethylsilanyloxymethyl)-1-ethylindolizine, prepared in example 81, step 5, was reacted with methylpropiolate by the general synthetic principles outlined in example 1, step 3, to afford methyl 3-(4-benzyloxyphenyl)-5-tert-butyldimethylsilanyloxymethyl-4-ethylpyrrolo[2,1,5-cd]indolizine-1-carboxylate, which was hydrolysed and desilylated by the general synthetic principle outlined in example 23, step 7, to afford 3-(4-benzyloxyphenyl)-4-ethyl-5-hydroxymethylpyrrolo[2,1,5-cd]indolizine-1-carboxylic acid as yellow crystals in 37% yield. $^1$H—NMR (DMSO-d$_6$, 200 MHz) δ: 1.40 (t, 3 H); 3.21 (q, 2 H); 5.19 (s, 2 H); 5.20 (s, 2 H); 5.72 (br s, 1 H); 7.24 (d, 2 H); 7.32–7.56 (m, 5 H); 7.75 (d, 2 H); 8.00 (s, 1 H); 8.02 (d, 1 H); 8.30 (d, 1 H).

EXAMPLE 87

2-(4-Benzyloxyphenyl)-1-ethyl-7-((2-pyrrolidinoethoxy)methyl)pyrrolo[2,1,5-cd]indolizine 2-(4-Benzyloxyphenyl)-1-ethyl-7-hydroxymethylpyrrolo[2,1,5-cd]indolizine (0.5 g, 1.3 mmol) was dissolved in 20 ml of dry dimethylsulfoxide under a nitrogen atmosphere. Sodium hydride (100%) (136 mg, 5.7 mmol) was added in portions and stirring was continued for ten minutes. 1-(2-Chloroethyl)pyrrolidine hydrochloride (0.33 g, 1.94 mmol) was added, and the solution was stirred for 4 hours. Ethanol (2 ml) was added dropwise, and the reaction mixture was diluted with 50 ml of water, 50 ml of diethyl ether and 50 ml of brine. The organic material was extracted into diethyl ether (2×50 ml), and the combined organic layers were washed with 3×50 ml of water, 25 ml of brine, dried overmagnesium sulfate, treated with decolourising charcoal and filtered through celite. The solvent was evaporated and the crude product was purified by column chromatography over silica gel 60, using 10% of methanol in dichloromethane as the eluent to afford 0.63 g (100%) of 2-(4-benzyloxyphenyl)-1-ethyl-7-((2-pyrrolidinoethoxy)methyl)pyrrolo[2,1,5-cd]indolizine as a yellow oil. $^1$H—NMR (CDCl$_3$, 200 MHz) δ: 1.44 (t, 3 H); 1.82 (m, 4 H); 2.70 (m, 4 H); 2.85 (t, 2 H); 3.29 (q, 2 H); 3.82 (t, 2 H); 5.19 (s, 2 H); 5.24 (s, 2 H); 7.11–7.24 (m, 3 H); 7.31–7.60 (m, 6 H); 7.65–7.79 (m, 3 H); 7.89 (d, 1 H).

EXAMPLE 88

2-(4-Benzyloxyphenyl)-1-ethyl-7-((2-piperidinoethoxy)methyl)pyrrolo[2,1,5-cd]indolizine 2-(4-Benzyloxyphenyl)-1-ethyl-7-hydroxymethylpyrrolo[2,1,5-cd]indolizine was alkylated, using a proper alkylating agent, by the general synthetic principle outlined in example 87, to afford 2-(4-benzyloxyphenyl)-1-ethyl-7-((2-piperidinoethoxy)methyl)pyrrolo[2,1,5-cd]indolizine as a yellow oil in 85% yield. $^1$H-NMR (CDCl$_3$, 200 MHz) δ: 1.29–1.52 (m, 5H); 1.62 (m, 4H); 2.53 (m, 4H); 2.71 (t, 2H); 3.28 (q, 2H); 3.81 (t, 2H); 5.18 (s, 2H); 5.22 (s, 2H); 7.11–7.24 (m, 3H); 7.30–7.60 (m, 6H); 7.63–7.78 (m, 3H); 7.89 (d, 1H).

EXAMPLE 89

2-(4-Benzyloxyphenyl)-1-ethyl-7-((3-dimethylaminopropoxy)methyl)pyrrolo[2,1,5-cd]indolizine 2-(4-Benzyloxyphenyl)-1-ethyl-7-hydroxymethylpyrrolo[2,1,5-cd]indolizine was alkylated, using a proper alkylating agent, by the general synthetic principle outlined in example 87, to afford 2-(4-benzyloxyphenyl)-1-ethyl-7-((3-dimethylaminopropoxy)methyl)pyrrolo[2,1,5-cd]indolizine as a yellow oil in 70% yield. $^1$H-NMR (CDCl$_3$, 200 MHz) δ: 1.43 (t, 3H); 1.91 (pentet, 2H); 2.33 (s, 6H); 2.53 (t, 2H); 3.28 (q, 2H); 3.70 (t, 2H); 5.17 (s, 4H); 7.11–7.23 (m, 3H); 7.30–7.57 (m, 6H); 7.62–7.76 (m, 3H); 7.88 (d, 1H).

EXAMPLE 90

2-(4-Benzyloxyphenyl)-1-ethyl-7-((3-piperidinopropoxy)methyl)pyrrolo[2,1,5-cd]indolizine 2-(4-Benzyloxyphenyl)-1-ethyl-7-hydroxymethylpyrrolo[2,1,5-cd]indolizine was alkylated, using a proper alkylating agent, by the general synthetic principle outlined in example 87, to afford 2-(4-benzyloxyphenyl)-1-ethyl-7-((3-piperidinopropoxy)methyl)pyrrolo[2,1,5-cd]indolizine as a yellow oil in 95% yield. $^1$H-NMR (CDCl$_3$, 200 MHz) δ: 1.38–1.69 (m, 9H); 1.90 (pentet, 2H); 2.34–2.53 (m, 6H); 3.27 (q, 2H); 3.68 (t, 2H); 5.18 (s, 4H); 7.11–7.23 (m, 3H); 7.30–7.58 (m, 6H); 7.62–7.76 (m, 3H); 7.88 (d, 1H).

EXAMPLE 91

1-Ethyl-2-(4-hydroxyphenyl)-7-((2-pyrrolidinoethoxy)methyl)pyrrolo[2,1,5-cd]indolizine 2-(4-Benzyloxyphenyl)-1-ethyl-7-((2-piperidinoethoxy)methyl)pyrrolo[2,1,5-cd]indolizine was hydrogenated by the general synthetic principles outlined in example 12, to afford 1-ethyl-2-(4-hydroxyphenyl)-7-((2-pyrrolidinoethoxy)methyl)pyrrolo[2,1,5-cd]indolizine as yellow crystals in 91% yield. M.p. 183–187° C. $^1$H-NMR (DMSO-d$_6$, 200 MHz) δ: 139 (t, 3H); 1.68 (m, 4H); 2.54 (m, 4H); 2.74 (t, 2H); 3.22 (q, 2H); 3.71 (t, 2H); 5.16 (s, 2H); 6.99 (d, 2H); 7.29 (d, 1H); 7.55–7.68 (m, 3H); 7.72 (d, 1H); 8.01 (d, 1H); 9.70 (s, 1H).

EXAMPLE 92

1-Ethyl-2-(4-hydroxyphenyl)-7-((2-piperidinoethoxy)methyl)pyrrolo[2,1,5-cd]indolizine 2-(4-Benzyloxyphenyl)-1-ethyl-7-((2-piperidinoethoxy)methyl)pyrrolo[2,1,5-cd]indolizine was hydrogenated by the general synthetic principles outlined in example 12, to afford 1-ethyl-2-(4-hydroxyphenyl)-7-((2-piperidinoethoxy)methyl)pyrrolo[2,1,5-cd]indolizine as yellow crystals in 93% yield. M.p. 68–75° C. $^1$H-NMR (DMSO-d$_6$, 200 MHz) δ: 1.32–1.56 (m, 9H); 2.47–2.90 (m, 6H+DMSO); 3.22 (q, 2H); 3.72 (t, 2H); 5.15 (s, 2H); 7.00 (d, 2H); 7.28 (d, 1H); 7.56–7.68 (m, 3H); 7.72 (d, 1H); 8.02 (d, 1H); 9.71 (s, 1H).

EXAMPLE 93

1-Ethyl-2-(4-hydroxyphenyl)-7-((3-dimethylaminopropoxy)methyl)pyrrolo[2,1,5-cd]indolizine 2-(4-Benzyloxyphenyl)-1-ethyl-7-((3-dimethylaminopropoxy)methyl)pyrrolo[2,1,5-cd]indolizine was hydrogenated by the general synthetic principles outlined in example 12, to afford 1-ethyl-2-(4-hydroxyphenyl)-7-((3-dimethylaminopropoxy)methyl)pyrrolo[2,1,5-cd]indolizine as a yellow oil in 75% yield. ¹H-NMR (DMSO-d₆, 200 MHz) δ: 1.38 (t, 3H); 1.72 (pentet, 2H); 2.15 (s, 6H); 2.35 (t, 2H); 3.22 (q, 2H); 3.60 (t, 2H); 5.10 (s, 2H); 6.99 (d, 2H); 7.28 (d, 1H); 7.58–7.67 (m, 3H); 7.70 (d, 1H); 8.01 (d, 1H); 9.75 (br s, 1H).

EXAMPLE 94

1-Ethyl-2-(4-hydroxyphenyl)-7-((3-piperidinopropoxy)methyl)pyrrolo[2,1,5-cd]indolizine 2-(4-Benzyloxyphenyl)-1-ethyl-7-((3-piperidinopropoxy)methyl)pyrrolo[2,1,5-cd]indolizine was hydrogenated by the general synthetic principles outlined in example 12, to afford 1-ethyl-2-(4-hydroxyphenyl)-7-((3-piperidinopropoxy)methyl)pyrrolo[2,1,5-cd]indolizine as a yellow oil in 90% yield. ¹H-NMR (DMSO-d₆, 200 MHz) δ: 1.27–1.52 (m, 9H); 1.72 (pentet, 2H); 2.22–2.42 (m, 6H); 3.21 (q, 2H); 3.60 (t, 2H); 5.10 (s, 2H); 6.99 (d, 2H); 7.28 (d, 1H); 7.55–7.68 (m, 3H); 7.71 (d, 1H); 8.01 (d, 1H); 9.70 (s, 1H).

EXAMPLE 95

5-Acetoxymethyl-3-(4-benzyloxyphenyl)-2-dimethylcarbamoylpyrrolo[2,1,5-cd]indolizine-1-carboxylic Acid Step 1

5-Acetoxymethyl-3-(4-benzyloxyphenyl)pyrrolo[2,1,5-cd]indolizine-1,2-dicarboxylic Acid Anhydride The general synthetic pathway outlined in example 81, step 5, and example 83 have been applied to proper starting materials in the preparation of 3-(4-benzyloxyphenyl)-5-hydroxymethylpyrrolo[2,1,5-cd]indolizine-1,2-dicarboxylic acid, which was reacted with acetic acid anhydride by the general synthetic principles outlined in example 23, step 8, to afford 5-acetoxymethyl-3-(4-benzyloxyphenyl)pyrrolo[2,1,5-cd]indolizine-1,2-dicarboxylic acid anhydride as red crystals in 86%. ¹H-NMR (DMSO-d₆, 300 MHz) δ: 2.17 (s, 3H); 5.22 (s, 2H); 5.67 (s, 2H); 7.19 (d, 2H); 7.32–7.48 (m, 3H); 7.52 (d, 2H); 8.10–8.19 (m, 2H); 8.27 (d, 2H); 8.34 (d, 1H).

Step 2

5-Acetoxymethyl-3-(4benzyloxyphenyl)-2-dimethylcarbamoylpyrrolo[2,1,5-cd]indolizine-1-carboxylic Acid 5-Acetoxymethyl-3-(4-benzyloxyphenyl)pyrrolo[2,1,5-cd]indolizine-1,2-dicarboxylic acid anhydride was reacted with dimethylamine by the general synthetic principles outlined in example 62, step 9, to afford 5-acetoxymethyl-3-(4-benzyloxyphenyl)-2-dimethylcarbamoylpyrrolo[2,1,5-cd]indolizine-1-carboxylic acid as crystals in 68% yield. ¹H-NMR (DMSO-d₆, 300 MHz) δ: 2.22 (s, 3H); 2.72 (s, 3H); 3.08 (s, 3H); 5.20 (s, 2H); 5.70 (s, 2H); 7.19 (d, 2H); 7.32–7.53 (m, 5H); 7.82 (d, 2H); 7.89 (s, 1H); 8.02 (d, 1H); 8.32 (d, 1H); 12.78 (br s, 1H).

EXAMPLE 96

Dimethyl 3-(4-benzyloxyphenyl)-5-hydroxymethylpyrrolo[2,1,5-cd]indolizine-1,2-dicarboxylate The general synthetic pathway outlined in example 89, step 5, and example 91 have been applied to proper starting material in the preparation of dimethyl 3-(4-benzyloxyphenyl)-5-(tert-butyldimethylsilanyloxymethyl)pyrrolo[2,1,5-cd]indolizine-1,2-dicarboxylate. Dimethyl 3-(4-benzyloxyphenyl)-5-(tert-butyldimethylsilanyloxymethyl)pyrrolo[2,1,5-cd]indolizine-1,2-dicarboxylate (4.5 g, 7.7 mmol) was dissolved in 100 ml of methanol and 4 drops of sulfuric acid. The mixture was refluxed for 2 minutes, and cooled to room temperature. The yellow precipitate was filtered off to afford 3.24 g (89%) of dimethyl 3-(4benzyloxyphenyl)-5-hydroxymethylpyrrolo[2,1,5-cd]indolizine-1,2-dicarboxylate as yellow crystals. ¹H-NMR (CDCl₃, 300 MHz) δ: 3.93 (s, 3H); 3.97 (s, 3H); 5.12 (s, 2H); 5.20 (s, 2H); 7.03 (d, 2H); 7.31–7.50 (m, 6H); 7.62 (m, 2H); 7.72 (m, 1H); 8.07 (m, 1H).

EXAMPLE 97

4-Acetyl-1-ethyl-2-(4-hydroxymethylphenyl)pyrrolo[2,1,5-cd]indolizine

Step 1

1-Ethyl-2-(4-hydroxymethylphenyl)indolizine

The general synthetic pathway outlined in example 1, step 1–2, have been applied to proper starting materials in the preparation of ethyl 4-(1-ethylindolizine-2-yl)benzoate, which was reduced with lithium aluminium hydride by the general synthetic principles outlined in example 1, step 4, to afford 1-ethyl-2-(4-hydroxymethylphenyl)indolizine in 94% yield. ¹H-NMR (CDCl₃, 200 MHz) δ: 1.20 (t, 3H); 2.88 (q, 2H); 4.72 (s, 2H); 6.41 (ddd, 1H); 6.61 (ddd, 1H); 7.29–7.52 (m, 6H); 7.83 (d, 1H).

Step 2

2-(4-(tert-Butyldimethylsilanyloxymethyl)phenyl)-1-ethylindolizine

1Ethyl-2-(4-hydroxymethylphenyl)indolizine was silylated by the general synthetic principles outlined in example 81, step 5, to afford 2-(4-(tert-butyldimethylsilanyloxymethyl)phenyl)-1-ethylindolizine in 87%. ¹H-NMR (CDCl₃, 200 MHz) δ: 0.05 (s, 6H); 0.88 (s, 9H); 1.12 (t, 3H); 2.78 (q, 2H); 4.70 (s, 2H); 6.30 (m, 1H); 6.50 (m, 1H); 7.13–7.42 (m, 6H); 7.74 (d, 1H).

Step 3

4-Acetyl-2-(4-(tert-butyldimethylsilanyloxymethyl)phenyl)-1-ethylpyrrolo[2,1,5-cd]indolizine 2-(4-(tert-Butyldimethylsilanyloxymethyl)phenyl)-1-ethylindolizine was reacted with 3-butyn-2-one by the general synthetic principles outlined in example 73, step 1, to afford 4-acetyl-2-(4-(tert-butyldimethylsilanyloxymethyl)phenyl)-1-ethylpyrrolo[2,1,5-cd]indolizine in 45% yield. ¹H-NMR (CDCl₃, 200 MHz) δ: 0.17 (s, 6H); 0.99 (s, 9H); 1.47 (t, 3H); 2.72 (s, 3H); 3.22 (q, 2H); 4.86 (s, 2H); 7.51 (d, 2H); 7.74 (d, 2H); 7.80–7.96 (m, 3H); 8.48 (dd, 1H).

Step 4

4-Acetyl-1-ethyl-2-(4-hydroxymethylphenyl)pyrrolo[2,1,5-cd]indolizine

4-Acetyl-2-(4-(tert-butyldimethylsilanyloxymethyl)phenyl)-1-ethylpyrrolo[2,1,5-cd]indolizine was desilylated by the general synthetic principles outlined in example 81, step 7, to afford the title compound as a yellow foam in 34% yield. M.p. 73–77° C. MS(SP): m/z 317 (M+). ¹H-NMR (CDCl₃, 200 MHz) δ: 1.47 (t, 3H); 1.80 (t, 1H); 2.73 (s, 3H); 3.22 (q, 2H); 4.82 (d, 2H); 7.57 (d, 2H); 7.77 (d, 2H);

7.82–7.97 (m, 3H); 8.48 (dd, 1H). Analysis: calculated for $C_{21}H_{19}N_1O_2$+1.01 mol % water: C, 78.67; H, 6.09; N, 4.37%. Found: C, 78.67; H, 6.05; N, 4.15%.

EXAMPLE 98

4-Ethyl-3-(4-hydroxymethylphenyl)pyrrolo[2,1,5-cd]indolizine-1,2-dicarboxylic Acid 2-(4-(tert-Butyldimethylsilanyloxymethyl)phenyl)-1-ethylindolizine prepared in example 97, step 2, was reacted with dimethyl acetylene dicarboxylate by the general synthetic principle outlined in example 23, step 6, to afford dimethyl 4-ethyl-3-(4-(tert-butyldimethylsilanyloxymethyl)phenyl)pyrrolo[2,1,5-cd]indolizine-1,2-dicarboxylate, which was hydrolysed and desilylated by the general synthetic principle outlined in example 23, step 7, to afford 4-ethyl-3-(4-hydroxymethylphenyl)pyrrolo[2,1,5-cd]indolizine-1,2-dicarboxylic acid as yellow crystals in 63% yield. $^1$H-NMR (DMSO-$d_6$, 200 MHz) δ: 1.35 (t, 3H); 3.11 (q, 2H); 4.61 (d, 2H); 7.50 (d, 2H); 7.61 (d, 2H); 8.03 (dd, 1H); 8.32 (d, 1H); 8.42 (d, 1H).

EXAMPLE 99

1-Ethyl-4-hydroxymethyl-2-(4-methoxyphenyl)pyrrolo[2,1,5-cd]indolizine

The general synthetic pathway outlined in example 1 have been applied to proper starting materials in the preparation of methyl 4-ethyl-3-(4-methoxyphenyl)pyrrolo[2,1,5-cd]indolizine-1-carboxylate, which was reacted with lithium aluminium hydride by the general synthetic principle outlined in example 1, step 4, to afford 1-ethyl-4-hydroxymethyl-2-(4-methoxyphenyl)pyrrolo[2,1,5-cd]indolizine as yellow crystals in 83% yield. MS(SP): m/z 305 (M+). $^1$H-NMR (CDCl$_3$, 200 MHz) δ: 1.47 (t, 3H); 3.24 (q, 2H); 3.90 (s, 3H); 5.18 (s, 2H); 7.09 (d, 2H); 7.57 (s, 1H); 7.65 (dd, 1H); 7.73 (d, 2H); 7.92 (d, 1H); 8.01 (d, 1H).

EXAMPLE 100

1-Ethyl-2-(4-methoxyphenyl)-4-((2-piperidinoethoxy)methyl)pyrrolo[2,1,5-cd]indolizine 1-Ethyl-4-hydroxymethyl-2-(4-methoxyphenyl)pyrrolo[2,1,5-cd]indolizine was alkylated, using a proper alkylating agent, by the general synthetic principle outlined in example 2, to afford 1-ethyl-2-(4-methoxyphenyl)-4-((2-piperidinoethoxy)methyl)pyrrolo[2,1,5-cd]indolizine in 65% yield. $^1$H-NMR (CDCl$_3$, 200 MHz) δ: 1.33–1.64 (m, 9H); 1.40 (m, 4H); 2.57 (t, 2H); 3.23 (q, 2H); 3.67 (t, 2H); 3.89 (s, 3H); 5.03 (s, 2H); 7.08 (d, 2H); 7.53 (s, 1H); 7.62 (dd, 1H); 7.73 (d, 2H); 7.89 (d, 1H); 7.99 (d, 1H).

EXAMPLE 101

Dimethyl 3-(4-benzyloxyphenyl)-4-ethyl-7-methoxypyrrolo[2,1,5-cd]indolizine-1,2-dicarboxylate The general synthetic pathway outlined in example 23, step 1–5, have been applied to proper starting materials in the preparation of 2-(4-benzyloxyphenyl)-1-ethyl-6-methoxyindolizine, which was reacted with dimethyl acetylene dicarboxylate by the general synthetic principle outlined in example 23, step 6, to afford dimethyl 3-(4-benzyloxyphenyl)-4-ethyl-7-methoxypyrrolo[2,1,5-cd]indolizine-1,2-dicarboxylate as a red oil in 80% yield. $^1$H-NMR (CDCl$_3$, 200 MHz) δ: 1.36 (t, 3H); 3.02 (q, 2H); 3.60 (s, 3H); 3.98 (s, 3H); 4.14 (s, 3H); 5.15 (s, 2H); 7.04–7.52 (m, 10H); 7.81 (d, 1H).

EXAMPLE 102

3-(4-Benzyloxyphenyl)-4-ethyl-7-methoxypyrrolo[2,1,5-cd]indolizine-1,2-dicarboxylic Acid Dimethyl 3-(4-benzyloxyphenyl)-4-ethyl-7-methoxypyrrolo[2,1,5-cd]indolizine-1,2-dicarboxylate was hydrolysed by the general synthetic principle outlined in example 23, step 7, to afford 3-(4-benzyloxyphenyl)-4-ethyl-7-methoxypyrrolo[2,1,5-cd]indolizine-1,2-dicarboxylic acid as yellow crystals in 81% yield. M.p. 198–200° C. $^1$H-NMR (DMSO-$d_6$, 200 MHz) δ: 1.32 (t, 3H); 3.02 (q, 2H); 4.10 (s, 3H); 5.17 (s, 2H); 7.14 (d, 2H); 7.30–7.57 (m, 8H); 8.16 (d, 1H); 12.80 (br s, 2H).

EXAMPLE 103

2-(4-Benzyloxyphenyl)-1-ethyl-5-methoxypyrrolo[2,1,5-cd]indolizine 3-(4-Benzyloxyphenyl)-4-ethyl-7-methoxypyrrolo[2,1,5-cd]indolizine-1,2-dicarboxylic acid was decarboxylated by the general synthetic principle outlined in example 23, step 10, to afford 2-(4-benzyloxyphenyl)-1-ethyl-5-methoxypyrrolo[2,1,5-cd]indolizine as yellow crystals in 17% yield. M.p. 78–81° C. $^1$H-NMR (DMSO-$d_6$, 200 MHz) δ: 1.39 (t, 3H); 3.18 (q, 2H); 4.19 (s, 3H); 5.20 (s, 2H); 7.21 (d, 2H); 7.29–7.54 (m, 8H); 7.72 (d, 1H); 8.00 (d, 1H).

EXAMPLE 104

1-Ethyl-2-(4-hydroxyphenyl)-5-methoxypyrrolo[2,1,5-cd]indolizine 2-(4-Benzyloxyphenyl)-1-ethyl-5-methoxypyrrolo[2,1,5-cd]indolizine was hydrogenated by the general synthetic principles outlined in example 47, to afford 1-ethyl-2-(4-hydroxyphenyl)-5-methoxypyrrolo[2,1,5-cd]indolizine as a green solid in 93% yield. $^1$H-NMR (DMSO-$d_6$, 200 MHz) δ: 1.39 (t, 3H); 3.15 (q, 2H); 4.19 (s, 3H); 6.96 (d, 2H); 7.27–7.33 (m, 2H); 7.46 (d, 1H); 7.61 (d, 2H); 7.97 (d, 1H); 9.68 (br s, 1H).

EXAMPLE 105

Methyl 7-acetylamino-3-(4-benzyloxyphenyl)-4-ethylpyrrolo[2,1,5-cd]indolizine-1-carboxylate Step 1

5-Acetylamino-2-n-propylpyridine

A mixture of 5-amino-2-n-propylpyridine (example 23, step2) (62.7 g, 0.46 mol) and 45.7 g (0.483 mol) of acetic anhydride in 50 ml of acetic acid was refluxed for 3 hours in a nitrogen atmosphere. The mixture was evaporated and the oily residue was made slightly alkaline (pH=9.2) with a 10% sodium hydroxide solution. The precipitate was filtered off, and triturated with a mixture of water (1000 ml) and heptane (500 ml). The precipitate was filtered off, dried and resuspended in 400 ml of heptane. The resulting precipitate was filtered off and dried to yield 65.7 g (80%) of 5-acetylamino-2-n-propylpyridine. M.p. 122–24° C. $^1$H-NMR (CDCl$_3$, 200 MHz) δ: 0.95 (t, 3H), 1.72 (sext, 2H), 2.20 (s, 3H), 2.73 (t, 2H), 7.10 (d, 1H), 7.70 (br s, 1H), 8.09 (dd, 1H), 8.43 (d, 1H).

Step 2

6-Acetylamino-2-(4-benzyloxyphenyl)-1-ethylindolizine

A solution of 5-acetylamino-2-n-propylpyridine (50.0 g, 0.281 mol) and 4-benzyloxyphenacylbromide (85.63 g, 0.281 mol) in 440 ml of dry acetone was heated to reflux for 16 hours. The mixture was cooled and the precipitated pyridinium bromide was isolated and suspended in 625 ml of water followed by the addition of sodium hydrogen carbonate (94.4 g). The mixture was refluxed for 16 hours. The resulting precipitate was filtered off, washed with water and dried to yield overall 96.5 g (89%) of 6-acetylamino-2-(4-benzyloxyphenyl)-1-ethylindolizine. $^1$H-NMR (DMSO-$d_6$, 200 MHz) δ: 1.10 (t, 3H), 2.05 (s, 3H), 2.80 (q, 2H), 5.15 (s, 2H), 6.58 (d, 1H), 7.30–7.55 (m, 8H), 7.62 (s, 1H), 8.88 (s, 1H), 9.80 (s, 1H).

Step 3

Methyl 7-acetylamino-3-(4-benzyloxyphenyl)-4-ethylpyrrolo[2,1,5-cd]indolizine-1-carboxylate A solution of 6-acetylamino-2-(4-benzyloxyphenyl)-1-ethylindolizine (38.5 g, 0.1 mol) in 3000 ml of toluene was stirred in a nitrogen atmosphere at 50° C. while methyl propiolate (10.2 ml, 0.115 mol) was added dropwise. The mixture was heated to 90° C. and stirring was continued for 3 hours. The mixture was cooled to 4° C. and 2,3-dichloro-5,6-dicyano-1,4-benzoquinone (22.6 g, 0.1 mol) was added in portions. The cooling source was removed and stirring was continued for 16 hours. The mixture was filtered through celite and the celite pad was washed several times with toluene. The combined filtrates were evaporated to app. 500 ml and 1000 ml of petroleum ether was added. The precipitate was filtered off and dried to yield 38.7 g (83%) of the title compound. M.p. 210–13° C. $^1$H-NMR (DMSO-$d_6$, 200 Hz) δ: 1.38 (t, 3H), 2.27 (s, 3H), 3.15 (q, 2H), 3.96 (s, 3H), 5.18 (s, 2H), 7.20 (d, 2H), 7.35–7.55 (m, 5H), 7.75 (d, 2H), 7.90 (s, 1H), 8.13 (d, 1H), 8.95 (d, 1H), 11.78 (s, 1H).

EXAMPLE 106

7-Acetylamino-3-(4-benzyloxyphenyl)-4-ethylpyrrolo[2,1,5-cd]indolizine-1-carboxylic Acid A mixture of methyl 7-acetylamino-3-(4-benzyloxyphenyl)-4-ethylpyrrolo[2,1,5-cd]indolizine-1-carboxylate (17.15 g, 0.0368 mol) and 85% potassium hydroxide (36.4 g, 0.551 mol) in 1700 ml of methanol was refluxed for 16 hours. The mixture was filtered and the precipitate (shown to be starting material) was further refluxed for 48 hours in 800 ml of methanol and 17.4 g of 85% potassium hydroxide. The mixture was filtered and the filtrate was combined with the first filtrate. The resulting mixture was evaporated to nearly dryness and 1000 ml of water was added. The pH was adjusted to 1.0 with a 6M hydrochloric acid solution. The precipitate was filtered off and dried to afford 15.57 g (94%) of the title compound. M.p. 244–46° C. $^1$H-NMR (DMSO-$d_6$, 200 MHz) δ: 1.38 (t, 3H), 2.27 (s, 3H), 3.13 (q, 2H), 3.97 (s, 3H), 5.19 (s, 2H), 7.22 (q, 2H), 7.38–7.55 (m, 5H), 7.75 (d, 2H), 7.91 (s, 1H), 8.12 (d, 1H), 8.95 (d, 1H), 11.78 (s, 1H).

EXAMPLE 107

5-Acetylamino-2-(4-benzyloxyphenyl)-1-ethylpyrrolo[2,1,5-cd]indolizine

A mixture of 7-acetylamino-3-(4-benzyloxyphenyl)-4-ethylpyrrolo[2,1,5-cd]indolizine-1-carboxylic acid, copper powder (0.52 g), and 130 ml of freshly purified quinoline was heated to 200 ° C. for 2 hours in a nitrogen atmosphere. The copper catalyst was filtered off from the warm mixture. Ice (200 g) was added to the filtrates and the pH was adjusted to 1.5 by addition of a 6M hydrochloric acid solution. The resulting mixture was extracted with dichloromethane. The extract was washed with a 1M hydrochloric acid solution (2×300 ml) followed by a saturated sodium hydrogen carbonate solution (2×250 ml). The dried extract (magnesium sulfate) was evaporated and the residue chromatographed over silica gel with toluene/ethyl acetate (2:1) as eluent to yield 1.52 (64%) of the title compound. M.p. 211–13° C. $^1$H-NMR (DMSO-$d_6$, 200 MHz) δ: 1.38 (t, 3H), 2.22 (s, 3H), 3.18 (q, 2H), 5.18 (s, 2H), 7.23 (d, 2H), 7.35–7.55 (m, 7H), 7.75 (d, 2H), 8.03 (d, 1H), 8.22 (d, 1H), 10.50 (s, 1H).

EXAMPLE 108

5-Acetylamino-1-ethyl-2-(4-hydroxyphenyl)pyrrolo[2,1,5-cd]indolizine

5-Acetylamino-2-(4-benzyloxyphenyl)-1-ethylpyrrolo[2,1,5-cd]indolizine (0.2 g, 0.49 mmol) was debenzylated by the general principles outlined in example 12 to afford 150 mg (96%) of the title compound. M.p. 147–49° C. $^1$H-NMR (DMSO-$d_6$, 200 MHz) δ: 1.38 (t, 3H), 2.33 (s, 3H), 3.18 (q, 2H), 6.98 (d, 2H), 7.48 (d, 1H), 7.52 (d, 1H), 7.62 (d, 2H), 7.98 (d, 1H), 8.20 (d, 1H), 9.70 (br s, 1H), 10.50 (s, 1H).

EXAMPLE 109

5-Amino-2-(4-benzyloxyphenyl)-1-ethylpyrrolo[2,1,5-cd]indolizine

A mixture of 5-acetylamino-2-(4-benzyloxyphenyl)-1-ethylpyrrolo[2,1,5-cd]indolizine (1.1 g, 2.69 mmol), sodium hydroxide (4.3 g, 0.108 mol), water (100 ml) and ethanol (100 ml) was refluxed for 16 hours in a nitrogen atmosphere. The cooled mixture was filtered and the filter cake was washed several times with ethanol. The combined filtrates were extracted with dichloromethane. The combined extracts were washed with brine, clarified with norite A, dried (magnesium sulfate) and evaporated. The residue was dried to afford 980 mg (99%) of the title compound as yellow crystals. M.p. 123–27° C. $^1$H-NMR (DMSO-$d_6$, 200 MHz) δ: 1.37 (t, 3H), 3.12 (q, 2H), 5.18 (s, 2H), 6.28 (br s, 2H), 6.88 (d, 2H), 7.12–7.75 (m, 11H).

EXAMPLE 110

5-Amino-1-ethyl-2-(4-hydroxyphenyl)pyrrolo[2,1,5-cd]indolizine

5-Amino-2-(4-benzyloxyphenyl)-1-ethylpyrrolo[2,1,5-cd]indolizine (0.15 g, 0.41 mmol) was debenzylated by the general principles outlined in example 12 to afford 90 mg (80%) of the title compound. M.p. 147–49° C. $^1$H-NMR (DMSO-$d_6$, 200 MHz) δ: 1.36 (t, 3H), 3.08 (q, 2H), 6.22 (br s, 2H), 6.85 (d, 1H), 6.95 (d, 2H), 7.18 (d, 1H), 7.26 (d, 1H), 7.56 (d, 2H), 7.69 (d, 1H).

What is claimed is:

1. A compound of formula I

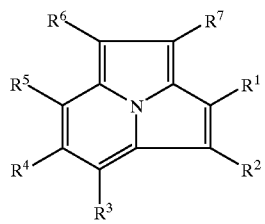

(I)

wherein
R$^1$ is phenyl substituted with one or two substitutents selected from halogen, OH, NO$_2$, CN, SH, C$_{2-4}$-alkyl optionally substituted with one to three halogen(s), C$_{1-4}$-alkoxy, C$_{1-4}$-alkylthio, benzyloxy, OCOR$^{36}$, OCONHR$^{38}$, OCONR$^{36}$R$^{37}$, OSO$_2$NHR$^{35}$ or OSO$_2$NR$^{38}$R$^{37}$ wherein R$^{36}$ and R$^{37}$ independently are C$_{1-6}$-alkyl; and R$^2$ is H, C$_{1-4}$-alkyl, C$_{2-4}$-alkenyl or C$_{2-4}$-alkynyl; and R$^3$ is H, OH, benzyloxy, R$^{10}$, OR$^{10}$, COR$^{10}$, NHR$^{10}$, NR$^{10}$R$^{11}$, NH—CO—R$^{10}$, NR$^{12}$—CO—

R$^{10}$ or R$^{13}$OR$^{10}$ wherein R$^{12}$ is C$_{1-6}$-alkyl and R$^{13}$ is C$_{1-7}$-alkylene; and R$^4$ is H, OH, benzyloxy, R$^{14}$, OR$^{14}$, COR$^{14}$, NHR$^{14}$, NR$^{14}$R$^{15}$, NH—CO—R$^{14}$, NR$^{16}$—CO—

R$^{14}$ or R$^{17}$OR$^{14}$ wherein R$^{18}$ is C$_{1-8}$-alkyl and R$^{17}$ is C$_{1-7}$-alkylene; and R$^5$ is H, OH, benzyloxy, R$^{18}$, OR$^{18}$, COR$^{18}$, NHR$^{18}$, NR$^{18}$R$^{19}$, NH—CO—R$^{18}$, NR$^{20}$—CO—

R$^{18}$ or R$^{21}$OR$^{18}$ wherein R$^{20}$ is C$_{1-8}$-alkyl and R$^{21}$ is C$_{1-7}$-alkylene; and R$^6$ is H, R$^{22}$, OR$^{22}$, R$^{23}$OR$^{22}$, COR$^{22}$, COR$^{24}$, R$^{25}$OR$^{28}$—NR$^{27}$R$^{28}$ or phenyl optionally substituted with OR$^{22}$, wherein R$^{23}$, R$^{25}$ and R$^{26}$ independently are C$_{1-7}$-alkylene, R$^{24}$ is phenyl optionally substituted with OR$^{22}$, and R$^{27}$ and R$^{28}$ together with the nitrogen atom form a saturated, partly saturated or unsaturated 4 to 6 membered heterocyclic ring containing one to four N, O or S atom(s) or a combination thereof; and R$^7$ is H, R$^{29}$, OR$^{20}$, R$^{30}$OR$^{29}$, COR$^{29}$, CONHR$^{29}$, COOR$^{29}$, CONR$^{29}$R$^{29}$, COR$^{31}$, R$^{32}$OR$^{33}$—NR$^{34}$R$^{35}$, phenyl optionally substituted with OR$^{29}$, wherein R$^{30}$, R$^{32}$ and R$^{33}$ independently are C$_{1-7}$-alkylene, R$^{31}$ is phenyl optionally substituted with OR$^{29}$, and R$^{34}$ and R$^{35}$ together with the nitrogen atom form a saturated, partly saturated or unsaturated 4 to 6 membered heterocyclic ring containing one to four N, O or S atom(s) or a combination thereof; and wherein R$^{10}$, R$^{11}$, R$^{14}$, R$^{16}$, R$^{18}$, R$^{19}$, R$^{22}$ and R$^{29}$ independently are C$_{1-12}$-alkyl, C$_{2-12}$-alkenyl or C$_{2-12}$-alkynyl each of which is optionally substituted with OH, COOH, COOR$^{38}$, CONHR$^{39}$, CONR$^{40}$, NHR$^{41}$, NR$^{42}$R$^{43}$, NHCOR$^{44}$, NHSO$_2$R$^{45}$, SOR$^{46}$, SO$_2$R$^{47}$, SONHR$^{45}$, SO$_2$NR$^{49}$R$^{50}$ or a saturated, partly saturated or unsaturated 4 to 6 membered heterocyclic ring containing one to four N, O or S atom(s) or a combination thereof, wherein R$^{38}$, R$^{39}$, R$^{40}$, R$^{41}$, R$^{42}$, R$^{43}$, R$^{44}$, R$^{45}$, R$^{46}$, R$^{47}$, R$^{48}$, R$^{49}$ and R$^{50}$ independently are C$_{1-7}$-alkyl;

or geometric or optical isomers, pharmaceutically acceptable esters, ethers or salts thereof.

2. A compound according to claim 1 in which R$^1$ is phenyl substituted with OH.

3. A compound according to claim 1 in which R$^2$ is C$_{1-4}$-alkyl.

4. A compound according to claim 1 in which R$^3$ is H or R$^{13}$OR$^{10}$ wherein R$^{10}$ and R$^{13}$ are as defined in claim 1.

5. A compound according to claim 1 in which R$^3$ is H or CH$_2$OR$^{10}$ wherein R$^{10}$ is as defined in claim 1.

6. A compound according to claim 1 in which R$^4$ is H, OH or OCH$_3$.

7. A compound according to claim 1 in which R$^5$ is H, OH or OCH$_3$.

8. A compound according to claim 1 in which R$^6$ is H, R$^{22}$ or R$^{23}$OR$^{22}$ wherein R$^{22}$ and R$^{23}$ are as defined in claim 1.

9. A compound according to claim 1 in which R$^6$ is H, R$^{22}$ or CH$_2$OR$^{22}$ wherein R$^{22}$ is as defined in claim 1.

10. A compound according to claim 1 in which R$^7$ is H, R$^{29}$, R$^{30}$OR$^{29}$ or phenyl substituted with OR$^{29}$ wherein R$^{29}$ and R$^{30}$ are as defined in claim 1.

11. A compound according to claim 1 in which R$^7$ is H, R$^{29}$, CH$_2$OR$^{29}$ or phenyl substituted with OR$^{29}$ wherein R$^{29}$ is as defined in claim 1.

12. A compound selected from the following:

2-(4-Benzyloxyphenyl)-1-ethyl-4-hydroxymethylpyrrolo[2,1,5-cd]indolizine, 2-(4-Benzyloxyphenyl)-1-ethyl-4-((2-piperidinoethoxy)methyl)pyrrolo[2,1,5-cd]indolizine, 2-(4-Benzyloxyphenyl)-1-ethyl-4-methoxymethylpyrrolo[2,1,5-cd]indolizine, 2-(4-Benzyloxyphenyl)-1-ethyl-4-propoxymethylpyrrolo[2,1,5-cd]indolizine, 2-(4-Benzyloxyphenyl)-4-((3-dimethylaminopropoxy)methyl)-1-ethylpyrrolo[2,1,5-cd]indolizine, 2-(4-Benzyloxyphenyl)-4-((2-diethylaminoethoxy)methyl)-1-ethylpyrrolo[2,1,5-cd]indolizine, 2-(4-Benzyloxyphenyl)-1-ethyl-4-((2-pyrrolidinoethoxy)methyl)pyrrolo[2,1,5-cd]indolizine, 2-(4-Benzyloxyphenyl)-1-ethyl-4-((2-(morpholine-4-yl)ethoxy)methyl)pyrrolo[2,1,5-cd]indolizine, 2-(4-Benzyloxyphenyl)-4-((2-dimethylaminoethoxy)methyl)-1-ethylpyrrolo[2,1,5-cd]indolizine, 2-(4-Benzyloxyphenyl)-1-ethyl-4-((3-piperidinopropoxy)methyl)pyrrolo[2,1,5-cd]indolizine, 6-[2-(4-Benzyloxyphenyl)-1-ethylpyrrolo[2,1,5-cd]indolizine-4-ylmethyl]hexanoic acid dimethylamide, 1-Ethyl-2-(4-hydroxyphenyl)-4-((2-piperidinoethoxy)methyl)pyrrolo[2,1,5-cd]indolizine, 1-Ethyl-2-(4-hydroxyphenyl)-4-methoxymethylpyrrolo[2,1,5-cd]indolizine, 1-Ethyl-2-(4-hydroxyphenyl)-4-propoxymethylpyrrolo[2,1,5-cd]indolizine, 4-((3-Dimethylaminopropoxy)methyl)-1-ethyl-2-(4-hydroxyphenyl)pyrrolo[2,1,5-cd]indolizine, 4-((2-Diethylaminoethoxy)methyl)-1-ethyl-2-(4-hydroxyphenyl)pyrrolo[2,1,5-cd]indolizine 1-Ethyl-2-(4-hydroxyphenyl)-4-((2-pyrrolidinoethoxy)methyl)pyrrolo[2,1,5-cd]indolizine, 1-Ethyl-2-(4-hydroxyphenyl)-4-((2-(morpholine-4-yl)ethoxy))methyl)pyrrolo[2,1,5-cd]indolizine, 4-((2-dimethylaminoethoxy)methyl)-1-ethyl-2-(4-hydroxyphenyl)pyrrolo[2,1,5-cd]indolizine, 1-Ethyl-2-(4-hydroxyphenyl)-4-((3-piperdinopropoxy)methyl)pyrrolo[2,1,5-cd]indolizine, 6-[1-ethyl-2-(4-hydroxyphenyl)pyrrolo[2,1,5-cd]indolizine-4-ylmethoxy]hexanoic acid dimethylamide, 5-Benzyloxy-2-(4-benzyloxyphenyl)-1-ethyl-3-hydroxymethylpyrrolo[2,1,5-cd]indolizine, 1-Ethyl-3-hydroxymethyl-2-(4-methoxyphenyl)pyrrolo[2,1,5-cd]indolizine, 2-(4-Benzyloxyphenyl)-3-hydroxymethylpyrrolo[2,1,5-cd] indolizine,
2-(4-Benzyloxyphenyl)-1-ethyl-3-hydroxymethylpyrrolo[2,1,5-cd]indolizine,
5-Benzyloxy-2-(4-benzyloxyphenyl)-1-ethyl-3-((2-piperidinoethoxy)methyl)pyrrolo[2,1,5-cd]indolizine,
5-Benzyloxy-2-(4-benzyloxyphenyl)-1-ethyl-3-((3-piperidinopropoxy)methyl)pyrrolo[2,1,5-cd]indolizine,
5-Benzyloxy-2-(4-benzyloxyphenyl)-1-ethyl-3-((6-piperidinohexyloxy)methyl)-pyrrolo[2,1,5-cd]indolizine,
5-Benzyloxy-2-(4-benzyloxyphenyl)-1-ethyl-3-((7-piperidinoheptyloxy)methyl)pyrrolo[2,1,5-cd]indolizine,
5-Benzyloxy-2-(4-benzyloxyphenyl)-1-ethyl-3-((8-piperidinooctyloxy)methyl)pyrrolo[2,1,5-cd]indolizine,
2-(4-Benzyloxyphenyl)-1-ethyl-3-((2-piperidinoethoxy)methyl)pyrrolo[2,1,5-cd]indolizine,
2-(4-Benzyloxyphenyl)-1-ethyl-3-methoxymethylpyrrolo[2,1,5-cd]indolizine,
1-Ethyl-3-methoxymethyl-2-(4-methoxyphenyl)pyrrolo[2,1,5-cd]indolizine,
2-(4-Benzyloxyphenyl)-3-methoxymethylpyrrolo[2,1,5-cd] indolizine,
5-Benzyloxy-2-(4-benzyloxyphenyl)-1-ethyl-3-methoxymethylpyrrolo[2,1,5-cd]indolizine,
5-Benzyloxy-2-(4-benzyloxyphenyl)-1-ethyl-3-((5-piperidinopentoxy)methyl)pyrrolo[2,1,5-cd]indolizine,
5-Benzyloxy-2-(4-benzyloxyphenyl)-1-ethyl-3-((4-piperidinobutoxy)methyl)pyrrolo[2,1,5-cd]indolizine,
5-Benzyloxy-2-(4-benzyloxyphenyl)-1-ethyl-3-((4-pyrrolidinobutoxy)methyl)pyrrolo[2,1,5-cd]indolizine,
5-Benzyloxy-2-(4-benzyloxyphenyl)-3-((but-3-enyloxy) methyl)-1-ethylpyrrolo[2,1,5-cd]indolizine,
1-Ethyl-5-hydroxy-2-(4-hydroxyphenyl)-3-((8-piperidinooctyoxy)methyl)pyrrolo[2,1,5-cd]indolizine,
1-Ethyl-5-hydroxy-2-(4-hydroxyphenyl)-3-methoxymethylpyrrolo[2,1,5-cd]indolizine,
1-Ethyl-2-(4-hydroxyphenyl)-3-((2-piperidinoethoxy) methyl)pyrrolo[2,1,5-cd]indolizine,
1-Ethyl-5-hydroxy-2-(4-hydroxyphenyl)-3-((2-piperidinoethoxy)methyl)pyrrolo[2,1,5-cd]indolizine,
1-Ethyl-5-hydroxy-2-(4-hydroxyphenyl)-3-((3-piperidinopropoxy)methyl)pyrrolo[2,1,5-cd]indolizine,
1-Ethyl-2-(4-hydroxyphenyl)-3-methoxymethylpyrrolo[2,1,5-cd]indolizine,
1-Ethyl-5-hydroxy-2-(4-hydroxyphenyl)-3-((6-piperidinohexyloxy)methyl)pyrrolo[2,1,5-cd]indolizine,
2-(4-Hydroxyphenyl)-3-methoxymethylpyrrolo[2,1,5-cd] indolizine,
1-Ethyl-5-hydroxy-2-(4-hydroxyphenyl)-3-((5-piperidinopentoxy)methyl)pyrrolo[2,1,5-cd]indolizine,
1-Ethyl-3-hydroxymethyl-2-(4-hydroxyphenyl)pyrrolo[2,1,5-cd]indolizine,
3-Hydroxymethyl-2-(4-hydroxyphenyl)pyrrolo[2,1,5-cd] indolizine,
1-Ethyl-5-hydroxy-3-hydroxymethyl-2-(4-hydroxyphenyl) pyrrolo[2,1,5-cd]indolizine,
3-dimethylaminomethyl-1-ethyl-2-(4-hydroxyphenyl) pyrrolo[2,1,5-cd]indolizine,
2-(4-Benzyloxyphenyl)-3-dimethylaminomethyl-1-ethylpyrrolo[2,1,5-cd]indolizine,
3-Benzoyl-2-(4-benzyloxyphenyl)-1-ethylpyrrolo[2,1,5-cd] indolizine,
1-Ethyl-5-hydroxy-2-(4-hydroxyphenyl-4-(1-oxopropyl) pyrrolo[2,1,5-cd]indolizine,
4-Benzoyl-1-ethyl-2-(4-methoxyphenyl)pyrrolo[2,1,5-cd] indolizine,
1-Ethyl-2-(4-methoxyphenyl)-4-[4-(2-piperidinoethoxy) phenyl]pyrrolo[2,1,5-cd]indolizine,
1-Ethyl-2-(4-hydroxyphenyl)-4-[4-(2-piperidinoethoxy) phenyl]pyrrolo[2,1,5-cd]indolizine,
4-Acetyl-1-ethyl-7-benzyloxy-2-(4-benzyloxyphenyl) pyrrolo[2,1,5-cd]indolizine,
4-Acetyl-1-ethyl-7-hydroxy-2-(4-hydroxyphenyl)pyrrolo[2,1,5-cd]indolizine,
4-Acetyl-2-(4-benzyloxyphenyl)-1-ethyl-7-hydroxymethylpyrrolo[2,1,5-cd]indolizine,
4-Acetyl-1-ethyl-7-hydroxymethyl-2-(4-hydroxyphenyl) pyrrolo[2,1,5-cd]indolizine,
2-(4-Benzyloxyphenyl)-1-ethyl-7-hydroxymethylpyrrolo[2,1,5-cd]indolizine,
1-Ethyl-7-hydroxymethyl-2-(4-hydroxyphenyl)pyrrolo[2,1,5-cd]indolizine,
2-(4-Benzyloxyphenyl)-1-ethyl-7-((2-pyrrolidinoethoxy) methyl)pyrrolo[2,1,5-cd]indolizine,
2-(4-Benzyloxyphenyl)-1-ethyl-7-((2-piperidinoethoxy) methyl)pyrrolo[2,1,5-cd]indolizine,
2-(4-Benzyloxyphenyl)-1-ethyl-7-((3-dimethylaminopropoxy)methyl)pyrrolo[2,1,5-cd] indolizine,
2-(4-Benzyloxyphenyl)-1-ethyl-7-((3-piperidinopropoxy) methyl)pyrrolo[2,1,5-cd]indolizine,
1-Ethyl-2-(4-hydroxyphenyl)-7-((2-pyrrolidinoethoxy) methyl)pyrrolo[2,1,5-cd]indolizine,
1-Ethyl-2-(4-hydroxyphenyl)-7-((2-piperidinoethoxy) methyl)pyrrolo[2,1,5-cd]indolizine,
1-Ethyl-2-(4-hydroxyphenyl)-7-((3-dimethylaminopropoxy)methyl)pyrrolo[2,1,5-cd] indolizine,
1-Ethyl-2-(4-hydroxyphenyl)-7-((3-piperidinopropoxy) methyl)pyrrolo[2,1,5-cd]indolizine,
1-Ethyl-4-hydroxymethyl-2-(4-methoxyphenyl)pyrrolo[2,1,5-cd]indolizine,
1-Ethyl-2-(4-methoxyphenyl)-4-((2-piperidinoethoxy) methyl)pyrrolo[1,2,5-cd]indolizine,
2-(4-Benzyloxyphenyl)-1-ethyl-5-methoxypyrrolo[2,1,5-cd]indolizine,
1-Ethyl-2-(4-hydroxyphenyl)-5-methoxypyrrolo[2,1,5-cd] indolizine,
5-Acetylamino-2-(4-benzyloxyphenyl)-1-ethylpyrrolo[2,1,5-cd]indolizine,
5-Acetylamino-1-ethyl-2-(4-hydroxyphenyl)pyrrolo[2,1,5-cd]indolizine,
1-Ethyl-6-hydroxymethyl-2-(4-hydroxyphenyl)-3-[4-(2-piperidinoethoxy)phenyl]pyrrolo[2,1,5-cd]indolizine,
1-Ethyl-2-(3-fluoro-4-hydroxyphenyl)-3-(1-oxo-3-piperidinopropyl)pyrrolo[2,1,5cd]indolizine,
2-[(4-Hydroxymethyl)phenyl]-1-methylethylpyrrolo[2,1,5-cd]indolizine,
N-[2-(4-Hydroxyphenyl)-1-ethyl-pyrrolo[2,1,5-cd] indolizine-5-yl]-butyramide;
or geometric or optical isomers, pharmaceutical acceptable esters, ethers of salts thereof.

13. A pharmaceutical composition comprising an estrogen agonistic effective amount of a compound of claim 1, together with a pharmaceutically acceptable carrier or diluent.

14. The pharmaceutical composition of claim 13 in the form of an oral dosage unit or parenteral dosage unit.

15. A method for treating estrogen deficiency, comprising administering to a mammal in need thereof an estrogen agonistic effective amount of a compound of claim 1.

16. A compound selected from the following:
3-(4-Benzyloxyphenyl)-4-ethyl-pyrrolo[2,1,5-cd] indolizine-1-carboxylic acid dimethylamide,
5-Benzyloxy-2-(4-benzyloxyphenyl)-3-((5-chloropentyloxy)methyl)-1-ethylpyrrolo[2,1,5-cd] indolizine, 5-Benzyloxy-2-(4-benzyloxyphenyl)-3-((4-chlorobutoxy)methyl)-1-ethylpyrrolo[2,1,5-cd]indolizine, 5-Benzyloxy-2-(4-benzyloxyphenyl)-1-ethyl-3-((5-methoxypentoxy)methyl)pyrrolo[2,1,5-cd]indolizine, 1-Ethyl-5-hydroxy-2-[4-hydroxyphenyl)-3-((5-methoxypentoxy)methyl)pyrrolo[2,1,5-cd]indolizine, 2-[(2-Dimethylaminoethyl)methylcarbamoyl]-4-ethyl-6-methoxy-3-(4-methoxyphenyl)pyrrolo[2,1,5-cd]indolizine-1-carboxylic acid, 2-[(2-dimethylaminoethyl)methylcarbamoyl]-4-ethyl-3-(4-methoxyphenyl)pyrrolo[2,1,5-cd]indolizine-1-carboxylic acid, 2-[(2-dimethylaminoethyl)methylcarbamoyl]-4-ethyl-6-methoxy-3-(4-methoxyphenyl)pyrrolo[2,1,5-cd]indolizine, 2-[(2-Dimethylaminoethyl)methylcarbamoyl]-4-ethyl-3-(4-methoxyphenyl)pyrrolo[2,1,5-cd]indolizine, 2-[(2-Dimethylaminoethyl)methylcarbamoyl]-4-ethyl-3-(4-hydroxyphenyl)-6-methoxypyrrolo[2,1,5-cd]indolizine, 2-[(2-Dimethylaminoethyl)methylcarbamoyl]-4-ethyl-3-(4-hydroxyphenyl)pyrrolo[2,1,5-cd]indolizine, 3-Benzyl-1-ethyl-2-(4-hydroxyphenyl)pyrrolo[2,1,5-cd]indolizine, 2-(4-Acetoxyphenyl)-3-benzyl-1-ethylpyrrolo[2,1,5-cd]indolizine, 5-Acetoxy-2-(4-acetoxyphenyl)-1-ethyl-4-(1-oxopropyl)pyrrolo[2,1,5-cd]indolizine, 4-(4-Benzyloxybenzoyl)-1-ethyl-2-(4-methoxyphenyl)pyrrolo[2,1,5-cd]indolizine, 3-(4-Benzyloxyphenyl)-4-ethyl-5-hydroxymethylpyrrolo[2,1,5-cd]indolizine-1,2-dicarboxylic acid, 3-(4-Benzyloxyphenyl)-4-ethyl-5-hydroxymethylpyrrolo[2,1,5-cd]indolizine-1-carboxylic acid, 5-Acetoxymethyl-3-(4-benzyloxyphenyl)-2-dimethylcarbamoylpyrrolo[2,1,5-cd]indolizine-1-carboxylic acid Dimethyl 3-(4-benzyloxyphenyl)-5-hydroxymethylpyrrolo[2,1,5-cd]indolizine-1,2-dicarboxylate, 4-Acetyl-1-ethyl-2-(4-hydroxymethylphenyl)pyrrolo[2,1,5-cd]indolizine, 4-Ethyl-3-(4-hydroxymethylphenyl)pyrrolo[2,1,5-cd]indolizine-1,2-dicarboxylic acid, Dimethyl 3-(4-benzyloxyphenyl)-4-ethyl-7-methoxypyrrolo[2,1,5-cd]indolizine-1,2-dicarboxylate, 3-(4-Benzyloxyphenyl)-4-ethyl-7-methoxypyrrolo[2,1,5-cd]indolizine-1,2-dicarboxylic acid, Methyl 7-acetylamino-3-(4-benzyloxyphenyl)-4-ethylpyrrolo[2,1,5-cd]indolizine-1-carboxylate, 7-Acetylamino-3-(4-benzyloxyphenyl)-4-ethylpyrrolo[2,1,5-cd]indolizine-1-carboxylic acid, 5-Amino-2-(4-benzyloxyphenyl)-1-ethylpyrrolo[2,1,5-cd]indolizine, 5-Amino-1-ethyl-2-(4-hydroxyphenyl)pyrrolo[2,1,5-cd]indolizine, 2-(4-Hydroxyphenyl)-1-(6-piperidinohexyl)pyrrolo[2,1,5-cd]indolizine, 1-(6-Carboxyhexyl)-2-(4-hydroxyphenyl)pyrrolo[2,1,5-cd]indolizine, 1-Ethyl-2-[4-hydroxy-2-(1-oxo-3-piperidinopropyl)phenyl]pyrrolo[2,1,5-cd]indolizine, 2-[2-(2-dimethylaminoethoxy)phenyl]-4-hydroxy]phenyl-1-ethylpyrrolo[2,1,5-cd]indolizine, or geometric or optical isomers, pharmaceutical acceptable esters, ethers or salts thereof.

* * * * *